US012232885B2

(12) United States Patent
Casey et al.

(10) Patent No.: US 12,232,885 B2
(45) Date of Patent: Feb. 25, 2025

(54) SYSTEM FOR MODELING PATIENT SPINAL CHANGES

(71) Applicant: Carlsmed, Inc., Carlsbad, CA (US)

(72) Inventors: Niall Patrick Casey, Carlsbad, CA (US); Rodrigo Junqueira Nicolau, Cardiff, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 18/408,452

(22) Filed: Jan. 9, 2024

(65) Prior Publication Data

US 2024/0225531 A1 Jul. 11, 2024

Related U.S. Application Data

(60) Provisional application No. 63/437,975, filed on Jan. 9, 2023.

(51) Int. Cl.

| | |
|---|---|
| ***G06T 17/00*** | (2006.01) |
| ***A61B 5/00*** | (2006.01) |
| ***A61F 2/30*** | (2006.01) |
| ***G06T 7/00*** | (2017.01) |

(52) U.S. Cl.

CPC ........ *A61B 5/4566* (2013.01); *A61F 2/30942* (2013.01); *G06T 7/0012* (2013.01); *G06T 17/00* (2013.01); *G06T 2207/30012* (2013.01)

(58) Field of Classification Search

CPC . A61B 5/4566; A61F 2/30942; G06T 7/0012; G06T 17/00; G06T 2207/30012

See application file for complete search history.

(56) References Cited

U.S. PATENT DOCUMENTS

| | | | |
|---|---|---|---|
| 4,704,686 | A | 11/1987 | Aldinger |
| 6,772,026 | B2 | 8/2004 | Bradbury |
| 7,174,282 | B2 | 2/2007 | Hollister et al. |
| 7,799,077 | B2 | 9/2010 | Lang |
| 8,246,680 | B2 | 8/2012 | Betz |
| 8,265,949 | B2 | 9/2012 | Haddad |
| 8,275,594 | B2 | 9/2012 | Lin |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the Slot radiography of the Sonialvision safire series clinical application." Medical Now, No. 78; Aug. 2015, 4 pages.

(Continued)

*Primary Examiner* — Yuhui R Pan

(74) *Attorney, Agent, or Firm* — Perkins Coie LLP

(57) ABSTRACT

Systems and methods for modeling anatomical changes in a patient after installation of a patient-specific implant are disclosed. The system can model changes to a thoracic spine based on changes to the lumbar spine in a patient. The system can calculate and display reciprocal changes to nearby anatomy due to correction of index anatomy. For example, the system models the anatomical changes to the thoracic and cervical spines based on corrections to the lumbar spine.

27 Claims, 22 Drawing Sheets

(56) References Cited

U.S. PATENT DOCUMENTS

| | | | | |
|---|---|---|---|---|
| 8,337,507 | B2 | 12/2012 | Lang | |
| 8,394,142 | B2 | 3/2013 | Bertagnoli | |
| 8,457,930 | B2 | 6/2013 | Shroeder | |
| 8,556,983 | B2 | 10/2013 | Bojarski et al. | |
| 8,644,568 | B1 | 2/2014 | Hoffman | |
| 8,735,773 | B2 | 5/2014 | Lang | |
| 8,758,357 | B2 | 6/2014 | Frey | |
| 8,775,133 | B2 | 7/2014 | Schroeder | |
| 8,781,557 | B2 | 7/2014 | Dean | |
| 8,843,229 | B2 | 9/2014 | Vanasse | |
| 8,855,389 | B1 | 10/2014 | Hoffman | |
| 8,870,889 | B2 | 10/2014 | Frey | |
| 9,198,678 | B2 | 12/2015 | Frey et al. | |
| 9,208,558 | B2 | 12/2015 | Dean | |
| 9,445,907 | B2 | 9/2016 | Meridew | |
| 9,542,525 | B2 | 1/2017 | Arisoy et al. | |
| 9,642,633 | B2 | 5/2017 | Frey et al. | |
| 9,693,831 | B2 | 7/2017 | Mosnier et al. | |
| 9,707,058 | B2 | 7/2017 | Bassett | |
| 9,775,680 | B2 | 10/2017 | Bojarski et al. | |
| 9,782,228 | B2 | 10/2017 | Mosnier et al. | |
| 9,993,341 | B2 | 6/2018 | Vanasse | |
| 10,292,770 | B2 | 5/2019 | Ryan | |
| 10,390,958 | B2 | 8/2019 | Maclennan | |
| 10,646,258 | B2 | 5/2020 | Donner et al. | |
| 11,185,369 | B2 | 11/2021 | Ryan | |
| 11,793,577 | B1 | 10/2023 | Casey et al. | |
| 2007/0270680 | A1 | 11/2007 | Sheffer et al. | |
| 2015/0150523 | A1 | 6/2015 | Sirpad | |
| 2016/0045317 | A1 | 2/2016 | Lang | |
| 2017/0135706 | A1 | 5/2017 | Frey et al. | |
| 2017/0143831 | A1 | 5/2017 | Varanasi et al. | |
| 2017/0220740 | A1 | 8/2017 | D'Urso | |
| 2018/0303552 | A1 | 10/2018 | Ryan | |
| 2019/0146458 | A1* | 5/2019 | Roh | G16H 30/40<br>700/98 |
| 2019/0175277 | A1 | 6/2019 | Chav | |
| 2019/0274735 | A1 | 9/2019 | Drozd et al. | |
| 2020/0078180 | A1 | 3/2020 | Casey et al. | |
| 2020/0261156 | A1* | 8/2020 | Schmidt | G06T 19/20 |
| 2021/0259776 | A1 | 8/2021 | Upadrasta et al. | |
| 2022/0000556 | A1* | 1/2022 | Casey | G16H 50/50 |
| 2022/0031396 | A1 | 2/2022 | Ryan et al. | |
| 2022/0211507 | A1 | 7/2022 | Simoes | |
| 2023/0104580 | A1 | 4/2023 | Roh et al. | |
| 2024/0115398 | A1 | 4/2024 | Frey | |
| 2024/0252248 | A1 | 8/2024 | Casey et al. | |
| 2024/0261029 | A1 | 8/2024 | Casey et al. | |

FOREIGN PATENT DOCUMENTS

| | | | |
|---|---|---|---|
| CN | 204468348 | U | 7/2015 |
| CN | 105796214 | A | 7/2016 |
| CN | 110575289 | A | 12/2019 |
| EP | 3120796 | A1 | 1/2017 |
| WO | 2014180972 | A2 | 11/2014 |
| WO | 2016172694 | A1 | 10/2016 |
| WO | 2019112917 | A1 | 6/2019 |
| WO | 2022124916 | A1 | 6/2022 |
| WO | 2024064299 | A1 | 3/2024 |

OTHER PUBLICATIONS

International Search Report and Written Opinion mailed Feb. 8, 2024 in International Patent Application No. PCT/US23/33896, 17 pages.

International Search Report and Written Opinion mailed May 30, 2024 in International Patent Application No. PCT/US24/10943, 19 pages.

International Search Report and Written Opinion mailed Jul. 5, 2024 in International Patent Application No. PCT/US24/14514, 14 pages.

Materialise Mimics, "Efficiently turn scans into accurate virtual 3D models," Retrieved on Nov. 1, 2019 at www. materialize.com/en/medical/software/mimics, 1 page.

Pimenta, Dr. Luiz, "Current Surgical Strategies to Restore Proper Sagittal Alignment," Journal of Spine 2015, vol. 4, Issue 4, 2 pages.

Pyo et al., "Methods Used to Assess the 3D Accuracy of Dental Implant Positions in Computer-Guided Implant: A Review.," Jour. of Clin. Med., vol. 8(1): 54, Issue 07, Jan. 2019, 12 pages.

* cited by examiner

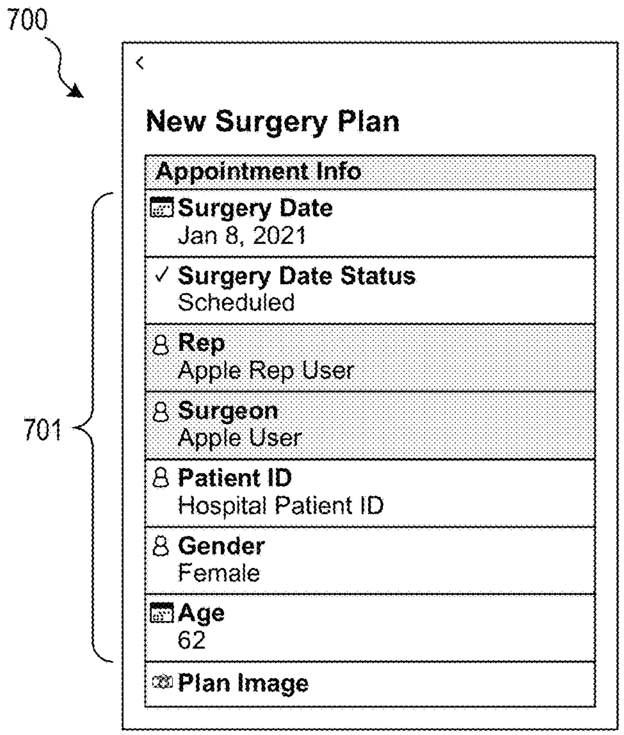

FIG. 7A

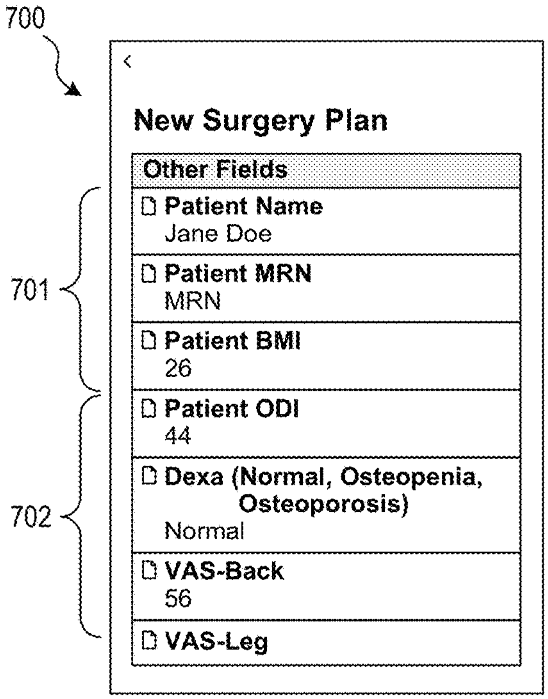

FIG. 7B

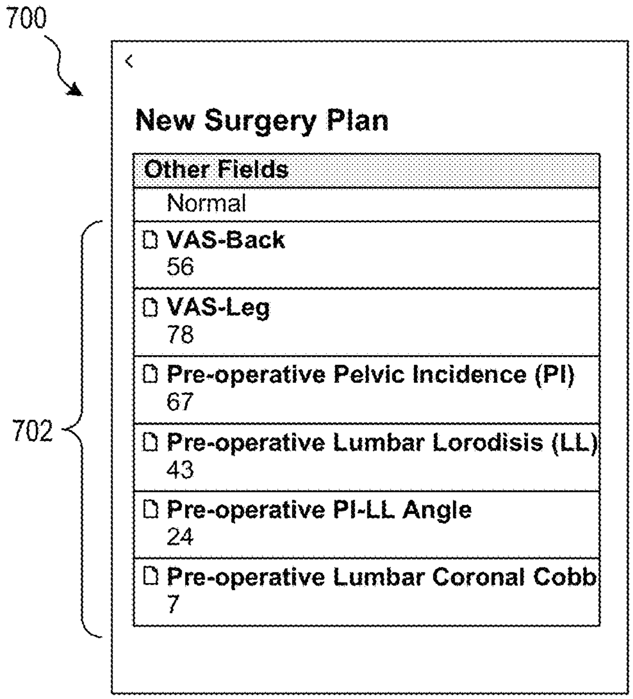

New Surgery Plan

| Appointment Info |
|---|
| 📅 Surgery Date<br>Jan 8, 2021 |
| ✓ Surgery Date Status<br>Scheduled |
| 👤 Rep<br>Apple Rep User |
| 👤 Surgeon<br>Apple User |
| 👤 Patient ID<br>Hospital Patient ID |
| 👤 Gender<br>Female |
| 📅 Age<br>62 |
| 🖼 Plan Image |

701 braces the Appointment Info fields.

700

New Surgery Plan

| Other Fields |
|---|
| ▫ Patient Name<br>Jane Doe |
| ▫ Patient MRN<br>MRN |
| ▫ Patient BMI<br>26 |
| ▫ Patient ODI<br>44 |
| ▫ Dexa (Normal, Osteopenia, Osteoporosis)<br>Normal |
| ▫ VAS-Back<br>56 |
| ▫ VAS-Leg |

701 braces Patient Name, MRN, BMI. 702 braces ODI, Dexa, VAS-Back, VAS-Leg.

700

New Surgery Plan

| Other Fields |
|---|
| Normal |
| ▫ VAS-Back<br>56 |
| ▫ VAS-Leg<br>78 |
| ▫ Pre-operative Pelvic Incidence (PI)<br>67 |
| ▫ Pre-operative Lumbar Lorodisis (LL)<br>43 |
| ▫ Pre-operative PI-LL Angle<br>24 |
| ▫ Pre-operative Lumbar Coronal Cobb<br>7 |

702 braces the fields.

Share Imaging

Patient Images

- Are you planning to upload an image study for this case?
  Yes
- If so, what type of image study is included in the upload?
  CT, X-Ray
- Please use this field to upload the image study (DCM files only).

Imaging Study

Current Stage 2011-95
Apple User
Hospital Patient ID
1/8/21

Imaging Review

703

700

1000
703
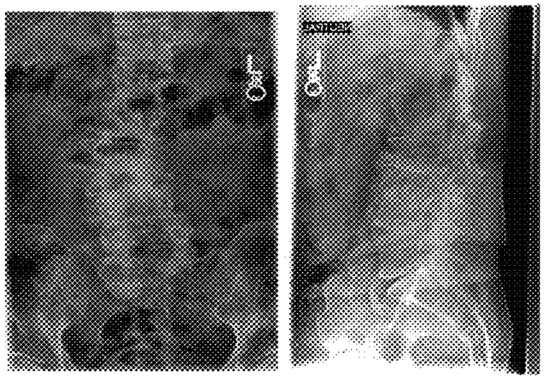
1002
| PRE-OP | | | | | |
|---|---|---|---|---|---|
| PI | 66.8° | | | | |
| LL | 42.6° | | | | |
| PI-LL | 24.2° | | | | |
| CORONAL | 7° | | | | |
| LOCAL | LEVEL | LORDOSIS | % | H-ANT (mm) | H-POST (mm) |
| | L2/3 | 1.6° | 4% | 3.0 | 0.7 |
| | L3/4 | 14.2° | 36% | 4.0 | 1.5 |
| | L4/5 | 15.2° | 39% | 5.0 | 2.8 |
| | L5/S1 | 1.3° | 3% | 2.0 | 0.3 |
1004
| PLAN | | | | | |
|---|---|---|---|---|---|
| PI | 66.8° | | | | |
| LL | 59.3° | | | | |
| PI-LL | 7.6° | | | | |
| CORONAL | 1.0° | | | | |
| LOCAL | LEVEL | LORDOSIS | % | H-ANT (mm) | H-POST (mm) |
| | L2/3 | 9.3° | 21% | 12.0 | 7.7 |
| | L3/4 | 11.6° | 26% | 15.0 | 7.9 |
| | L4/5 | 12.4° | 27% | 14.0 | 3.7 |
| | L5/S1 | 11.3° | 25% | 17.0 | 3.6 |
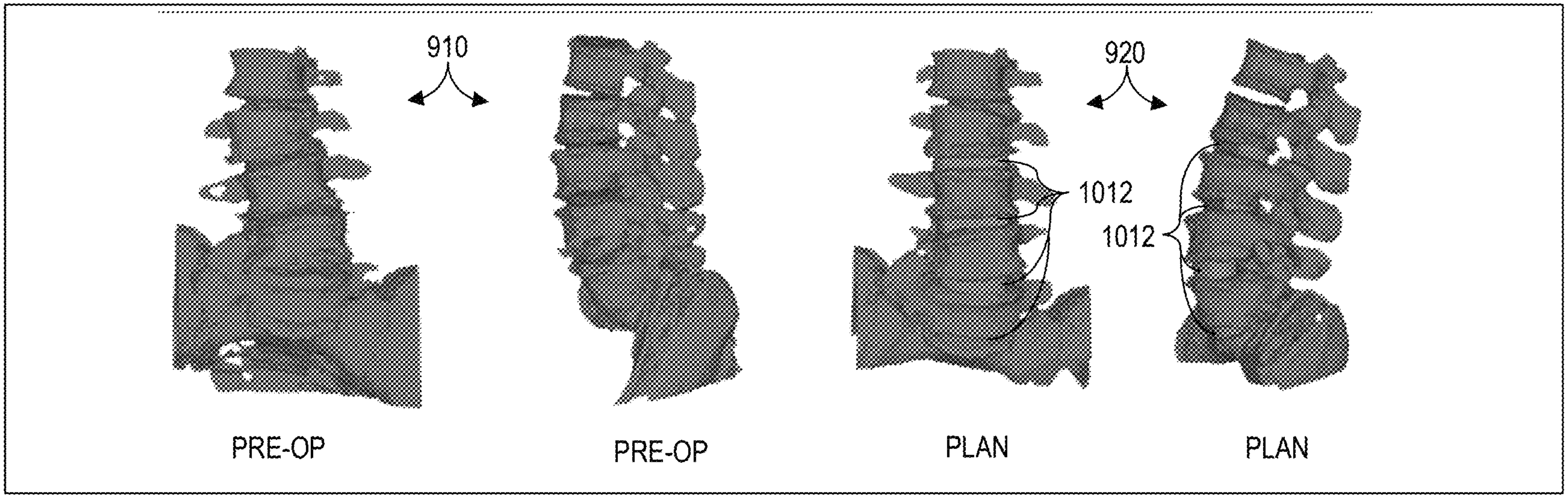
*FIG. 10*

2100

1002

| PRE-OP | | | | | |
|---|---|---|---|---|---|
| PI | 66.8° | | | | |
| LL | 42.6° | | | | |
| PI-LL | 24.2° | | | | |
| CORONAL | 7° | | | | |
| LOCAL | LEVEL | LORDOSIS | % | H-ANT (mm) | H-POST (mm) |
| | L2/3 | 1.6° | 4% | 3.0 | 0.7 |
| | L3/4 | 14.2° | 36% | 4.0 | 1.5 |
| | L4/5 | 15.2° | 39% | 5.0 | 2.8 |
| | L5/S1 | 1.3° | 3% | 2.0 | 0.3 |

1004

| PLANNED POST-OP | | | | | |
|---|---|---|---|---|---|
| PI | 66.8° | | | | |
| LL | 59.3° | | | | |
| PI-LL | 7.6° | | | | |
| CORONAL | 1.0° | | | | |
| LOCAL | LEVEL | LORDOSIS | % | H-ANT (mm) | H-POST (mm) |
| | L2/3 | 9.3° | 21% | 12.0 | 7.7 |
| | L3/4 | 11.6° | 26% | 15.0 | 7.9 |
| | L4/5 | 12.4° | 27% | 14.0 | 3.7 |
| | L5/S1 | 11.3° | 25% | 17.0 | 3.6 |

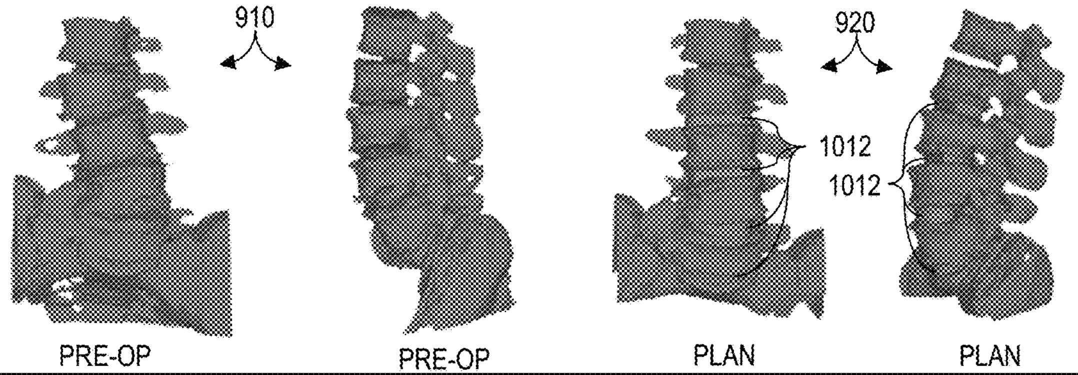

2120a

| POST ADJUSTMENT 1 | | | | | |
|---|---|---|---|---|---|
| PI | 66.8° | | | | |
| LL | 59.3° | | | | |
| PI-LL | 7.6° | | | | |
| CORONAL | 1.0° | | | | |
| LOCAL | LEVEL | LORD-OSIS | % | H-ANT (mm) | H-POST (mm) |
| | L2/3 | 9.5° | 21% | 12 | 7.7 |
| | L3/4 | 11° | 11% | 14 | 7.9 |
| | L4/5 | 12° | 27% | 14 | 3.7 |
| | L5/S1 | 11° | 25% | 15 | 3.6 |

2120b

| POST ADJUSTMENT 2 | | | | | |
|---|---|---|---|---|---|
| PI | 66.8° | | | | |
| LL | 42.6° | | | | |
| PI-LL | 24.2° | | | | |
| CORONAL | 7° | | | | |
| LOCAL | LEVEL | LORD-OSIS | % | H-ANT (mm) | H-POST (mm) |
| | L2/3 | 10° | 21% | 12.0 | 7.7 |
| | L3/4 | 11° | 26% | 15.0 | 7.9 |
| | L4/5 | 14° | 27% | 14.0 | 3.7 |
| | L5/S1 | 12° | 25% | 17.0 | 3.6 |

2120c

| POST ADJUSTMENT 2 | | | | | |
|---|---|---|---|---|---|
| PI | 66.8° | | | | |
| LL | 42.6° | | | | |
| PI-LL | 24.2° | | | | |
| CORONAL | 7° | | | | |
| LOCAL | LEVEL | LORD-OSIS | % | H-ANT (mm) | H-POST (mm) |
| | L2/3 | 9.3° | 21% | 11 | 7.6 |
| | L3/4 | 11.6° | 26% | 14 | 7.8 |
| | L4/5 | 12.4° | 27% | 13 | 3.6 |
| | L5/S1 | 11.3° | 25% | 16 | 3.7 |

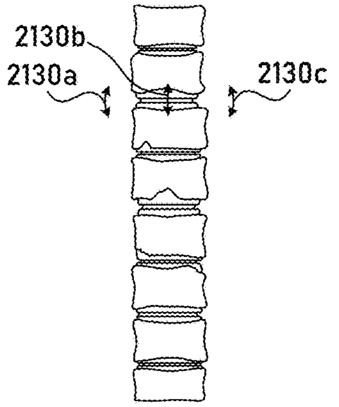

Adjustment 1

APPROVE MODIFY

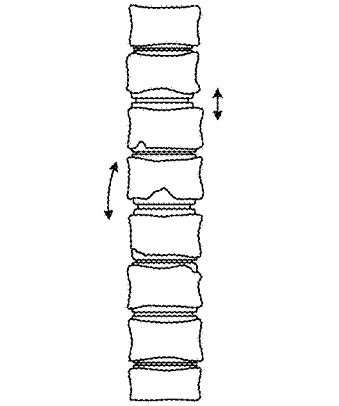

Adjustment 2

APPROVE MODIFY

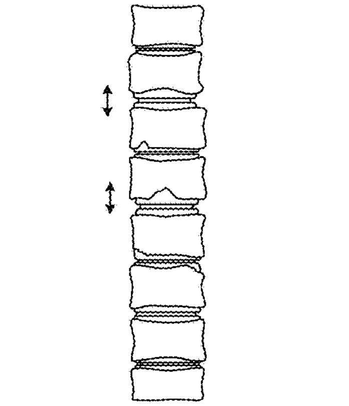

Adjustment 3

APPROVE MODIFY

SYSTEM FOR MODELING PATIENT SPINAL CHANGES

CROSS-REFERENCE TO RELATED APPLICATION

This application claims priority to U.S. Provisional Application No. 63/437,975, filed Jan. 9, 2023, which is hereby incorporated by reference in its entirety.

TECHNICAL FIELD

The present disclosure is generally related to medical devices, and more particularly to systems and methods for modeling anatomical changes in a patient after installation of a patient-specific implant.

BACKGROUND

Orthopedic implants are used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery itself may encompass a variety of procedures and targets, such as one or more of the cervical spine, thoracic spine, lumbar spine, or sacrum, and may be performed to treat a deformity or degeneration of the spine and/or related back pain, leg pain, or other body pain. Common spinal deformities that may be treated using an orthopedic implant include irregular spinal curvature such as scoliosis, lordosis, or kyphosis (hyper- or hypo-), and irregular spinal displacement (e.g., spondylolisthesis). Other spinal disorders that can be treated using an orthopedic implant include osteoarthritis, lumbar degenerative disc disease or cervical degenerative disc disease, lumbar spinal stenosis, and cervical spinal stenosis. Unfortunately, conventional orthopedic implants, such as intervertebral discs and fixation rods, do not actively work together to provide post-operative real-time adjustments and corrections.

In addition, numerous types of data associated with patient treatments and surgical interventions are available. To determine treatment protocols for a patient, physicians often rely on a subset of patient data available via the patient's medical record and historical outcome data. However, the amount of patient data and historical data may be limited, and the available data may not be correlated or relevant to the particular patient to be treated. Additionally, although digital data collection and processing power have improved, the collection mechanisms tend to be limited to one physiological trait and/or one disease/condition. For example, conventional technologies in the field of orthopedics may be limited to a limited set of devices and unable to utilize other patient data or pre-treatment data. Additionally, such data may not be used by conventional implanted devices, which may also be unable to communicate with each other to coordinate their operation based on current disease state/condition. Thus, conventional technologies are limited in collecting data and generating and optimizing patient-specific treatments (e.g., surgical interventions and/or implant designs) to achieve favorable treatment outcomes.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIGS. 7A-7D illustrate an exemplary patient data set that may be used and/or generated in connection with the methods described herein, according to an embodiment.

FIGS. 9A-1-9B-2 illustrate an exemplary virtual model of a patient's spine in a pre-operative anatomical configuration and a corrected anatomical configuration. More specifically, FIGS. 9A-1 and 9A-2 illustrate the pre-operative anatomical configuration of the patient; and FIGS. 9B-1 and 9B-2 illustrate the corrected anatomical configuration.

FIG. 10 illustrates an exemplary surgical plan for a patient-specific surgical procedure that may be used and/or generated in connection with the methods described herein, according to an embodiment.

FIG. 15 illustrates an exemplary corrective plan that may be used and/or generated in connection with the systems and methods described herein, according to an embodiment.

DETAILED DESCRIPTION

Figure 1:
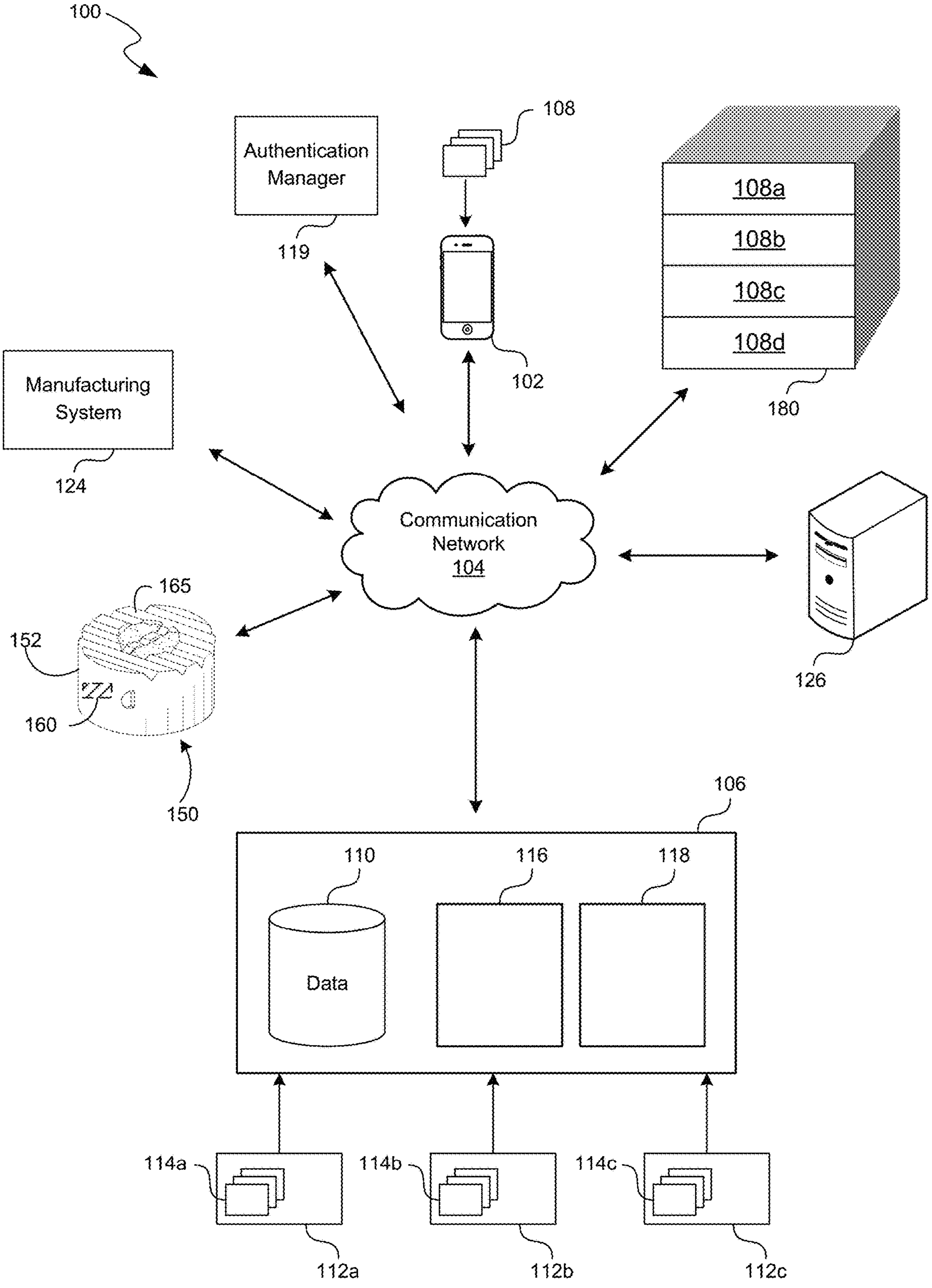
FIG. 1 is a network connection diagram illustrating a system for providing patient-specific medical care, according to one or more embodiments of the present technology.

The present technology is directed to systems and methods for modeling anatomical changes in a patient after installation of a patient-specific artificial implant. In the context of orthopedic surgery, systems with improved computing capabilities (e.g., predictive analytics, machine learning, neural networks, artificial intelligence (AI)) can use large data sets to define improved or optimal implant designs for a specific patient. The present technology can model changes to one part of a spinal column of a patient's backbone based on changes to another part of the spinal column. The present technology can calculate and display one or more reciprocal changes to nearby anatomy due to anatomy corrections. For example, when the lumbar spine is corrected to a desired configuration by a patient-specific implant, other spinal level(s) or region(s) (e.g., cervical, thoracic, sacrum, coccyx, etc.) can be affected. The present technology can model the anatomical changes to provide predictions of the impact of corrections to the lumbar spine and how the thoracic and/or cervical spines are impacted. Different sections of the vertebral column can be analyzed as individual anatomical structures. For example, the present technology models the thoracic spine as a singular anatomical structure so that changes (e.g., vertebral alignment, curvature, etc.) to the lumbar spine can impact the position (including curvature) of the thoracic spine.

The present technology can assess the impact of local anatomical correction(s) on global conditions (alignment, pain, debilitation, etc.) of the patient's anatomy. The present technology can, for example, model (e.g., in 2D or 3D) how a spinal deformity or degeneration causes a reduction in functional activities, increased debilitation, and/or pain. The present technology can model progression of how deformity or degeneration over time. For example, as degeneration occurs the patient may experience function impairment and, in some instances, become physically disabled.

The present technology can collect information (e.g., measurements, feedback, pre-operative data, etc.) about the patient conditions to determine pain, mobility, debilitation, deformity, and/or degeneration scores for the patient. For example, a patient can rate (e.g., levels 1-10) their pain level, mobility, and/or discomfort in a pain questionnaire on a device. The present technology can assess how a correction to the patient's spinal column will impact the patient's conditions. For example, mobility, pain, debilitation, and degeneration are related for the patient. The present technology can model how a corrected spinal feature of a patient-specific implant can reduce pain, increase mobility, reduce debilitation, and/or reposition anatomy.

The present technology can characterize and compare patient's data (e.g., entire data or subset of data) to aggregated data from groups of prior patients (e.g., parameters, metrics, biomechanics data, pathologies, treatments, outcomes). In some embodiments, the systems described herein use this aggregated data to formulate potential treatment solutions (e.g., surgical plans and/or artificial implant designs for spine and orthopedic procedures) and analyze the associated likelihood of success. These systems can further compare potential treatment solutions to determine an optimal patient-specific solution that is expected to maximize the likelihood for a successful outcome.

In some embodiments, the present technology can predict, model, or simulate post-operative anatomical changes and/or disease progression of a particular patient to aid in diagnosis and/or treatment planning. The simulation can model and/or estimate future anatomical configurations and/or spine metrics of the patient (a) if no surgical intervention occurs, or (b) for a variety of different surgical intervention options. The progression modeling can thus be used to determine the optimal time for surgical intervention and/or to select which surgical intervention provides the best near-term and/or long-term outcomes. In some embodiments, post-operative outcome and/or disease progression modelling is performed using one or more machine learning models trained based on a plurality of reference patients.

At least some embodiments of the systems described herein can use aggregated data to formulate implant inspection protocols, implant quality criteria, and/or manufacturing plans or parameters. The system can identify anatomical changes for additional review, including human review and/or automated review (e.g., machine learning review), and can modify surgical plans, implant designs, and other technology disclosed herein based on the additional review. This provides different levels of anatomical analysis (e.g., static analysis, dynamic analysis, tissue analysis, patient mobility/functionality analysis, etc.) and implant design to increase the likelihood of predicted outcomes.

For example, if a patient presents with a spinal condition that can be described with data including lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.), pelvic parameters, nerve tissue compression parameters (e.g., level and location of nerve tissue compression), stenosis parameters, and/or other data describing the spinal column and surrounding anatomical structures. An algorithm using these data points as inputs can be used to describe an optimal implant design to correct the subject pathology and improve the patient's outcome. As additional data inputs are used to describe the pathology (e.g., disc height, segment flexibility, bone quality, rotational displacement, nerve tissue compression, soft tissue condition, etc.), the algorithm can use these additional inputs to further define an optimal implant design for that particular patient and their pathology. Intra-spine and inter-spine correlations between spinal elements (e.g., vertebrae, such as cervical spine (C1-C7), thoracic spine (T1-T12), lumbar spine (L1-L5), sacral spine (S1-S5), and the tailbone) can be used in predictions. Intra-spine corrections can be between vertebrae of the cervical spine, vertebrae of the thoracic spine, or vertebrae of the lumbar spine. Inter-spine correlations can be between vertebrae of the cervical and thoracic spines, vertebrae of the lumbar spine and cervical/thoracic spines, etc. Machine learning algorithms can be used to identify these correlations.

At least some embodiments of the systems described herein can generate implant data (e.g., design files, fabrication instructions, etc.) for manufacturing implants. The system can manage access to the implant data based on authentication levels. The authentication levels can include, without limitation, authenticating a user (e.g., manufacturer, healthcare provider, etc.) based on geolocation, biometric data, blockchain access, tokens, or any authentication method. Based on the determined authentication level of the user requesting access to the implant data, the system can permit the user to access some or all of the implant data. The system can include one or more healthcare digital filing cabinets that store implant data, patient information, electronic medical records, and/or additional patient related information. In some embodiments, systems can share data (e.g., implant data, healthcare data, patient information, electronic medical records, and/or additional patient related information) via a network without using digital filing cabinets. The digital filing cabinets can use blockchain and non-fungible token (NFT) technology to control collection and access to the implant data.

In some implementations, machine learning is utilized to model anatomical changes in a patient after installation of a patient-specific implant. Intra-operative data and/or post-operative data can be used to further train machine learning models. For example, the machine learning can be retrained with anatomical change data based on the outcome of an implant installation surgery. The computer-implemented method can further include receiving patient data for designing an implant, manufacturing an implant, installing an implant in a patient, etc. The received patient data can be analyzed to identify a relevant training parameter. A reference data set can be generated based on the relevant training parameter. The machine learning models can be trained based at least in part on the reference data set for inspecting patient data to model anatomical changes in a patient similar to the patient data related to a patient-specific implant procedure. In some embodiments, the relevant training parameter can be a categorized spinal condition, wherein the categorization is based on one or more predetermined thresholds. The predetermined thresholds can include, without limitation, a threshold quality, a threshold level-specific lumbar lordosis, a threshold Cobb angle, a threshold pelvic incidence, and/or a threshold disc height. In some embodiments, the received patient data includes at least one of comparing the received patient data to patient data with modeled anatomical changes in a patient after installation of a patient-specific implant of a patient. Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words “comprising,” “having,” “containing,” and “including,” and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms “a,” “an,” and “the” include plural references unless the context clearly dictates otherwise.

Although the disclosure herein primarily describes systems and methods for verifying the quality of patient-specific implants, the technology may be applied equally to medical treatment and devices in other fields (e.g., other types of medical practices). Additionally, although many embodiments herein describe systems and methods with respect to implanted devices, the technology may be applied equally to other types of medical technologies and devices (e.g., non-implanted devices).

FIG. 1 is a network connection diagram illustrating a computing system 100 for providing patient-specific medical care, according to one or more embodiments of the present technology. As described in further detail herein, the system 100 is configured to collect, store, monitor, and/or update healthcare data. System 100 can include one or more digital filing cabinets 180 that can contain, without limitation, one or more electronic health records (EHRs), EMRs, patient information, digital wallets (e.g., tokens, credit cards, crypto currency, payment information, etc.), and other healthcare data. The digital filing cabinet 180 can receive and convert the healthcare data into a digital format to increase efficiency of locating and retrieving healthcare data. The digital filing cabinet 180 can receive the healthcare data from a patient, healthcare provider(s), medical insurance entities, banking entities, imaging centers, and/or storage devices with healthcare data. Based on the type of healthcare data, the digital filing cabinet 180 can organize the healthcare data by authentication levels. For example, the patient can access all the healthcare data, but the healthcare provider is limited to medical records and cannot access the patient’s medical insurance or payment information. The digital filing cabinet 180 contains the patient healthcare data 108 and organizes the patient healthcare data by different authentication levels, such as data 108*a*, 108*b*, 108*c*, and 108*d*. Each group or set of healthcare data 108*a*, 108*b*, 108*c*, and 108*d* requires a different level of authentication for a user to access. Example healthcare datasets and healthcare data are discussed in connection with FIGS. 8-11. Once the authentication level of a user is identified, the system 100 can send the healthcare data associated with the identified authentication level to the user. In some implementations, the system 100 sends the healthcare data to the patient’s implant 150 for the user to retrieve or to a user device.

The number of groups of healthcare data, permission settings, stored data, organizational scheme, and/or other configurations can be set by the user, healthcare provider, or the like. Data can be automatically collected and incorporated into the appropriate group of data. In cloud-based implementations, the digital filing cabinet 180 can be stored on a cloud server to provide remote access. In some implementations, the digital filing cabinet 180 can be stored locally to provide access to records at any time. Additionally, local storage of the digital filing cabinets 180 with digital wallets containing blockchain information can be stored locally. Each group of healthcare data 108*a*, 108*b*, 108*c*, and 108*d* can be associated by the user (or data management system) with, for example, a procedure, a physician, a healthcare provider, and/or medical manufacture. The user can add information, including annotation, personal notes, and other information that may or may not be viewable by other users, to the healthcare data 108*a*, 108*b*, 108*c* and 108*d* and can select the type, amount, and/or level of authorization/access.

In some embodiments, a group of healthcare data 108*a* can be associated with an implant 150 in the patient (not shown) and can include a surgical plan for the implant 150, manufacturing data for the implant 150, notifications (e.g., recall notifications), predicted post-treatment analytics, physician information, and other information (e.g., pre-operative, intra-operative, and/or post-operative information) associated with the implant 150 or procedure. The user can set one or more rules for allowing authorized user(s) to access (e.g., all or a portion of) the healthcare data 108*a* or healthcare data 108. For example, the user can authorize viewing of post-operative data 108*a* by a physical therapist who can access post-operative collected data to modify therapy plans for the user. The user can authorize a primary care physician access to the healthcare data 108 to provide general healthcare treatment and can authorize a surgeon access to the healthcare data 108*a* to evaluate surgical outcomes and recommend additional treatments, such as future surgical interventions.

The healthcare data 108*b* can include, for example, general electronic medical records (EMRs) of the patient, including health records not associated with the implant. The user can authorize a primary care physician access to the healthcare data 108*b* to provide general healthcare treatment. The user can authorize family members and third parties access to the healthcare data 108*b*. Accordingly, the access settings for the healthcare data 108*a*, 108*b* can be the same or different.

The healthcare data 108*c* can include, for example, data from a user device input. The data can be from, for example, wearables (e.g., smartwatches, pedometers, etc.), smartphones, biometric sensors (e.g., analyte sensors, glucose sensors, etc.), heart monitors, exercise monitoring equipment, or the like. The user can authorize family members to access the data 108*c* to help with compliance with, for example, dietary goals, exercise goals, or other user goals.

Data can be automatically provided to the digital filing cabinet 180. In some embodiments, for example, an implant retrieval feature 160 can provide instructions for accessing the digital filing cabinet 180. An imaging apparatus (e.g., an MRI machine, x-ray machine, scanner, etc.) can read information from the retrieval feature 160. The information can be transmitted, via communication network 104, to the digital filing cabinet 180. The transmitted information can include, without limitation, authorization information (e.g., digital filing cabinet login information), patient identification, implant identifier, patient imaging, and/or other information to use to authorize, locate, and/or categorize data.

The digital filing cabinet 180 can store data transmitted, via the communication network 104, from manufacturing system 124 and can analyze received data and correlate the data, such as manufacturing data, with the received implant data. Correlation settings can be modified or set by the user. Additionally, surgical plans can be transmitted, via the communication network 104, from an implant design platform or system 106 ("system 106") to the digital filing cabinet 180. The surgical plan can be associated with the manufacturing data, implant data, and other information associated with the implant 150. The digital filing cabinet 180 can send, via the communication network 104, patient healthcare data to the system 106. This allows newly available data to be automatically or periodically transmitted to the analysis system 106. The analysis system 106 can analyze the newly received data using, for example, one or more models to provide analytics to the client computing device 102, digital filing cabinet 180, manufacturing system 124, physician, etc. The client computing device 102 can receive analytics and notifications from, for example, the digital filing cabinet 180, analysis system 106, and/or other data source.

In some embodiments, the system 100 is configured to manage patient healthcare data on user devices, cloud-based devices, and/or healthcare provider devices. The healthcare data can include patient medical records, medical insurance information, health metrics from wearable devices, surgical information, surgical plans, technology recommendations (e.g., device and/or instrument recommendations), and/or medical device information (e.g., an implanted medical device (also referred to herein as an "implant" or "implanted device") or implant delivery instrument). The digital wallet can be used to manage blockchain healthcare data (e.g., blockchain EHRs, EMRs, etc.), insurance actions (e.g., payments, claim submissions, etc.), or the like.

In some embodiments, the system 100 manages the authentication required to access the medical records. The authentication can include blockchain, tokens, keys, biometrics, geolocation, passwords, or any authentication credentials. Healthcare data that is particular to a patient, is referred to herein as a "patient-specific" or "personalized" healthcare data. The digital filing cabinet 180 can store one or more keys (e.g., private keys, public keys, etc.), authentication information, and/or other information for accessing data, including electronic medical records associated with a patient from a distributed blockchain ledger of electronic medical records. U.S. application Ser. No. 17/463,054 discloses systems and methods for tracking patient medical records using, for example, keys and is incorporated by reference in its entirety. The system 100 can include systems and features for linking medical devices with patient data as disclosed in U.S. patent Ser. No. 16/990,810, which is incorporated by reference in its entirety. Digital filing cabinets can be used to receive user feedback as described in U.S. application Ser. No. 16/699,447, which is incorporated by reference in its entirety. The system disclosed herein can include digital filing cabinets for designing medical devices using the methods disclosed in U.S. application Ser. No. 16/699,447.

The system 100 includes a client computing device 102, which can be a user device, such as a smartphone, mobile device, laptop, desktop, personal computer, tablet, phablet, wearable device (e.g., smartwatch), or other such devices known in the art. As discussed further herein, the client computing device 102 can include one or more processors, and memory storing instructions executable by the one or more processors to perform the methods described herein. The client computing device 102 can be associated with a healthcare provider or a patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive patient healthcare data 108 associated with a patient. The patient healthcare data 108 can include data representative of the patient's condition, anatomy, pathology, medical history, preferences, and/or any other information or parameters relevant to the patient. For example, the patient healthcare data 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, x-ray images), diagnostic equipment information (e.g., manufacturer, model number, specifications, user-selected settings/configurations, etc.), or the like. In some embodiments, the patient healthcare data 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. In some embodiments, the client computing device 102 can locally store the digital filing cabinet 180, healthcare data 108, and/or other information. The client computing device 102 can store account information for allowing the user to automatically access remote digital filing cabinets or accounts with or without login credentials. In some embodiments, the client computing device 102 can periodically or continuously receive newly available data (e.g., biometrics from wearables, user input, etc.) and can transmit all of or a portion of the newly available data to, for example, remote storage systems, such as the digital filing cabinet 180, server 106, or the like.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "healthcare data network" or "healthcare data analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The cloud analytics integration platform 126 is connected to the communication network 104. The analytics integration platform 126 can analyze the healthcare data and integrate data collected from the patient and healthcare providers into digital filing cabinet. The analytics integration platform 126 can integrate surgical plans and patient plan, identify health metrics of concern for the patient, display patient information and goals, perform post-operative analytics, and generation of healthcare provider or patient notifications (e.g., monitoring based on data from wearables, requesting updated information, scheduling appointment, or notifying of emergencies).

The medical implant 150 can be an intervertebral device that includes a body 152 configured to interface with one or more identified anatomical structures (e.g., one or more vertebral bodies or endplates) at and/or proximate the target implantation site (e.g., between one or more vertebral bodies or endplates). The implant body 152 can include one or more structural features designed to engage one or more identified anatomical structures. For example, in the illustrated embodiment, the implant 150 can include an upper surface 165 and a lower surface (not shown) configured to seat against vertebral bodies of spine. In some embodiments, the upper surface 165 and the lower surface can have contours that match contours of the vertebral endplates, such that the upper surface 165 and lower surface "mate" with the corresponding vertebral endplates they engage with. The dimensions, contours, topology, composition, and/or other implant data can be part of the EMR. In some embodiments, such as the illustrated embodiment, the upper surface 165 and/or the lower surface can be textured (e.g., via roughenings, knurlings, ridges, and the like). Texturing data can be part of the manufacturing data stored in the EMRs. For lordotic correction, the upper surface 165 and the lower surface may be angled with respect to one another, and the EMR can include the angle and sizes of these surfaces.

A user (e.g., a physician, healthcare provider, patient, etc.) can access EMRs using a retrieval feature 160. For example, in embodiments in which the retrieval feature 160 is a bar code corresponding to the unique identifier, the user can scan the retrieval feature 160 using, for example, one or more cameras on the computing device and/or otherwise input the unique identifier into the computing device. Once the unique identifier is inputted into the computing system, the computing system can send the unique identifier to a remote server (e.g., via a communication network) with a request to provide the corresponding patient-specific healthcare data set. In response to the request, and as described above, the server can locate the specific data set associated with the unique identifier and transmit the data set to the computing device for display to the user. The implant 150 can include other features assisting with accessing the ledger and viewing the EMRs.

The retrieval feature 160 can be used to carry patient data, such as a private key for unlocking patient medical records stored on a blockchain ledger. The medical implant 150 can be blockchain-enabled to establish communicative contact using a proximity communication mode. A private key stored on the retrieval feature 160 can be used to access the patient-specific healthcare data. In some implementations, the medical implant 150 also contains a private blockchain ledger for tracking EMRs associated with the patient. As the patient undergoes various treatments, new EMRs and updates to existing EMRs for the patient are generated and stored as "transactions" in a blockchain ledger. To access the EMRs associated with the patient, the private key from the medical implant 150 must be used to "unlock" the EMRs stored in the blockchain ledger. The patient can provide this private key to healthcare providers and other interested parties by a secure platform, mobile application, digital key, or the like. In some embodiments, the EMRs are encrypted using an encryption key that the healthcare provider decrypts. Additionally or alternatively, re-keying protocols, certification management protocols (e.g., enrollment certification protocol, transaction certification protocol, etc.), and other protocols and can be utilized for variable access and permissions. The patient can manage the data of the EMR to share selected data only. For example, the patient can a keep section of the EMR private while sharing another section of the EMR. The system also allows for user-controlled settings, such as settings for minors, family members, relatives, and/or other user-controlled settings.

An EMR can include patient data associated with the implant design and design process. If the implant is an artificial disc, for example, the stored data can include kinematic data (e.g., pre-operative patient data, target kinematic data, etc.), manufacturing data, design parameters, target service life data, physician recommendations/notes, etc. The disc can include an articulating implant body with plates contoured to match vertebral endplates, custom articulating members between the plates for providing patient-specific motion, etc. If the implant is an intervertebral cage, the stored data can include materials specifications of the implant body, dimensions of the implant body, manufacturing data, design parameters, target service life data, physician recommendations/notes, etc. The applications and patents incorporated by reference disclose data (e.g., surgical plans, implant specifications, data sets, etc.) that can be associated with the retrieval feature 160.

In some implementations, the patient can set variable permissions for access to transactions and details stored in the blockchain ledger. For example, particular medical providers may only be given access to certain transactions related to particular kinds of medical procedures. In other implementations, permissions can be set based on the patient, such as having child settings for children with an implant.

The medical implant 150 can also track and monitor various health related data for the patient. For example, the medical implant 150 can include one or more sensors configured to measure pressures, loads, or forces applied by anatomical elements to monitor, for example, activity, loading, etc. The medical implant 150 can continuously or periodically collect data indicating activity level, activities performed, disease progression, or the like. For example, loading across the implant 150 can be tracked over period of time. The applications and patents incorporated by reference disclose techniques for monitoring, collecting data, and transmitting data. In some embodiments, the medical implant 150 can identify events, such as excess loading, imbalance of the spine, or the like. In some embodiments, the patient is monitored with automatic blockchain updating based on activity (e.g., surgical procedure, change in status, etc.), disability (e.g., new disability, progression of disability, etc.), and/or healthcare events. The healthcare events can include imaging, diagnosis, treatment, and/or outcomes and event data that can be encoded in the blockchain. Collected data can be used as historical patient data used to treat another patient. The applications and patents incorporated by reference also disclose usage of historical data, imaging data, surgical plans, simulations, modeled outcomes, treatment protocols, and outcome values that can be encoded in the blockchain. The digital filing cabinets can also track and monitor various health related data for the patient and can include one or more blockchain digital wallets for managing blockchain data. The number, configuration, and/or contents of digital wallets can be selected by the user, physician, etc. The digital wallet can be used to access blockchains to automatically update blockchains for any number of implants.

In some implementations, two or more implants can be used. For example, a patient can have both a spinal implant with an encoded chip containing the private key and/or the private blockchain ledger containing the EMRs of the patient and a subcutaneous digital implant. The subcutaneous digital implant acts as an intermediary device, communicating with both the spinal implant containing the private key and/or the private blockchain ledger and an external computing device, such as a patient treatment computing system. The subcutaneous digital implant may also include data of its own, such as patient identifying information, biometric data, and the like. In some embodiments, the subcutaneous digital implant may include the private key and/or the private blockchain ledger containing the EMRs of the patient.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like.

A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.).

Additional implant types, configurations, and structural features suitable for engaging identified anatomical features are described, for example, in U.S. application Ser. No. 16/207,116, filed Dec. 1, 2018, and U.S. application Ser. No. 16/987,113, filed Aug. 6, 2020, the disclosures of which are incorporated by reference herein in their entireties. For example, the medical implants can be pedicle screws, patient-specific implants, interbody implant systems, artificial discs, expandable intervertebral implants, sacroiliac implants, plates, arthroplasty devices for orthopedic joints, non-structural implants, or other devices disclosed in the patents and applications incorporated herein by reference.

The medical implant 150 can be used to track and monitor medical data associated with the patient. U.S. Application No. 63/218,190 discloses implants capable of collecting data, assigning weighting/values, and communicating with other devices. The monitoring can be used with prescriptive systems, such as the systems disclosed in U.S. Pat. No. 10,902,944 and U.S. application Ser. No. 17/342,439, which are incorporated by reference in their entireties. For example, the patient's data can be incorporated into one or more training sets for a machine learning system or other systems disclosed in the incorporated by reference patents and applications. The medical implant 150 can also be a multipurpose implant, providing structure to address a medical issue in the body of the patient while also carrying information regarding the patient. For example, the medical implant 150 can be a pacemaker, a plate or pin to correctly position a previously broken bone or set of bones, and the like. The digital filing cabinet 180 can also be incorporated into the systems disclosed in U.S. Pat. No. 10,902,944 and U.S. application Ser. No. 17/342,439 to track and monitor patient-managed medical data.

The client computing device 102 and server 106 can individually or collectively perform the various methods described herein for storing and retrieving healthcare data. For example, some or all of the steps of the methods described herein can be performed by the client computing device 102 alone, the server 106 alone, or a combination of the client computing device 102 and the server 106. In some embodiments, the client computing device 102 includes one or more digital filing cabinets 180. Thus, although certain operations are described herein with respect to the server 106, it shall be appreciated that these operations can also be performed by the client computing device 102, and vice-versa.

The server 106 includes at least one database 110 configured to store reference data useful for the providing, managing, or analyzing patient-specific healthcare data from an implant methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the healthcare data 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112*a*-112*c*, collectively 112), digital filing cabinets, or combinations thereof. The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114*a*-114*c*, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116 and a treatment planning module 118. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. The database 110 can retrieve or receive data from the client computing device 102, digital filing cabinet 180, or other data source. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The reference data can be updated in real-time or almost real-time using other patient data accessible via the network 104. The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular healthcare provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one treatment plan or recovery protocol (e.g., pre-operative plans, surgical plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output and actual output following treatment.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

The system can analyze the design and/or virtual model(s) (e.g., models of implants, anatomical models, etc.) to determine one or more geometric/shape deviations as compared to a reference implant, predicted post-operative metrics outside an acceptable range, etc. In some embodiments, the system 100 identifies non-conformities for analysis. The criteria for identifying non-conformities can be inputted by a user, generated based on patient data and/or surgical plan, or the like. In response to identifying a non-conforming feature meets a non-conformity risk threshold, the system 100 can generate a non-conformity report for the implant design, predicted anatomical outcome, manufacturing implant, etc. Non-conformity reports can be generated at different times during the design and/or manufacturing process and can include virtual model data for viewing fitting of a virtual model of the implant with one or more anatomical features of the patient. Non-conformity reports can also be generated for instruments or other items disclosed herein.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the digital filing cabinet 180 and/or client computing device 102 for output to a user (e.g., clinician, surgeon, healthcare provider, patient). In some embodiments, the client computing device 102 includes or is operably coupled to a display for outputting the treatment plan(s). The display can include a graphical user interface (GUI) for visually depicting various aspects of the treatment plan(s). For example, the display can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display can show a design for a medical device to be implanted in the patient, such as a two- or three-dimensional model of the device design. The display can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, the medical device design(s) generated by the treatment planning module 118 can be transmitted from the client computing device 102 and/or server 106 to a manufacturing system 124 for manufacturing an implant or a corresponding medical device. The manufacturing system 124 can be located on site or off site. The implant may be manufactured by any suitable manufacturing system (e.g., the manufacturing system 124 shown in FIG. 1). The digital filing cabinet 180 can store the generated medical device design(s), manufacturing data (e.g., CAM data, print data, etc.), manufacturing information, data for generating surgical plans, surgical plans, surgical plan reports, post-operative data (e.g., therapy plans, predicted outcomes, etc.), and/or other information associated with the medical device.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, waterjet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

Following the treatment of the patient in accordance with the treatment plan, treatment progress can be monitored over one or more time periods to update the data analysis module 116 and/or treatment planning module 118. Post-treatment data can be added to the reference data stored in the database 110 and used for post-operative analytics. The post-treatment data can be used to train machine learning models for developing patient-specific treatment plans, patient-specific medical devices, or combinations thereof.

The system 100 can generate implant data (e.g., design files, fabrication instructions, etc.) for manufacturing an implant (e.g., implant 150). The system 100 can manage access to the implant data based on authentication levels. The authentication levels can include, without limitation, authenticating a user (e.g., manufacturer, healthcare provider, etc.) based on geolocation, biometric data, blockchain access, tokens, or any authentication method. Based on the determined authentication level of the user requesting access to the implant data, the system can permit the user to access some or all of the implant data. The system 100 can include one or more healthcare digital filing cabinets (e.g., digital filing cabinet 180) that store implant data, patient information, electronic medical records, and/or additional patient related information. In some embodiments, systems can share data (e.g., implant data, healthcare data, patient information, electronic medical records, and/or additional patient related information) via a network without using digital filing cabinets. The digital filing cabinets can use blockchain and non-fungible token (NFT) technology to control collection and access to the implant data.

In some embodiments, the system 100 generates one or more models (e.g., biomechanical models, dynamical models, static models, functional mobility simulations, etc.) of anatomical effects that are predicted after installation of a patient-specific implant. The models can illustrate how the changes to one section of the spinal anatomy can impact other section(s) of the spinal anatomy. For example, system 100 can generate a model of the anatomical changes in a patient to provide predictions of how corrections to the lumbar spine impact the thoracic and cervical spines. In some embodiments, the present technology models the thoracic spine as a singular anatomical structure so that changes to the lumbar spine can impact the position of the thoracic spine. System 100 can assess the impact of local corrections on global conditions/features (e.g., alignment, pain, debilitation, mobility, etc.) of the patient. For example, the models can illustrate how a spinal deformity or degeneration causes a reduction in functional activities, increased debilitation, and increased pain. The model can predict how a correction to the spinal deformity with an implant installation can cause an increase in functional activities, decreased debilitation, and decreased pain for a patient. The system 100 can generate a model of the anatomical changes in a patient to provide predictions of how corrections to the thoracic spine impact the cervical spine or lumbar spine. The system can further determine remote or far surgical steps to compensate for adverse effects to the cervical spine or lumbar spine. Additionally, the anatomical changes can also include effects to anatomical elements near to or surrounding the spine. The anatomical elements can include, without limitation, vertebra, spinal cord, nerves (or nerve tissue), ligaments, muscles, soft tissue, or the like.

The system 100 can model changes to tissues in regions away from (e.g., beyond a threshold distance) the surgical site or surgical target. The tissues can be bony structures, non-bony structures, soft tissue, or the like. For example, the system 100 can predict whether an intervention at the lumbar level will likely impact function (e.g., musculature function, nerve function, etc.) at thoracic or cervical levels. The modeling can include, without limitation, static modeling, dynamic modeling, kinematics, multi-tissue modeling (e.g., modeling of bony tissue, cartilage, connective tissue, muscles, etc.), equation of motion modeling, recovery modeling (e.g., fusion rates, nerve tissue healing, soft tissue recovery, etc.), or the like. Simulations can be performed using two dimensional models, three dimensional models, or other types of suitable models.

The system 100 can automatically check for adverse far or remote anatomical effects ("far anatomical effects") induced in other levels not included in virtual modelling (e.g., virtual modelling reviewed by a physician or surgical team). The far anatomical effects can include, without limitation, bony misalignment, nerve compression, or other adverse effects in regions away (e.g., two or more levels away from surgically altered vertebrae in spinal procedures) from the surgical target. For example, surgical reports may not include images or models with far anatomical effects. If an adverse far anatomical effect is identified, the system 100 can generate images or models that include those effect(s) for user review. Those effect(s) can be incorporated into surgical reports to assist with comprehensive treatment analysis and planning. Adverse far anatomical effects can be permanent post-operative effects (e.g., spinal misalignment, excess loading on bony tissue, poor posture, abnormal muscular function, etc.) measurably impact the treatment outcome. Multiple anatomical structures (e.g., multiple vertebrae, organs, etc.) can separate the surgical site and locations of the adverse far anatomical effects.

The system 100 can provide an alert (e.g., via an alert window in a surgical plan, messaging, etc.) if there is risk the proposed surgical plan would cause far anatomical effects that exceed a threshold set by a user, system 100, or both. In spinal procedures, the far anatomical effects can include interventional induced bony misalignment (e.g., vertebral misalignment) or other issues at non-imaged or non-modeled levels. If there is a potential adverse event or issue, the system 100 can present an option to expand virtual model to view a simulation of what potential risks could be at these other levels. In some embodiments, the system 100 can generate candidate surgical plans to correct or compensate for far anatomical effects at those other levels. This allows predictive-based far anatomical effects surgical planning based on comprehensive analysis of the patient's body.

The system 100 can determine additional data to assist with far anatomical effect analysis. The additional data can be image data of non-surgical sites, which may not have been available upon initial surgical planning. The system 100 can provide request for additional images of the non-surgical sites, instructions obtaining the additional images, and/or other data/input needed to fully evaluate risks, confidence scores, and/or outcomes. In some embodiments, the system 100 can determine additional data needed for far anatomical effect analyses. In spinal procedures, the system 100 can retrieve additional high-resolution images, such as MRI images, of the patient's entire spine to analyze regions of the spine remote from the surgical site. In lumbar procedures, images of the thoracic spine and cervical spines can be obtained from the patient's electronic records to supplement images of the lumbar spine. If thoracic spine and cervical spine images are unavailable, the system 100 can send a request or instructions (e.g., regions of body to be imaged, settings for MRI machines, etc.) for acquiring the images. The system 100 can then receive the images (e.g., new images acquired by the healthcare provider) and generate new models, simulations, and/or surgical plan incorporating the thoracic spine and cervical spine images or data.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110, the data analysis module 116, and/or the treatment planning module 118 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
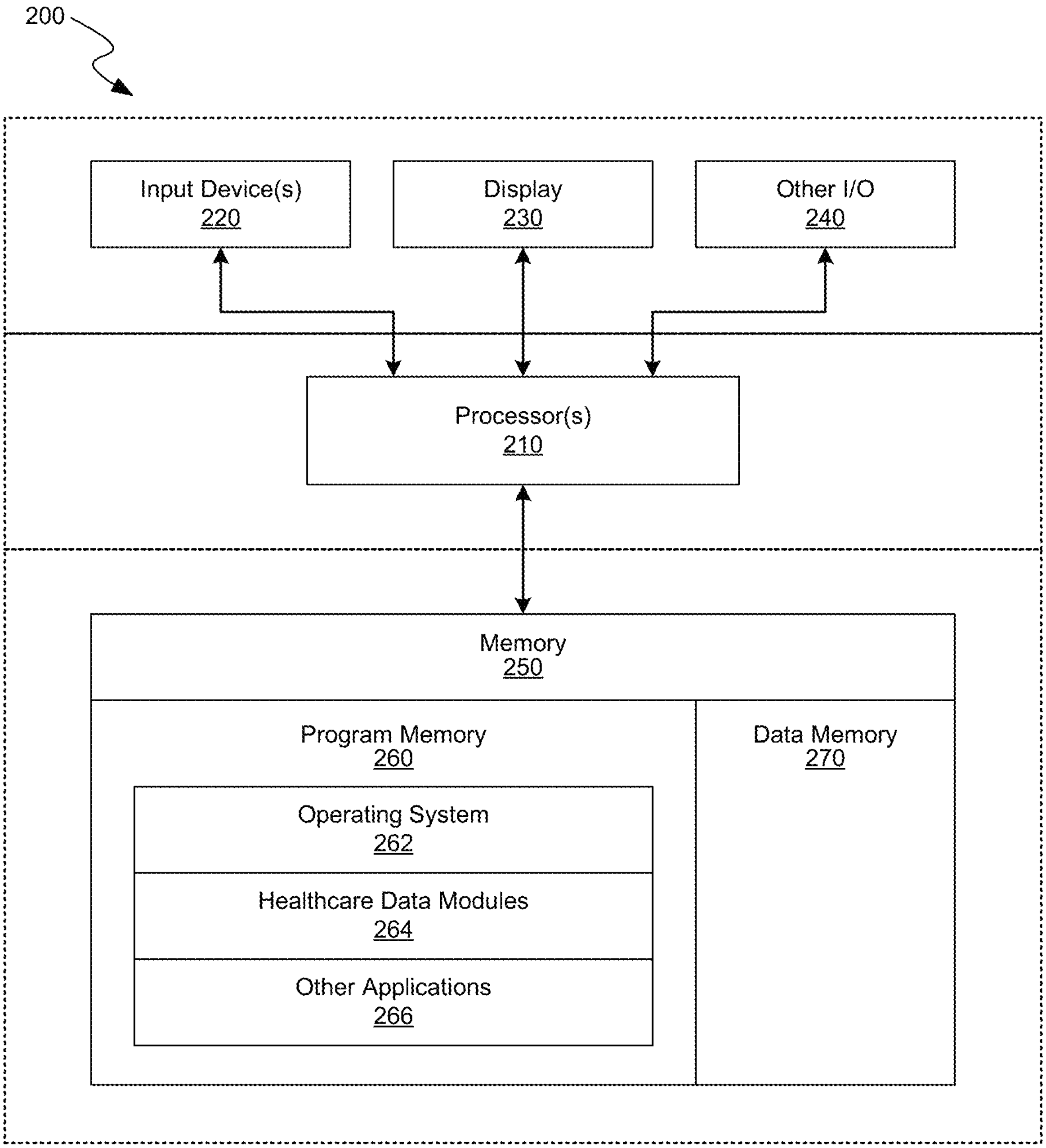
FIG. 2 illustrates a computing device suitable for use in connection with the system of FIG. 1, according to one or more embodiments of the present technology.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random-access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more healthcare data modules 264, and other application programs 266. The application programs 266 can include, without limitation, authentication programs, subscription programs, manufacturing programs, diagnostic programs, report generating programs, or the like. The healthcare data module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
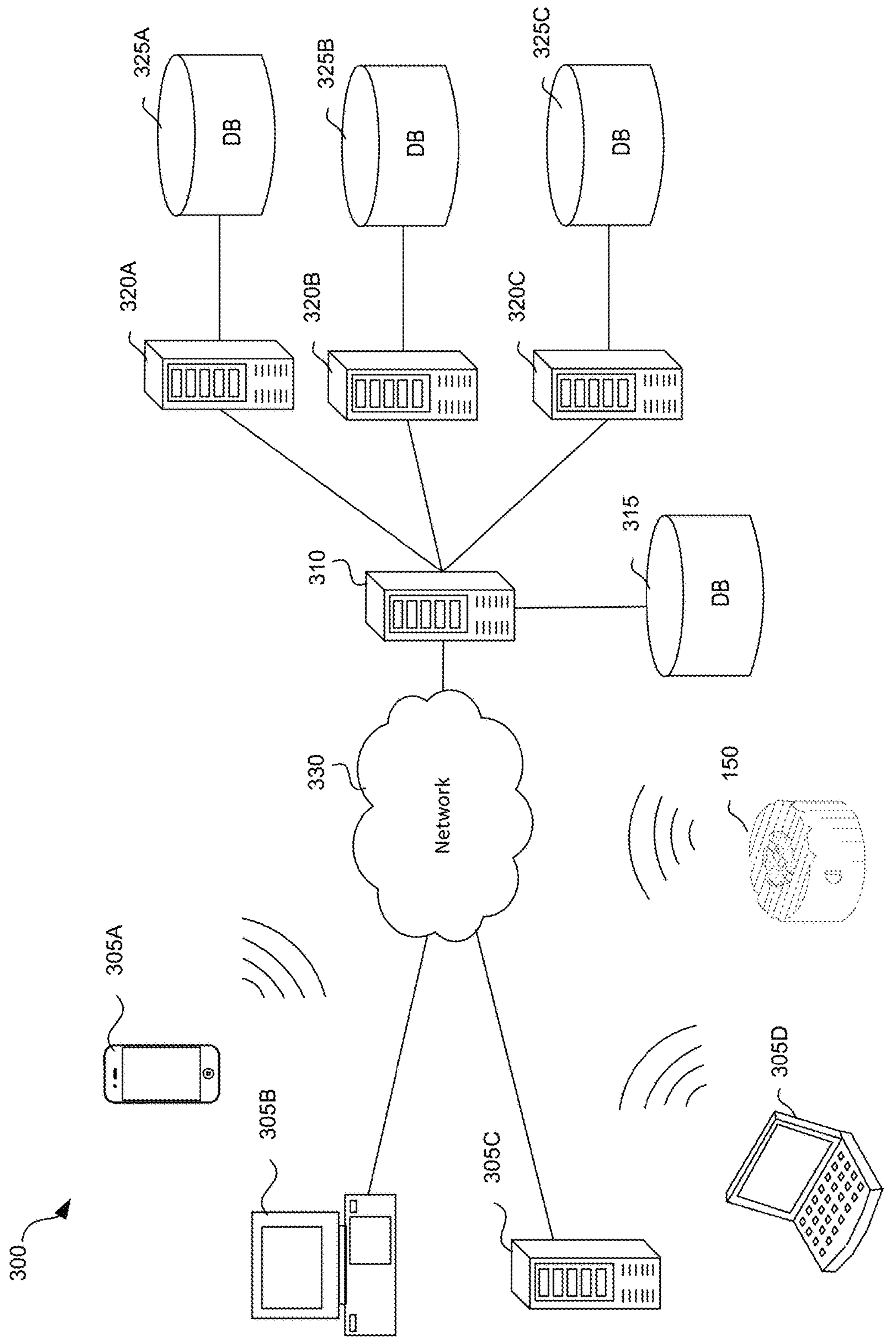
FIG. 3 is a system diagram illustrating an example of a computing environment in which the disclosed system operates in some embodiments.

FIG. 3 is a system diagram illustrating an example of a computing environment in which the disclosed system operates in some embodiments. In some embodiments, environment 300 includes one or more client computing devices 305A-D, examples of which can host the device 200. Client computing devices 305 operate in a networked environment using logical connections through network 330 to one or more remote computers, such as a server computing device. In some implementations, the client computing devices 305 can also include a medical implant, such as the medical implant 150 described above in relation to FIG. 1.

In some embodiments, device 310 is an edge server which receives client requests and coordinates fulfillment of those requests through other servers, such as servers 320A-C. In some embodiments, server computing devices 310 and 320 comprise computing systems, such as the device 200. Though each server computing device 310 and 320 is displayed logically as a single server, server computing devices can each be a distributed computing environment encompassing multiple computing devices located at the same or at geographically disparate physical locations. In some embodiments, each server computing device 320 corresponds to a group of servers.

Client computing devices 305 and server computing devices 310 and 320 can each act as a server or client to other server or client devices. In some embodiments, servers (310, 320A-C) connect to a corresponding database (315, 325A-C). As discussed above, each server 320 can correspond to a group of servers, and each of these servers can share a database or can have its own database. Databases 315 and 325 warehouse (e.g., store) information such as medical information, health records, biometric information of users, blockchain transactions involving user medical records, and other data. In some embodiments, the severs 320A-C can include digital filing cabinets and/or features of other servers disclosed herein, such as server 106 of FIG. 1. Though databases 315 and 325 are displayed logically as single units, databases 315 and 325 can each be a distributed computing environment encompassing multiple computing devices, can be located within their corresponding server, or can be located at the same or at geographically disparate physical locations.

Network 330 can be a local area network (LAN) or a wide area network (WAN), but can also be other wired or wireless networks. In some embodiments, network 330 is the Internet or some other public or private network. Client computing devices 305 are connected to network 330 through a network interface, such as by wired or wireless communication. While the connections between server 310 and servers 320 are shown as separate connections, these connections can be any kind of local, wide area, wired, or wireless network, including network 330 or a separate public or private network.

Figure 4:
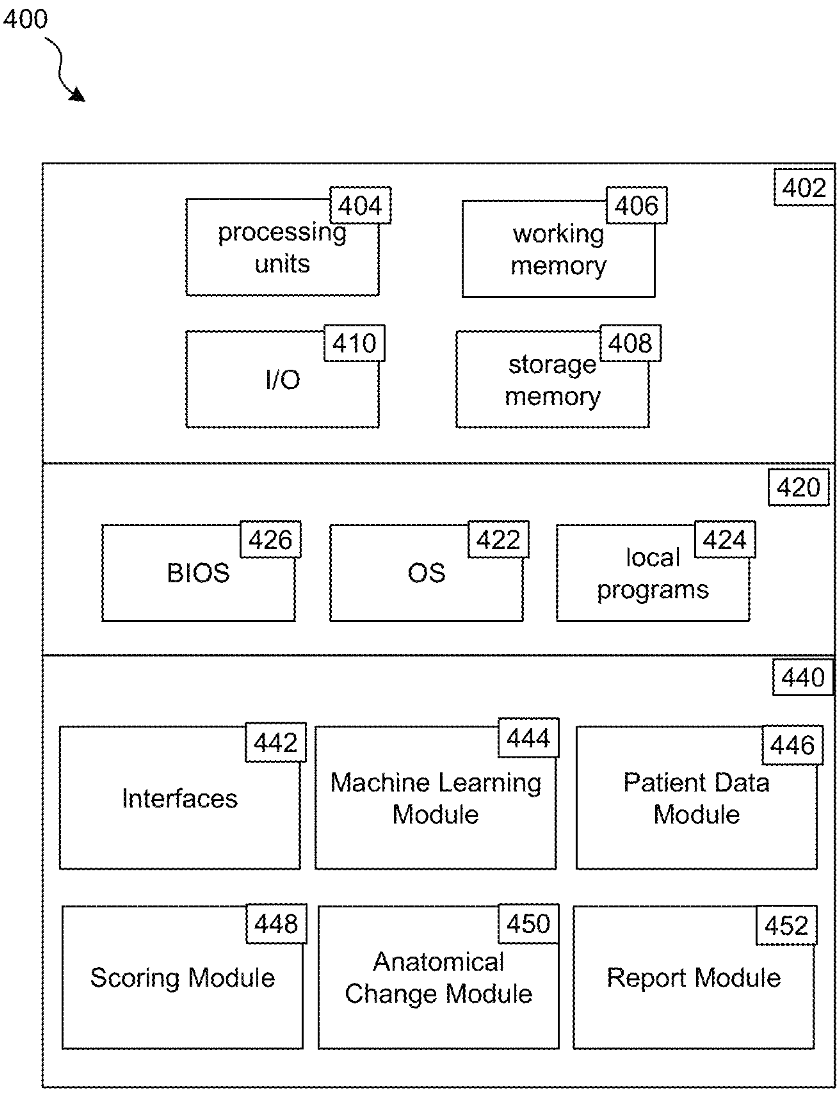
FIG. 4 is a block diagram illustrating components which, in some implementations, can be used in a system employing the disclosed technology.

FIG. 4 is a block diagram illustrating components 400 which, in some implementations, can be used in a system employing the disclosed technology. The components 400 can be used for storing, managing, analyzing, and accessing healthcare data in digital filing cabinets. The components 400 include hardware 402, general software 420, and specialized components 440. As discussed above, a system implementing the disclosed technology can use various hardware including processing units 404 (e.g., CPUs, GPUs, APUs, etc.), working memory 406, storage memory 408 (local storage or as an interface to remote storage, such as storage 315 or 325), and input and output devices 410. In various implementations, storage memory 408 can be one or more of: local devices, interfaces to remote storage devices, or combinations thereof. For example, storage memory 408 can be a set of one or more hard drives (e.g., a redundant array of independent disks (RAID)) accessible through a system bus or can be a cloud storage provider or other network storage accessible via one or more communications networks (e.g., a network accessible storage (NAS) device, such as storage 315 or storage provided through another server 320). Components 400 can be implemented in a client computing device such as client computing devices 305 or on a server computing device, such as server computing device 310 or 320.

General software 420 can include various applications including an operating system 422, local programs 424, and a basic input output system (BIOS) 426. Specialized components 440 can be subcomponents of a general software application 420, such as local programs 424. Specialized components 440 can be for providing patient-specific healthcare data can include a machine learning module 444, patient data module 446, scoring module 448, anatomical change module 450, report module 452, and components which can be used for providing user interfaces, transferring data, and controlling the specialized components, such as interfaces 442 (e.g., user interface on tablet, smartphone, laptop, etc.). In some implementations, components 400 can be in a computing system that is distributed across multiple computing devices or can be an interface to a server-based application executing one or more of specialized components 440. Although depicted as separate components, specialized components 440 may be logical or other nonphysical differentiations of functions and/or may be submodules or code-blocks of one or more applications.

Machine learning module 444 may be configured to analyze a pre-operative data (e.g., images, such as MRI, CT, CAT, or x-ray, and/or implant data, such as implant design files or a manufactured implant) of a patient to generate a model of anatomical changes in a patient that are predicted after installation of a patient-specific implant. The machine learning module 444 may be configured to utilize pre-operative data based on at least one machine-learning algorithm trained on at least one dataset reflecting approved pre-operative data. The at least one machine-learning algorithms (and models) may be stored locally at databases and/or externally at databases (e.g., cloud databases and/or cloud servers). Client devices may be equipped to access these machine learning algorithms and intelligently analyze pre-operative data and generate a model of anatomical changes in a patient that are predicted after installation of a patient-specific implant based on at least one machine learning model that is trained on historical models of anatomical changes. For example, machine learning module 444 can utilize pre-operative and/or post-operative data to determine that if the lumbar spine is corrected to a desired configuration with an implant, what changes occur at other spinal levels or regions, such as far anatomical effects, interventional-induced effects (e.g., effects to the thoracic and cervical spines, soft tissue), recovery/healing, or the like. The machine learning module 444 can determine intra-spine and inter-spine correlations between spinal elements (e.g., vertebrae, such as cervical spine (C1-C7), thoracic spine (T1-T12), lumbar spine (L1-L5), sacral spine (S1-S5), and the tailbone). Intra-spine correlated disease metrics can be between vertebrae of the cervical spine, vertebrae of the thoracic spine, or vertebrae of the lumbar spine. Inter-spine correlated disease metrics can be between vertebrae of the cervical and thoracic spines, vertebrae of the lumbar spine and cervical/thoracic spines, etc. For example, if the patient has an implant installed to correct a deformation of their lumbar spine, the machine learning module 444 can determine changes (e.g., reciprocal or correlated changes) to, for example, nearby anatomy due to correction of lumbar spine. As described herein, a machine-learning (ML) model may refer to a predictive or statistical utility or program that may be used to determine a probability distribution over one or more character sequences, classes, objects, result sets or events, and/or to predict a response value from one or more predictors. A model may be based on, or incorporate, one or more rule sets, machine learning, a neural network, or the like. In examples, the ML models may be located on the client device, service device, a network appliance (e.g., a firewall, a router, etc.), or some combination thereof. The ML models may process pre-operative data and other data stores of user health metrics to generate a model of short-term and/or long-term anatomical changes in a patient that are predicted after installation of a patient-specific implant. Based on an aggregation of data from a user's healthcare digital filing cabinet, healthcare provider pre-operative data storage, and other user data stores, at least one ML model may be trained and subsequently deployed to automatically utilize pre-operative data and generate a model of anatomical changes in a patient that are predicted after installation of a patient-specific implant. The trained ML model may be deployed to one or more devices. As a specific example, an instance of a trained ML model may be deployed to a server device and to a client device. The ML model deployed to a server device may be configured to be used by the client device when, for example, the client device is connected to the Internet. Conversely, the ML model deployed to a client device may be configured to be used by the client device when, for example, the client device is not connected to the Internet. In some instances, a client device may not be connected to the Internet but still configured to receive satellite signals with healthcare data. In such examples, the ML model may be locally cached by the client device. In some implementations, the machine learning module 444 identifies newly added pre-operative data in the digital filing cabinet and utilizes the new pre-operative data to generate a new model of anatomical changes in the patient that are predicted after installation of a patient-specific implant.

Patient data module 446 may be configured to receive a patient data set for a particular patient in need of medical treatment. The patient data set can include data representative of the patient's condition, anatomy, pathology, symptoms, medical history, preferences, and/or any other information or parameters relevant to the patient. For example, the patient data set can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.), or the like. The patient data set can also include image data, such as camera images, MRI images, ultrasound images, CAT scan images, PET images, X-Ray images, and the like. In some embodiments, the patient data set includes data representing one or more of patient identification number (ID), age, gender, BMI, LL, Cobb angle(s), PI, disc height, segment flexibility, bone quality, rotational displacement, and/or treatment level of the spine. The patient data set can be received at a server, computing device, or other computing system.

In some embodiments, the received patient data set can include disease metrics such as LL, Cobb angles, coronal parameters (e.g., coronal balance, global coronal balance, coronal pelvic tilt, etc.), sagittal parameters (e.g., PI, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the process 500 includes determining (e.g., automatically determining) one or more of the disease metrics based on the patient image data.

In some embodiments, the received patient data set can include pre-operative and/or post-operative relationships between anatomical features. The relationships can be determined based on correlations between pre- and post-operative data sets and used to identify how anatomical changes at one location can affect anatomy at another location. For example, alignment of the lumbar spine can cause alignment or misalignment of other portions of the spine, such as the thoracic or cervical spines. In some embodiments, implanting artificial implants at multiple levels (e.g., cage at intervertebral spaces, screw/rod systems spanning across multiple levels, etc.) of the spine can result in impaired mobility or functionality of other portions of the spine. The system can analyze pre- and post-operative datasets to identify correlations. Those correlations can be analyzed to determine relationships between anatomical elements, including vertebrae, vertebral bodies, cartilage, discs, nerves, muscles, ligaments, etc. The relationships include relationships between near or adjacent anatomical elements (e.g., maximum relative movement between adjacent vertebral bodies), groups of anatomical elements (e.g., spine or spinal segments), relationships between levels of the spine, equations of motion (e.g., relationship between forces/torques and anatomical movements), internal loading relationships, etc. Load-displacement relationships under single and combined forces (e.g., axial, shear forces) and moments (e.g., lateral moments, sagittal, axial moments, flexion, and/or extension) and other relationships can be generated based on numerical and measured results of segment data (e.g., single- and multi-motion reference patient data). Patient datasets can also include biometric data to identify correlations between pain and anatomical changes based on parametric models, non-parametric models, kinematic equations, etc. Dynamic virtual models can also be utilized to identify relationships. Confidence scores for identified relationships between anatomical features (or groups of anatomical features) can also be analyzed to determine an overall spinal outcome confidence score.

Post-operative reference data sets with matching procedures can be used to identify short term and/or long-term anatomical changes, including changes at or near a surgical site, posture changes, changes far or remote from the surgical site, nerve changes, pain data, etc.). For example, reference data sets for a lumbar spinal deformity correction can include changes to far or remote spinal features, such as the thoracic spine or cervical spine, which will receive different post-operative loading, such as loading distribution and amounts as the patient's anatomy is corrected. Together the pre- and post-operative data sets can show how modifying the lumbar spine to be in a normal anatomical configuration can cause changes, whether desired or adverse, to other regions (including remote anatomical elements). In some embodiments, the machine learning module 444 can be trained with training sets including lumbar lordosis corrections and associated proximal junctional kyphosis along the thoracic spine. The machine learning module 444 can identify matching pre-operative data sets and procedures with acceptable levels of proximal junctional kyphosis caused or induced by the procedures. The trained machine learning module 444 can determine the type of procedure, number of corrections (e.g., number of vertebral levels fused), and locations of correction along the lumbar spine to reduce the risk of proximal junctional kyphosis. Long-term post-treatment recovery can also be modelled using reference data sets with long-term post-treatment recovery and adverse far or remote anatomical effects. Such data sets can be used to train the machine learning module 444 to minimize or eliminate other changes, including the examples discussed below.

In an example, changes to a patient's lumbar spine can affect nerves of the lumbar spine that reach the patient's legs and feet, as well as organs, bowels, and bladder. A misalignment of the patient's spine can cause organs and tissues to be impacted. For example, a patient can experience numbness, aches, digestive issues, and/or respiratory issues when regions or levels of their spine is misaligned. In some cases, a misalignment of the spine, causes the nerves connected to region or levels of spine to not send signals to and from the brain. In an example, if the cobb angle of the spine reaches a threshold (e.g., 70 degrees) the patient can experience cardiac issues. In some embodiments, adjustments to correct a spinal region or level can relieve or eliminate the negative issues to the rest of the patient's body caused by a spinal deformity. For example, a corrective procedure to the lumbar spine can reduce pain or numbness in a patient's neck, arms, legs, and organs.

In some embodiments, the patient data can include pain data collected from the patient. For example, the patient can provide pain data (via a user interface) to the system. Pain data can include pain scores, such as lower back, hip, and/or leg pain scores based on questionnaires or tests, such as patient feedback (e.g., pain score) during pelvic gapping, pelvic compression, thigh thrusting, flexion abduction external rotation (FABER) test, and/or Gaenslen test. In some embodiments, the pain data can include pain reduction data, such as a change in the pain scores before and after surgical intervention. In some embodiments, the reference data and/or patient data includes mobility, alignment, debilitation, deformity, and/or degeneration information.

Scoring module 448 may be configured to determine a score for patient conditions in the patient data. The patient conditions can include pain, mobility, alignment, debilitation, deformity, and/or degeneration of the anatomy of the user. Scoring module 448 can determine scores for the features by comparing a patient's data to pre-determined metrics. In an example, a mobility score is based on a comparison of the patient data to a target mobility or range of motion for one or more vertebral bodies and/or joints. In an example, an alignment score is based on a number of degrees that a spinal feature region is off from a target alignment. The alignment score can be a single-level alignment score for a single vertebra, multi-level score for vertebrae, aggregate score for target alignment of a single anatomical feature, or other score disclosed herein for surgical site or site/feature away from the surgical site.

Anatomical change module 450 may be configured to generate a model (e.g., biomechanical models or simulations) of anatomical changes in a patient that are predicted after installation of a patient-specific implant. The model can illustrate how the changes to one section of the spinal anatomy can impact another section of the spine. For example, anatomical change module 450 can generate a model of the anatomical changes in a patient to provide predictions of how corrections to the lumbar spine impact the thoracic and cervical spines. For example, the present technology models the thoracic spine as a singular anatomical structure so that changes to the lumbar spine can impact the position of the thoracic spine. Anatomical change module 450 assess the impact of focal correction on global conditions/features (e.g., alignment, pain, debilitation, mobility, etc.) of the patient's anatomy. For example, the model can illustrate how a spinal deformity or degeneration causes a reduction in functional activities, increased debilitation, and increased pain. The model can predict how a correction to the spinal deformity with an implant installation can cause an increase in functional activities, decreased debilitation, and decreased pain for a patient. Models can illustrate how the changes to other regions can impact another region of the body, including the vascular system, respiratory system, or the like.

Report module 452 may be configured to generate and send a report to a device for a human to review. The report can include the scores for the features in the patient data, the generate a model of anatomical changes in a patient that are predicted after installation of a patient-specific implant. The report module 452 can identify or label predicted anatomical changes along the patient's spine caused by treatment at other locations along the spine.

The report module 452 can generate reports with predictions, modeling, simulations, and/or anatomical effects (e.g., surgical site effect, near anatomical effects, and/or far anatomical effects). The report can identify risk (e.g., visually along a visual representation of an anatomical model, metrics outside acceptable ranges, etc.) that a surgical plan would cause bony misalignment or other issues at non-imaged or non-modeled levels. The report can be used to predictive-based surgical planning based on comprehensive analysis of the patient's body. Post-operative reports without short-term and/or long-term outcomes can be used to plan for post-operative recovery, potential complications, pain management, and/or physical therapy. Additionally, the report can list requests for additional data for far anatomical effect analysis. The report can be modified or replaced based on the additional data to provide feedback for new simulations and/or surgical plan.

Figure 5A:
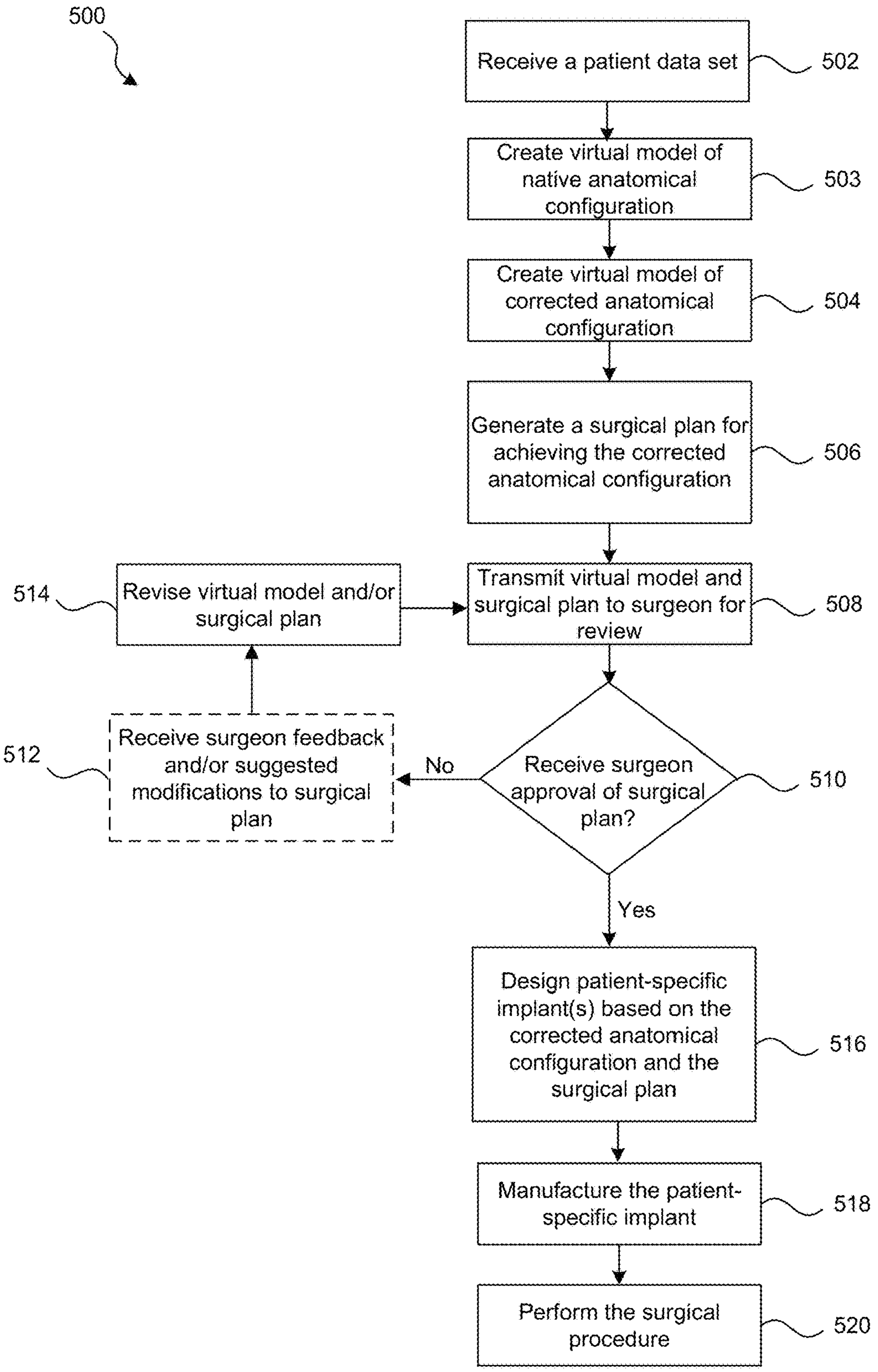
FIG. 5A is a flow diagram illustrating a method for providing patient-specific medical care, in accordance with embodiments of the present technology.

FIG. 5A is a flow diagram illustrating a method 500 for providing patient-specific medical care, in accordance with embodiments of the present technology. The method 500 can begin in step 502 by receiving a patient data set for a particular patient in need of medical treatment. The patient data set can be generally similar to or the same as the patient data set 108 of FIG. 1, and can include data representative of the patient's condition, anatomy, pathology, symptoms, medical history, preferences, and/or any other information or parameters relevant to the patient. For example, the patient data set can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.), and/or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and/or the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, sacroiliac joint anatomy (e.g., dimension(s), property (s), curvature, shape, topology, etc.), pain data, and/or treatment level of the spine. The patient data set can be received at a server, computing device, and/or another computing system. For example, in some embodiments the patient data set can be received by the server 106 shown in FIG. 1 and/or the computing system 100. In some embodiments, the computing system that receives the patient data set in step 502 also stores one or more software modules (e.g., the data analysis module 116 and/or the treatment planning module 118, shown in FIG. 1, and/or additional software modules for performing various operations of the method 500).

In some embodiments, the received patient data set can include disease metrics such as lumbar lordosis, Cobb angles, pain data, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a two- or three-dimensional visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including at least part or all of the sacrum, lumbar region, thoracic region, and/or cervical region. In another non-limiting example, the virtual model can include a visual representation of a patient's pelvic region, including at least part or all of the sacrum, ilium, and/or one or both of the sacroiliac joints. In some embodiments, the virtual model includes soft tissue, cartilage, and/or other non-bony structures. In other embodiments, the virtual model only includes the patient's bony structures. Examples of virtual models of native anatomical configurations are described below with respect to FIGS. 9A-9B. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, pain data, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected or adjusted anatomical configuration (which can also be referred to herein as a "planned configuration," an "optimized geometry," a "post-operative anatomical configuration," and/or a "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4 (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, the sacroiliac joint fused at the S1 and/or S2 vertebrae, load transfer to sacroiliac joint is reduced by 5%, patient pain score is reduced by at least 10%, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, a target intervertebral space height, and/or a target mobility or range of motion for one or more vertebral bodies and/or joints (e.g., sacroiliac joint) after a fusion procedure. The difference between the native anatomical configuration and the corrected anatomical configuration may be referred to as a "patient-specific correction," a "target correction," an "adjustment," and/or a "patient-specific adjustment."

Once the corrected anatomical configuration is determined, the computing system can generate a two- or three-dimensional visual representation of the patient's anatomy with the corrected anatomical configuration. As with the virtual model created in step 503, the virtual model of the patient's corrected anatomical configuration can include one or more regions of interest, and may include at least part or all of the patient's anatomy within the regions of interest (e.g., any combination of tissue types including, but not limited to, bony structures, cartilage, muscles, ligaments, soft tissue, vascular tissue, nervous tissue, etc.). As a non-limiting example, the virtual model can include a visual representation of the patient's spinal cord region in a corrected anatomical configuration, including at least part or all of the sacrum, lumbar region, thoracic region, and/or cervical region. In some embodiments, the virtual model includes soft tissue, cartilage, and other non-bony structures. In other embodiments, the virtual model only includes the patient's bony structures.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, SIJF, etc.) across a specific range of vertebral levels (e.g., L1-L4, L1-5, L3-T12, S1-S5, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, pain data, coronal parameters, sagittal parameters, and/or pelvic parameters) corresponding to the expected post-operative patient anatomy. The surgical plan can be generated by a computing system that is the same as or different than the computing system that created the virtual model of the corrected anatomical configuration. In some embodiments, the surgical plan can also be based on one or more reference patient data sets as previously described with respect to FIGS. 1-4. In some embodiments, the surgical plan can also be based at least in part on surgeon-specific preferences and/or outcomes associated with a specific surgeon performing the surgery. In some embodiments, the surgical plan can also be based at least in part on models or simulations (e.g., biomechanical simulations) of the patient's anatomy, such as simulations of spinal load transfer via one or both of the sacroiliac joints to the coxal bones of the patient. In some embodiments, more than one surgical plan is generated in step 506 to provide a surgeon with multiple options.

After the virtual model of the corrected anatomical configuration is created in step 504 and the surgical plan is generated in step 506, the method 500 can continue in step 508 by transmitting the virtual model of the corrected anatomical configuration and the surgical plan for surgeon review. In some embodiments, the virtual model and the surgical plan are transmitted as a surgical plan report. In some embodiments, the same computing system used in steps 502-506 can also transmit the virtual model and surgical plan to a computing device for surgeon review (e.g., the client computing device 102 described in FIG. 1). This can include directly transmitting the virtual model and/or the surgical plan to the computing device, and/or uploading the virtual model and/or the surgical plan to a cloud or other storage system for subsequent downloading. Although step 508 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 508 may include the virtual model of the patient's native anatomical configuration (or images thereof) in addition to the virtual model of the corrected anatomical configuration. In embodiments in which more than one surgical plan is generated in step 506, the method 500 can include transmitting more than one surgical plan to the surgeon for review and selection.

The surgeon can review the virtual model and/or surgical plan and, in step 510, either approve or reject the surgical plan (and/or, if more than one surgical plan is provided in step 508, select one of the provided surgical plans). If the surgeon does not approve the surgical plan in step 510, the surgeon can optionally provide feedback and/or suggested modifications to the surgical plan (e.g., by adjusting the virtual model or changing one or more aspects about the plan). Accordingly, the method 500 can include receiving (e.g., via the computing system) the surgeon feedback and/or suggested modifications. If surgeon feedback and/or suggested modifications are received in step 512, the method 500 can continue in step 514 by revising (e.g., automatically revising via the computing system 100) the virtual model and/or surgical plan based at least in part on the surgeon feedback and/or suggested modifications received in step 512. In some embodiments, the surgeon does not provide feedback and/or suggested modifications if they reject the surgical plan. In such embodiments, step 512 can be omitted, and the method 500 can continue in step 514 by revising (e.g., automatically revising via the computing system 100) the virtual model and/or the surgical plan by selecting new and/or additional reference patient data sets. The revised virtual model and/or surgical plan can then be transmitted to the surgeon for review. Steps 508, 510, 512, and 514 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 510, the method 500 can continue in step 516 by designing (e.g., via the same computing system that performed steps 502-514) at least one patient-specific implant based at least partially on the corrected anatomical configuration and/or the surgical plan. For example, each patient-specific implant can be specifically designed such that, when implanted in the particular patient, it directs the patient's anatomy to occupy the corrected anatomical configuration (e.g., transforming the patient's anatomy from the native anatomical configuration to the corrected anatomical configuration). In a non-limiting example, this can include altering the relative positions or alignment of one or more vertebral bodies, fusing one or more vertebral bodies at a specific vertebral level, and/or fusing one or both of a patient's sacroiliac joints. Each patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, each patient-specific implant is designed solely based on the virtual model of the corrected anatomical configuration and/or without reference to pre-operative patient images.

Each patient-specific implant can be any of the implants described herein and/or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for a patient-specific orthopedic implant can include implant shape, size, material, and/or effective stiffness (e.g., lattice density, number of struts, location of struts, etc.).

In some embodiments, designing the implant in step 516 can optionally include generating fabrication instructions for manufacturing the implant. For example, the computing system may generate computer-executable fabrication instructions that that, when executed by a manufacturing system, cause the manufacturing system to manufacture the implant. In some embodiments, designing the implant in step 526 includes generating CAD models and/or design parameters that can be used by a manufacturing system to generate computer-executable fabrication instructions, as described below.

In some embodiments, the patient-specific implant is designed in step 516 only after the surgeon has reviewed and approved the virtual model with the corrected anatomical configuration and the surgical plan. Accordingly, in some embodiments, the implant design is neither transmitted to the surgeon with the surgical plan in step 508, nor manufactured before receiving surgeon approval of the surgical plan. Without being bound by theory, waiting to design the patient-specific implant until after the surgeon approves the surgical plan may increase the efficiency of the method 500 and/or reduce the resources necessary to perform the method 500.

The method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively, or additionally, the implant can be manufactured using subtractive manufacturing techniques, such as CNC machining, electrical discharge machining (EDM), grinding, laser cutting, water jet machining, manual machining (e.g., milling, lathe/turning), and/or like technologies, and/or combinations thereof. The implant may be manufactured by any suitable manufacturing system (e.g., the manufacturing system 124 shown in FIG. 1). In some embodiments, the implant is manufactured by the manufacturing system executing the computer-readable fabrication instructions generated by the computing system in step 516.

In some embodiments, manufacturing the patient-specific implant at step 518 can be performed at a location remote from the computing system used to perform one or more of steps 502-516. In such embodiments, step 516 can include receiving fabrication instructions or manufacturing data from the remote computing systems over a wireless network. In other embodiments, step 516 includes receiving, at a manufacturing systems, other manufacturing data associated with the patient-specific implant, such as CAD models and/or design parameters. Representative design parameters can include, for example, implant shapes, dimensions, materials, material properties, density, porosity, lattice structure, surface finishes, and the like. The manufacturing system can then manufacture the patient-specific implant based on the CAD models and/or design parameters. In embodiments in which the manufacturing system receives CAD models and/or design parameters, the manufacturing system may generate computer-executable fabrication instructions based on the CAD models and/or design parameters. The computer executable fabrication instructions can then control the manufacturing system to manufacture the patient-specific implant.

Once the implant is manufactured in step 518, the method 500 can continue in step 520 by implanting the patient-specific implant into the patient. The surgical procedure can be performed manually, by a robotic surgical platform (e.g., a surgical robot), and/or a combination thereof. In embodiments in which the surgical procedure is performed at least in part by a robotic surgical platform, the surgical plan can include computer-readable control instructions configured to cause the surgical robot to perform at least part or all of the patient-specific surgical procedure.

In some embodiments, the method 500 can further include performing or more models or simulations, such as biomechanical simulations, based on the native virtual model of step 503 and/or the corrected virtual model of step 504. The biomechanical simulations can be used to determine, analyze, and/or predict the effect of one or more forces or loads (e.g., compressive loads, shear loads, etc.) applied to the patient's anatomy before and/or after a surgical procedure, such as a surgical procedure included as part of the surgical plan of step 506. In some embodiments, the biomechanical simulations can include predicting forces applied to the patient's anatomy from one or more muscles and/or ligaments (e.g., simulated muscles and/or ligaments). In some embodiments, the biomechanical simulations can include simulating spinal load transfer between a first anatomical feature and a second anatomical feature, such as between two vertebral bodies, between a sacrum and an ilium, and/or between a portion of a patient's spine and a sacroiliac joint. In some embodiments, the biomechanical simulations can include simulating loads or forces based on a range of motion of an anatomical feature of the patient (e.g., a range of motion on the spine), and determining whether the simulated load is acceptable, as described previously. The biomechanical simulations can be performed using computational models, multibody models, finite element models, and/or any other suitable process or techniques known to those of skill in the art. In some embodiments, the method 500 can include simulating anatomical alignments of portions of the patient's lumbar spine, thoracic spine, and/or cervical spine. The method 500 can be used to determine whether one or more corrective adjustments to the lumbar spine (or another section) impacts anatomical alignment of the cervical or thoracic spine (or other sections).

The method 500 can be implemented and performed in various ways. In some embodiments, steps 502-516 can be performed by a computing system (e.g., the computing system 100 of FIG. 1) associated with a first entity, step 518 can be performed by a manufacturing system associated with a second entity, and step 520 can be performed by a surgical provider, surgeon, and/or robotic surgical platform associated with a third entity. Any of the foregoing steps may also be implemented as computer-readable instructions stored in memory and executable by one or more processors of the associated computing system(s).

Figure 5B:
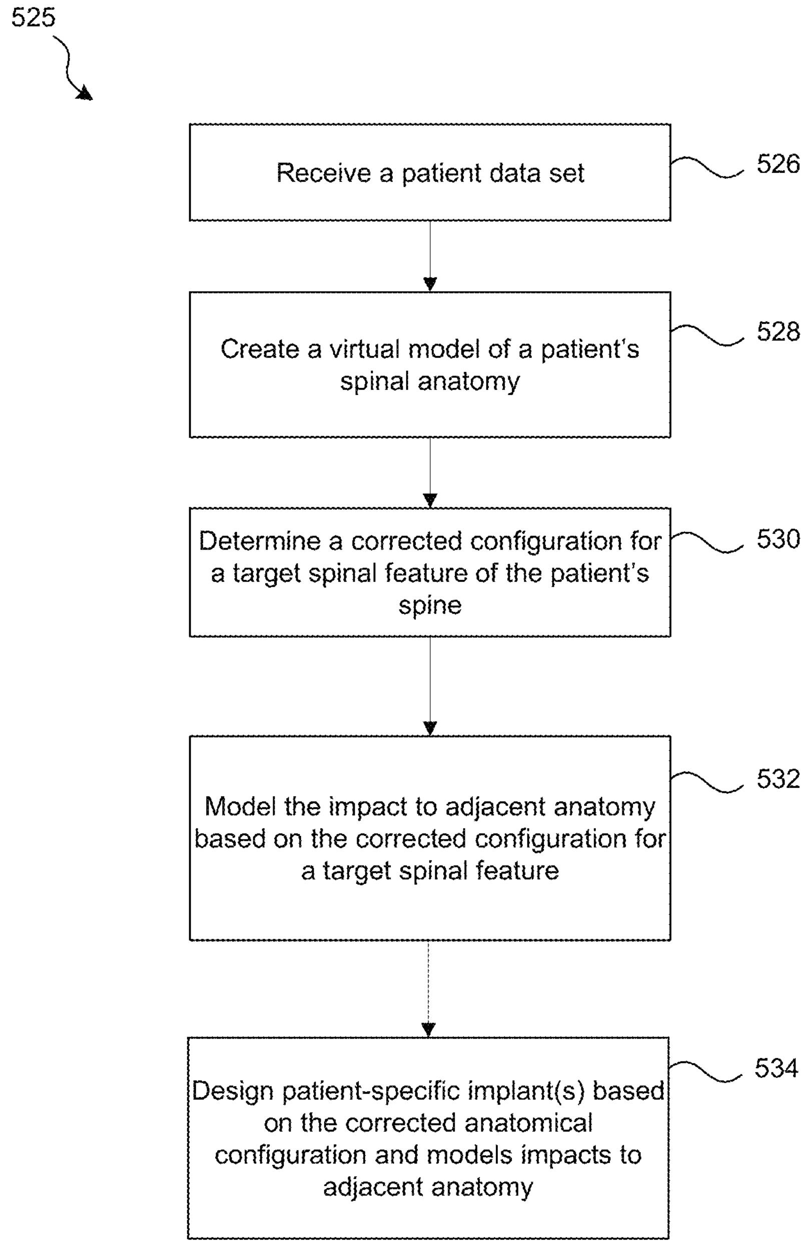
FIG. 5B is a flow diagram illustrating a method for modeling anatomical changes in adjacent anatomy based on corrective changes to a spinal region, in accordance with embodiments of the present technology.

FIG. 5B is a flow diagram illustrating a method 525 for modeling anatomical changes in adjacent anatomy based on corrective changes or adjustments to a spinal region, in accordance with embodiments of the present technology. The method 525 can begin in step 526 by receiving a patient data set for a particular patient in need of medical treatment. Step 526 can by generally similar to or the same as step 502 of the method 500 of FIG. 5A. Representative patient data may include, for example, X-rays or other images of the patient's spinal regions from a plurality of views (e.g., anterior, posterior, lateral) and under a variety of conditions (e.g., sitting, standing, load-bearing, and/or non-load-bearing). Representative patient data may also include (i) pain scores specific to patient pain at or associated with specific spinal regions, (ii) movement or kinetic data associated with mobility of the patient's spinal regions, (iii) load-bearing data indicative of loads at various points on the spine under a variety of conditions (standing, sitting, laying, etc.), and/or (iv) other suitable patient data.

The method 525 can continue in step 528 by creating a virtual model of a patient's spine/spinal anatomy. Step 528 can be generally similar to or the same as step 503 and 504 of the method 500 of FIG. 5A. For example, in step 528, the virtual model can be generated based on the X-rays, MRI images, or other image data included in the patient data set received in step 526. The virtual model can be a two- or three-dimensional visual representation of the patient's native anatomy.

The method 525 can continue in step 530 by determining a corrected configuration for a target spinal feature (e.g., lumbar spine) of the patient's spine. Step 530 can be generally similar or the same as step 504 of the method 500. For example, using the analysis procedures described previously, a computing system can determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4 (e.g., based on a similarity of the reference patient data set to the patient data set and/or whether the reference patient had a favorable treatment outcome). In some embodiments, step 530 can include creating a virtual model of the corrected or adjusted anatomical configuration for the patient based on the determined corrected configuration. In some embodiments, step 530 can include identifying one or more regions of the patient's spine for adjustment, and adjusting one or more anatomic elements of the native virtual model of step 528 to produce the corrected configuration for the patient's spine.

The method 525 can continue at step 532 by modeling (e.g., via the virtual model of step 528 and/or the virtual models of step 503 or 504 of FIG. 5A) the anatomy of the patient to determine the impact to adjacent anatomy based on the corrected configuration for a target spinal feature. For example, method 525 can model changes to thoracic spine or cervical spine based on corrections (e.g., via an implant installation) to the lumbar spine. Method 525 can determine the impact to adjacent anatomy based on the corrected configuration for a target spinal feature with one or more expected spine metrics (e.g., lumbar lordosis, Cobb angles, pain data, coronal parameters, sagittal parameters, and/or pelvic parameters) corresponding to the expected post-operative patient anatomy.

In some embodiments, step 532 can further include predicting post-operative loading/forces, such as compressive and/or shear forces, in at least one of the patient's joints, vertebrae, disks, or any spinal feature. The predicted post-operative compressive and/or shear forces can be based at least partially on the patient data sets and/or a simulation (e.g., a biomechanical simulation) performed based on the patient's virtual anatomy. In some embodiments, step 532 can further include modeling one or more muscles and/or ligaments, and predicting one or more forces applied to the adjacent anatomy of the corrected target spinal feature based on the modeled muscles and/or ligaments.

In some embodiments, the method 525 can further include performing one or more biomechanical simulations on the patient's anatomy. In at least some embodiments, for example, the method 525 can include performing a biomechanical simulation of spinal load transfer via the target spinal feature to one or more adjacent anatomical features of the patient. For example, as a lumbar spinal deformity is corrected, adjacent spinal features, such as the thoracic spine or cervical spine, will receive different loading, such as loading distribution and amounts (e.g., weight, force, pressure, etc.) as the patient's anatomy is corrected. For example, modifying the lumbar spine to be in a normal anatomical configuration can cause other regions of the spine to be adjusted to normal or preferred configurations. The normal configuration can be determined based on, for example, reference configurations (e.g., reference anatomical configurations). Preferred configurations can be inputted by, for example, machine learning models for determining preferred configurations for patients, users (e.g., healthcare provider, physician, etc.), or the like. Additionally, muscles and other tissue can be subjected to normal loading due to the normal overall configuration of the spine. The impact on the patient's spine based on the of number and locations of correction with a portion of the spine can be analyzed. For example, correcting lumbar lordosis (LL) to restore ideal sagittal alignment could increase the risk for development of proximal junctional kyphosis (PJK). The system can determine the type of procedure, number of corrections (e.g., number of vertebral levels fused), and locations of correction along the lumbar spine to reduce the risk of proximal junctional kyphosis along the thoracic spine. Post-treatment recovery can also be modelled. Inflammation of the membranes that surround the nerves of the spinal cord can cause arachnoiditis and leads to pain. In lumbar fusion procedures, upper back pain may be experienced until the nerve fully heals, which may be many months after surgery.

When modifying spinal deformities, such as scoliosis, changes to the patient's spine can cause or correct asymmetries in the patient. The asymmetries can include ribs protruding from a patient's side, hip misalignment, uneven leg lengths, slanting or tilt of the patient's shoulders, or any abnormal feature of the patient. For example, a misalignment of the spine, causes the nerves connected to regions or levels of spine to not send signals to and from the brain. Correction of a spinal deformity at a target location, can increase the levels of cerebrospinal fluid (CSF) to the brain. The virtual model can simulate that as the target spinal feature is adjusted, the circulation of CSF to the patient's brain can increase which will reduce headaches for the patient.

In an example, if the cobb angle of the spine reaches a threshold (e.g., 70 degrees) the patient can experience cardiac issues. The biomechanical simulation can illustrate how strain on the patient's heart is relieved as the curvature in their spine is corrected. In some embodiments, adjustments to correct a spinal region or level can relieve or eliminate or account for the negative issues to the rest of the patient's body caused by a spinal deformity, such as digestive issues. For example, a corrective procedure to the lumbar spine can reduce pain or numbness in a patient's neck, arms, legs, and organs.

In at least some embodiments, for example, the one or more biomechanical simulations can include performing pre-operative and/or post-operative simulations to predict patient outcomes based on simulated adjustments to the target spinal feature. The predicted patient outcomes can be based at least partially on the patient data sets.

In at least some embodiments, for example, the method 525 can include performing a biomechanical simulation to determine how bone, soft tissue, or muscle adjacent to a target spinal feature will be impacted by a corrective procedure to the target spinal feature. For example, when an implant is installed to correct the target spinal feature, the muscle and soft tissue within a proximity of the implant may be damaged or irritated by the implant or the surgery to install the implant.

In some implementations, method 525 can model how a corrected configuration for the target spinal feature impacts conditions (e.g., pain, mobility, alignment, debilitation, etc.) of the patient. For example, the model illustrates that corrections to the lumbar spine can reduce a user's pain and improve a patient's mobility and anatomical alignment.

The method 525 can utilize parametric modeling methods and/or non-parametric modeling methods when modeling the impact to adjacent anatomy based on the corrected configuration for a target spinal feature. The virtual model can be interactive so that a user can make adjustments to any spinal feature in the model, and the model will illustrate how the adjustment to the spinal feature impacts the other anatomy of the patient.

At step 534, the method 525 can design patient-specific implant(s) (as described at step 516 of FIG. 5A) based on the corrected anatomical configuration and models impacts to adjacent anatomy.

Figure 5C:
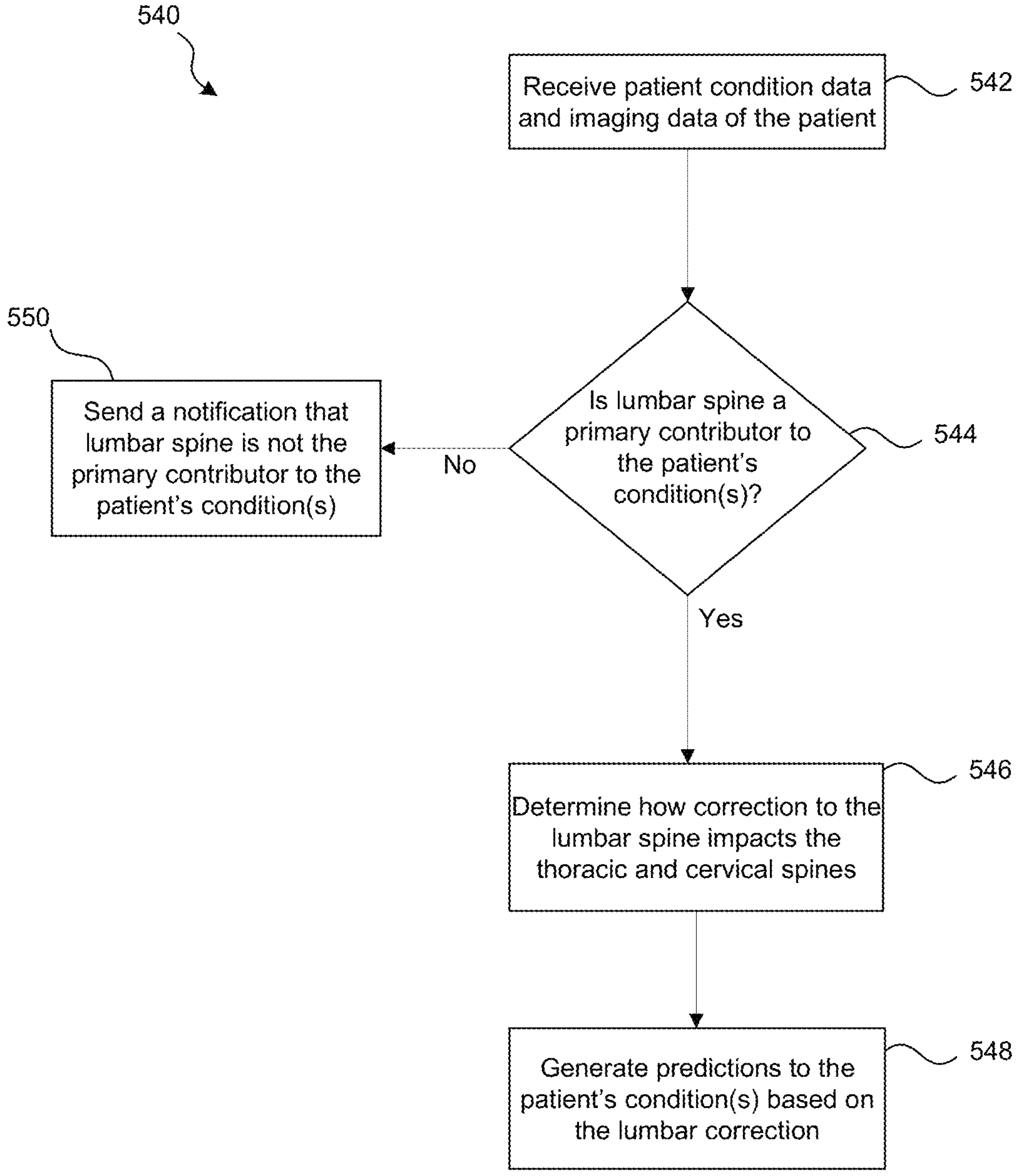
FIG. 5C is a flow diagram illustrating a method for providing patient-specific medical care for a patient's spinal deformity based on patient data, in accordance with embodiments of the present technology.

FIG. 5C is a flow diagram illustrating a method 540 for providing patient-specific medical care for a patient's spinal deformity based on patient data, in accordance with embodiments of the present technology. The method 540 can begin in step 542 by receiving patient condition data (e.g., pain, mobility, alignment, debilitation, deformity, and/or degeneration of the patient anatomy) and imaging data for a particular patient in need of medical treatment. Step 542 can by generally similar to or the same as step 502 of the method 500 of FIG. 5A. In some implementations, the method 540 determines a score for the patient condition data (as described in FIGS. 4 and 6).

The method 540 can continue in step 544 by determining whether the lumbar spine is a primary contributor to the patient's condition. In some embodiments, step 544 can include comparing the patient condition data (e.g., step 542) to reference lumbar data to determine whether the lumbar spine is the primary contributor to the patient's condition. The reference lumbar data can include reference patient condition data, and lumbar spine dysfunction can correspond to one or more similarities between the patient condition data and the reference patient condition data. For example, if the patient has pain data that is generally similar to or the same as reference patient pain data for a reference patient with known lumbar dysfunction/degeneration, then it can be determined that the lumbar spine is the primary contributor to the patient's pain. In some embodiments, step 544 can include performing one or more tests on the patient to determine whether the lumbar spine is the primary contributor. The one or more tests can include, but are not limited to, a pain pelvic gapping test, a pelvic compression test, a thigh thrusting test, a flexion abduction external rotation test, and/or a Gaenslen test.

If, at step 544, the lumbar spine is determined to be the primary contributor, the method 540 can continue in step 546 by determining how the correction to the lumbar spine impacts the thoracic and cervical spines. For example, correction to the lumbar spine with an implant can impact patient conditions (e.g., pain, mobility, alignment, debilitation, deformity, and/or degeneration of the patient anatomy in other areas.

At step 548, method 540 can generate predictions (e.g., via machine learning models) to the patient's condition based on the lumbar correction. For example, method 540 can generate condition scores to illustrate to the patient how correction to the lumbar spine can decrease pain, improve alignment, increase mobility, and decrease debilitation. Method 540 can generate the predictions based on comparing the patient current condition data to reference condition data of other patients that have had lumbar correction. For example, method 540 can receive pain data corresponding to the particular patient. The pain data can be used to determine one or more adjustments to the virtual model (e.g., virtual mode as described at step 525 of FIG. 5B). The one or more adjustments can be used to determine a pain reduction score and/or a change (e.g., an expected or predicted change) in pain score. The pain reduction score and/or the change in pain score can be based at least partially on reference patient data (e.g., reference patient pain data), and can be determined prior to designing and/or manufacturing the at least one patient-specific implant.

If, at step 544, lumbar spine is determined to not be the primary contributor, the method 540 can continue in step 550 by sending or providing a notification (e.g., to a user, a physician, etc.) that lumbar spine is not the primary contributor to the patient's condition. In some embodiments, step 550 can further include identifying a treatment plan to reduce patient condition based on repositioning the patient's spine using one or more implanted devices, such as any of the devices described and/or incorporated by reference herein.

Method 540 can be implemented to determine and display reciprocal changes to nearby anatomy due to correction of any index anatomy. The methods 525, 540 can be implemented and performed in various ways. In some embodiments, steps can be performed by a computing system (e.g., the computing system 100 described below with respect to FIG. 1) associated with a first entity. Any of the foregoing steps may also be implemented as computer-readable instructions stored in memory and executable by one or more processors of the associated computing system(s).

Figure 6:
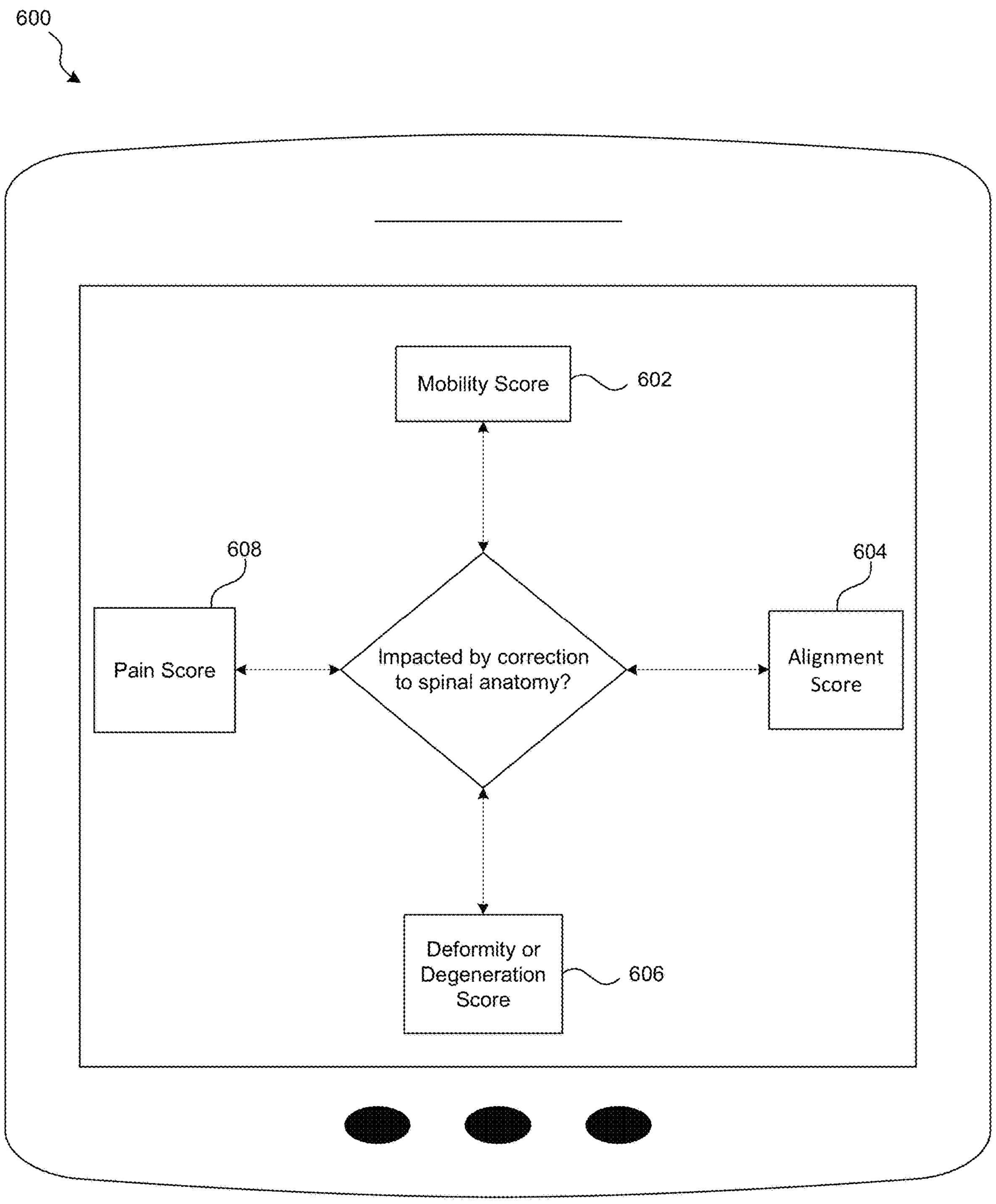
FIG. 6 illustrates an exemplary GUI detailing scoring of patient conditions associated with spinal correction in connection with the methods described herein, according to an embodiment.
Figure 7D:
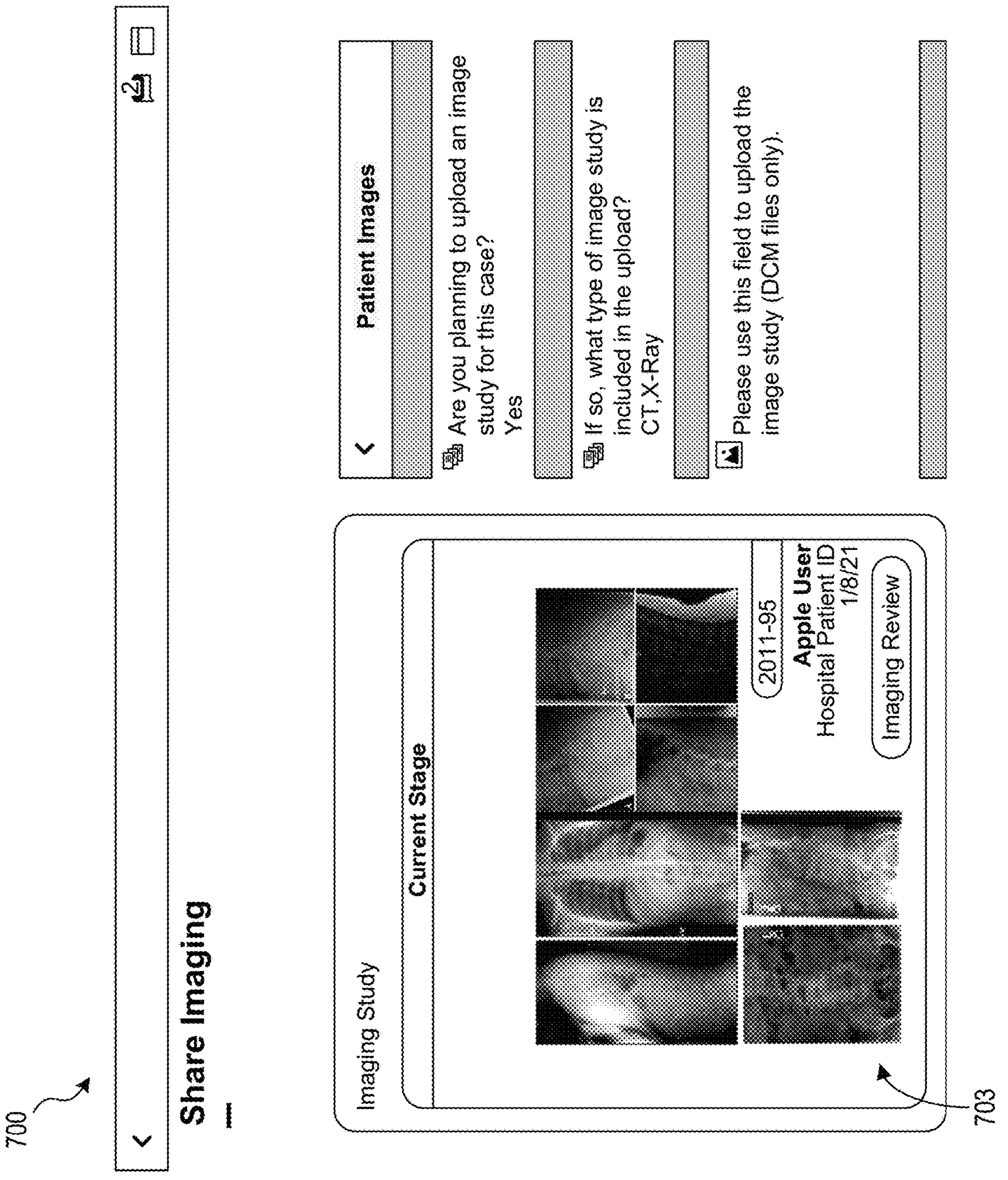

FIG. 6 illustrates an exemplary GUI 600 detailing scoring of patient conditions associated with spinal correction in connection with the methods described herein, according to an embodiment. The GUI 600 can display scores (e.g., mobility score 602, alignment score 604, deformity or degeneration score 606, and pain score 608) for patient conditions that are impacted by a correction (e.g., installation of a spinal implant) to a spinal anatomy feature. The GUI 600 can illustrate how the patient conditions are related and display reciprocal changes to the scores based on a corrective procedure to a spinal feature. For example, FIGS. 7A-13 further illustrate select aspects of providing patient-specific medical care, e.g., in accordance with process 500 and/or 600. For example, FIGS. 7A-7D illustrate an example of a patient data set 700 (e.g., as received in step 502 of process 500). The patient data set 700 can include any of the information previously described with respect to the patient data set. For example, the patient data set 700 includes patient information 701 (e.g., patient identification no., patient MRN, patient name, sex, age, BMI, surgery date, surgeon, etc., shown in FIGS. 7A and 7B), diagnostic information 702 (e.g., Oswestry Disability Index (ODI), VAS-back score, VAS-leg score, Pre-operative pelvic incidence, pre-operative lumbar lordosis, pre-operative PI-LL angle, pre-operative lumbar coronal cobb, etc., shown in FIGS. 7B and 7C), and image data 703 (x-ray, CT, MRI, etc., shown in FIG. 7D). In the illustrated embodiment, the patient data set 700 is collected by a healthcare provider (e.g., a surgeon, a nurse, etc.) using a digital and/or fillable report that can be accessed using a computing device. In some embodiments, the patient data set 700 can be automatically or at least partially automatically generated based on digital medical records of the patient. Regardless, once collected, the patient data set 700 can be transmitted to the computing system configured to generate the surgical plan for the patient.

Figure 8A:
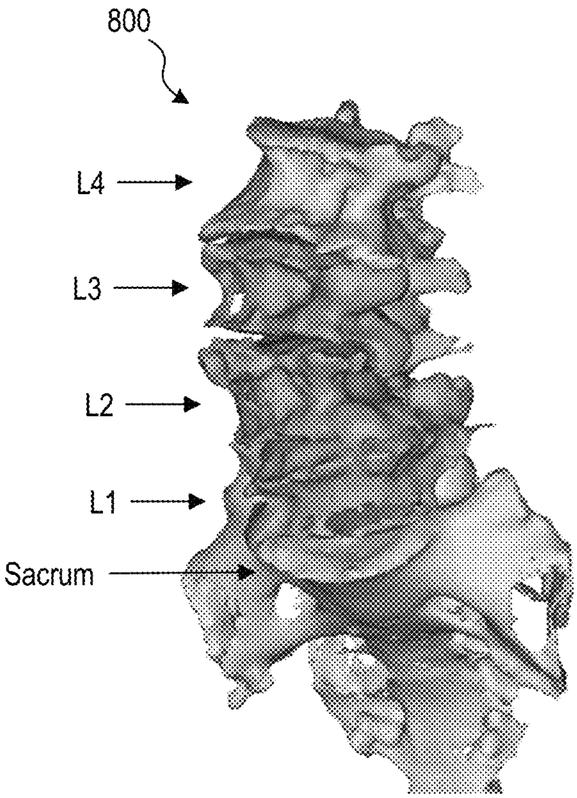
FIGS. 8A and 8B illustrate an exemplary virtual model of a patient's spine that may be used and/or generated in connection with the methods described herein, according to an embodiment.
Figure 8B:
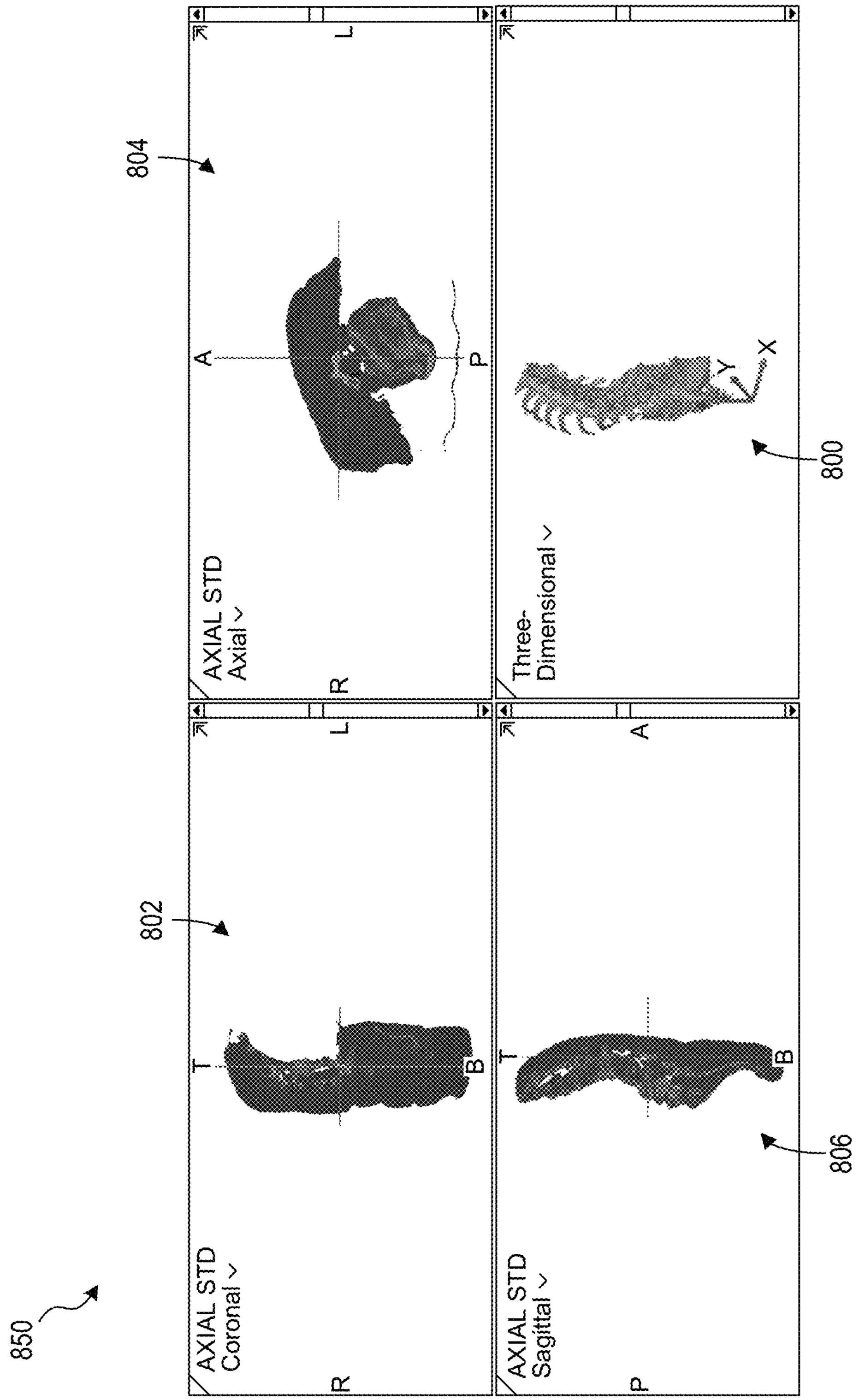

FIGS. 8A and 8B illustrate an example of a virtual model 800 of a patient's native anatomical configuration (e.g., as created in step 504/506 of process 500). In particular, FIG. 8A is an enlarged view of the virtual model 800 of the patient's native anatomy and shows the patient's native anatomy of their lower spinal cord region. The virtual model 800 is a three-dimensional visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 800 only includes bony structures of the patient's anatomy, but in other embodiments may include additional structures, such as cartilage, soft tissue, vascular tissue, nervous tissue, etc.

FIG. 8B illustrates a virtual model display 850 (sometimes referred to herein as the "display 850") showing different views of the virtual model 800. The virtual model display 850 includes a three-dimensional view of the virtual model 800, one or more coronal cross-section(s) 802 of the virtual model 800, one or more axial cross section(s) 804 of the virtual model 800, and/or one or more sagittal cross-section(s) 806 of the virtual model 800. Of course, other views are possible and can be included on the virtual model display 850. In some embodiments, the virtual model 800 may be interactive such that a user can manipulate the orientation or view of the virtual model 800 (e.g., rotate, zoom, pan, etc.), change the depth of the displayed cross-sections, select and isolate specific bony structures, or the like. The user device can provide virtual model (or image) interaction via touch (e.g., via an electronic touchscreen of a computer, tablet, and/or smartphone), mouse, etc.

Figures 2, 9A:
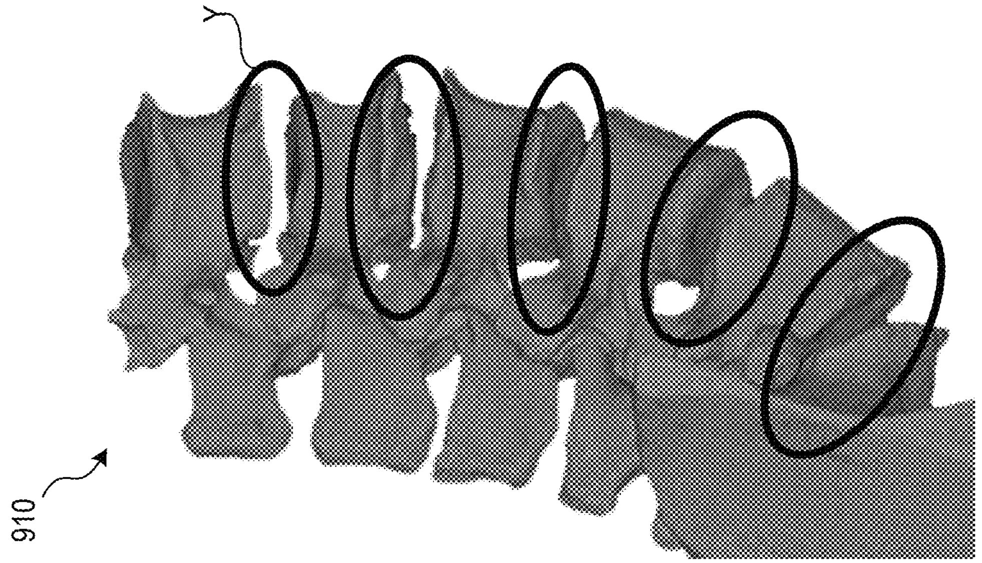
Figures 1, 9A:
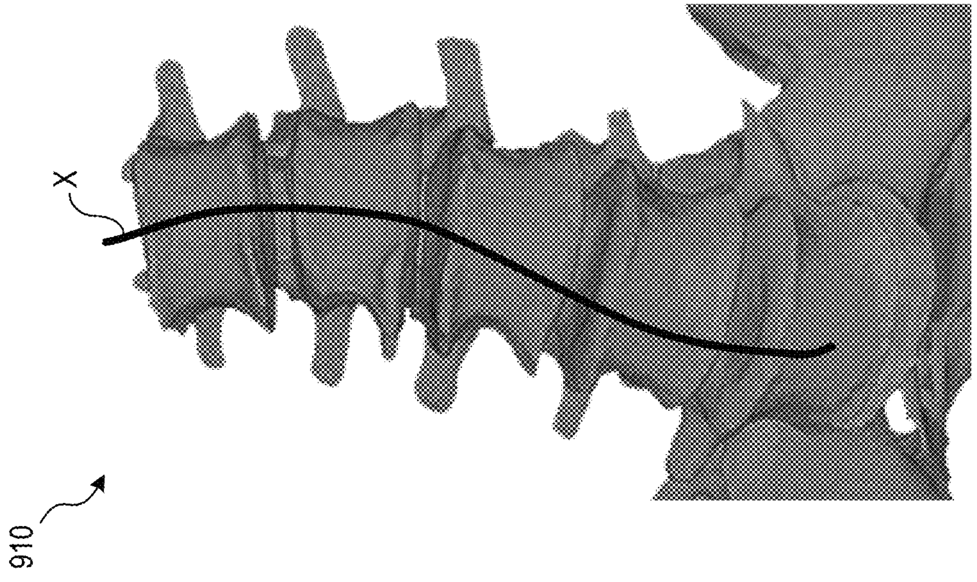
Figures 2, 9B:
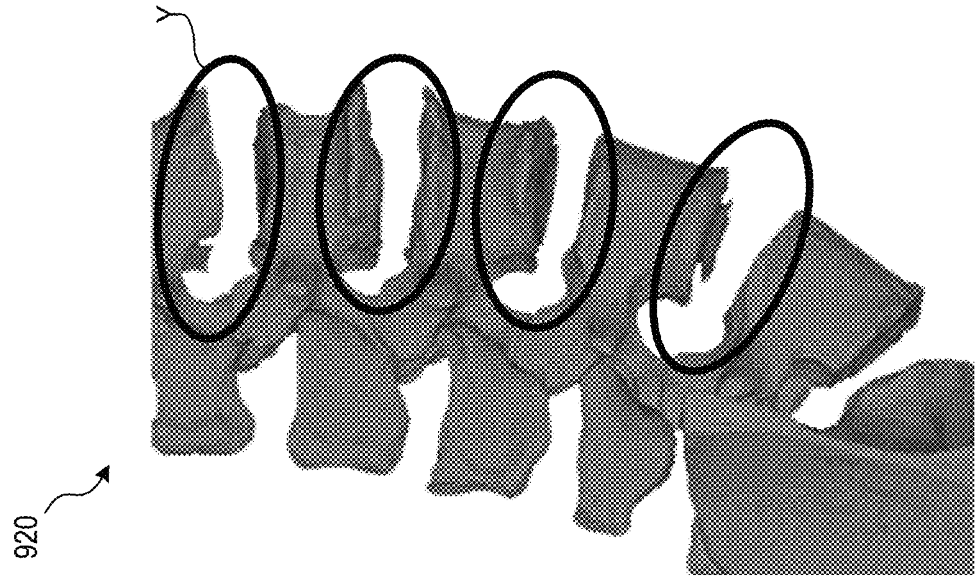
Figures 1, 9B:
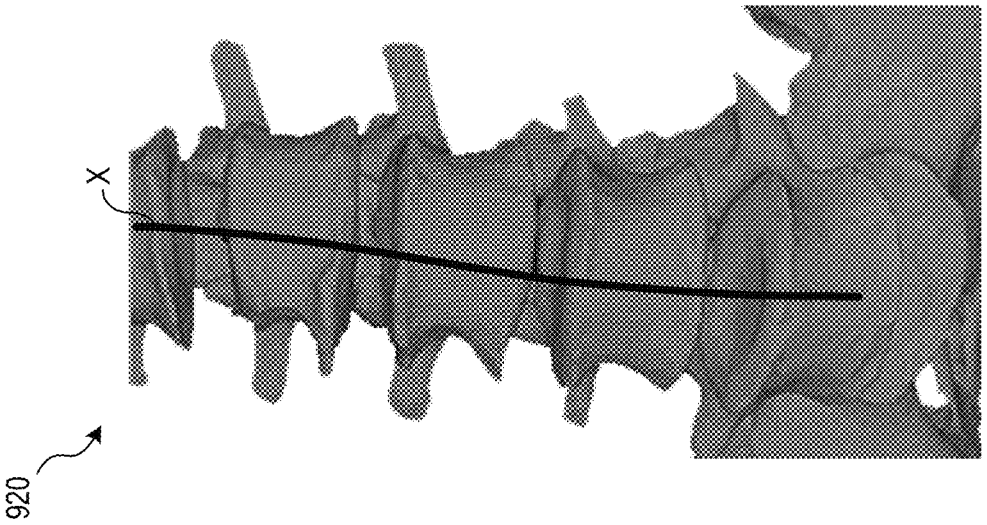

FIGS. 9A-1-9B-2 demonstrate an example of a virtual model of a patient's native anatomical configuration (e.g., as created in step 504 of process 500) and a virtual model of the patient's corrected anatomical configuration (e.g., as created in step 506 of the process 500). In particular, FIGS. 9A-1 and 9A-2 are anterior and lateral views, respectively, of a virtual model 910 showing a native anatomical configuration of a patient, and FIGS. 9B-1 and 9B-2 are anterior and lateral views, respectively, of a virtual model 920 showing the corrected anatomical configuration for the same patient. Referring first to FIG. 9A-1, the anterior view of the virtual model 910 illustrates the patient has abnormal curvature (e.g., scoliosis) of their spinal column. This is marked by line X, which follows a rostral-caudal axis of the spinal column. Referring next to FIG. 9A-1, the lateral view of the virtual model 910 illustrates the patient has collapsed discs or decreased spacing between adjacent vertebral endplates, marked by ovals Y. FIGS. 9B-1 and 9B-2 illustrate the corrected virtual model 920 accounting for the abnormal anatomical configurations shown in FIGS. 9A-1 and 9A-2. For example, FIG. 9B-1, which is an anterior view of the virtual model 920, illustrates the patient's spinal column having corrected alignment (e.g., the abnormal curvature has been reduced). This correction is shown by line X, which also follows a rostral-caudal axis of the spinal column. FIG. 9B-2, which is a lateral view of the virtual model 920, illustrates the patient's spinal column having restored disc height (e.g., increased spacing between adjacent vertebral endplates), also marked by ovals Y. The lines X and the ovals Y are provided in FIGS. 9A-1-9B-2 to more clearly demonstrate the correction between the virtual models 910 and 920, and are not necessarily included on the virtual models generated in accordance with the present technology.

FIG. 10 illustrates an example of a surgical plan 1000 (e.g., as generated in step 506 of process 500). The surgical plan 1000 can include pre-operative patient metrics 1002, predicted post-operative patient metrics 1004, one or more patient images (e.g., the patient images 703 received as part of the patient data set), the virtual model 910 (which can be the model itself or one or more images derived from the model) of the patient's native anatomical configuration (e.g., pre-operative patient anatomy), and/or the virtual model 920 (which can be the model itself or one or more images derived from the model) of the patient's corrected anatomical configuration (e.g., predicted post-operative patient anatomy). The virtual model 920 of the predicted post-operative patient anatomy can optionally include one or more implants 1012 shown as implanted in the patient's spinal cord region to demonstrate how patient anatomy will look following the surgery. Although four implants 1012 are shown in the virtual model 920, the surgical plan 1000 may include more or fewer implants 1012, including one, two, three, five, six, seven, eight, or more implants 1012.

The surgical plan 1000 can include additional information beyond what is illustrated in FIG. 10. For example, the surgical plan 1000 may include pre-operative instructions, operative instructions, and/or post-operative instructions. Operative instructions can include one or more specific procedures to be performed (e.g., PLIF, ALIF, TLIF, LLIF, DLIF, XLIF, etc.) and/or one or more specific targets of the operation (e.g., fusion of vertebral levels L1-L4, anchoring screw to be inserted in lateral surface of L4, etc.). Although the surgical plan 1000 is demonstrated in FIG. 10 as a visual report, the surgical plan 1000 can also be encoded in computer-executable instructions that, when executed by a processor connected to a computing device, cause the surgical plan 1000 to be displayed by the computing device. In some embodiments, the surgical plan 1000 may also include machine-readable operative instructions for carrying out the surgical plan. For example, the surgical plan can include operative instructions for a robotic surgical platform to carry out one or more steps of the surgical plan 1000.

Figure 11:
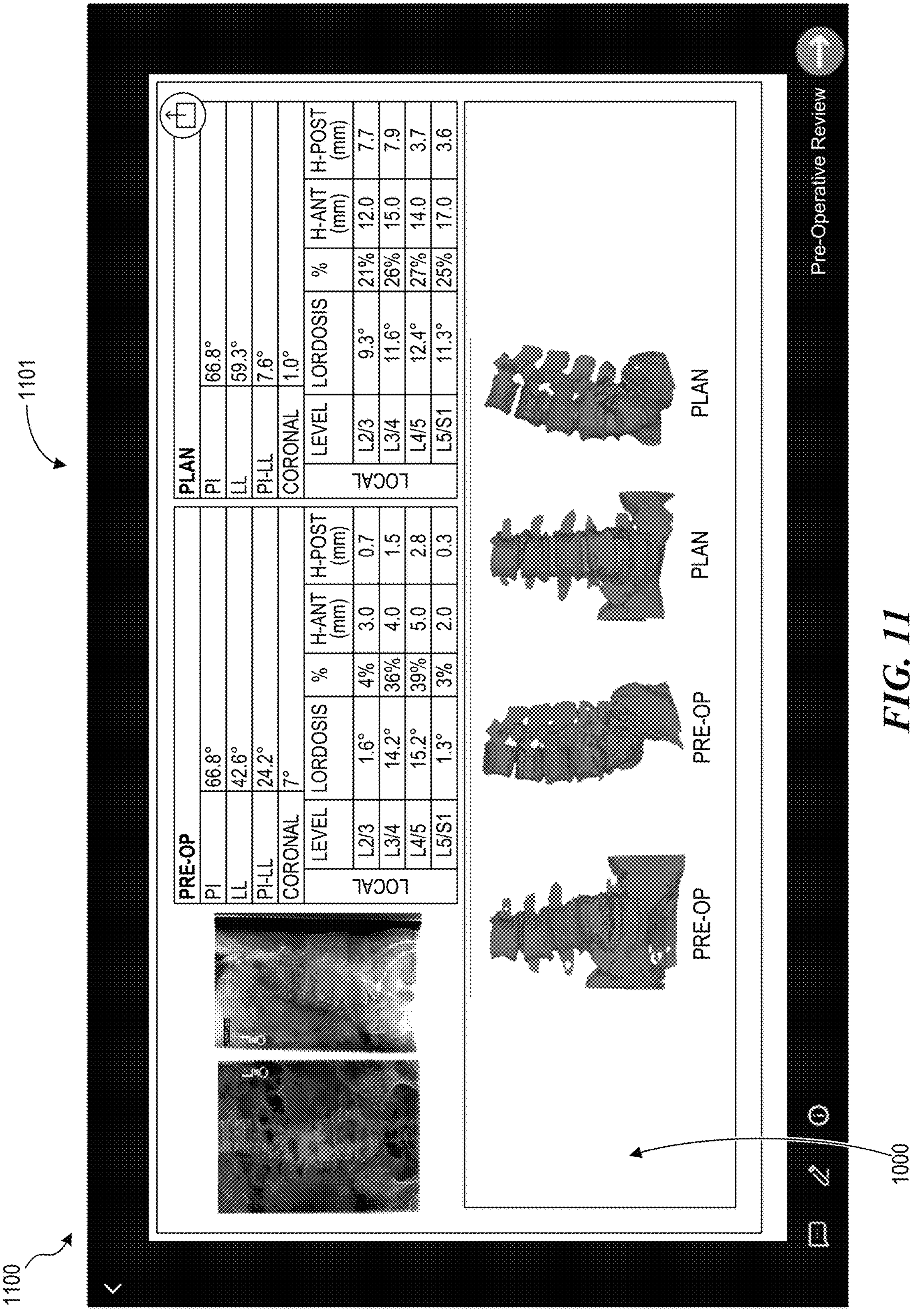
FIG. 11 illustrates an exemplary surgical plan report detailing the surgical plan shown in FIG. 10 for surgeon review and that may be used and/or generated in connection with the methods described herein, according to an embodiment.
Figure 11:
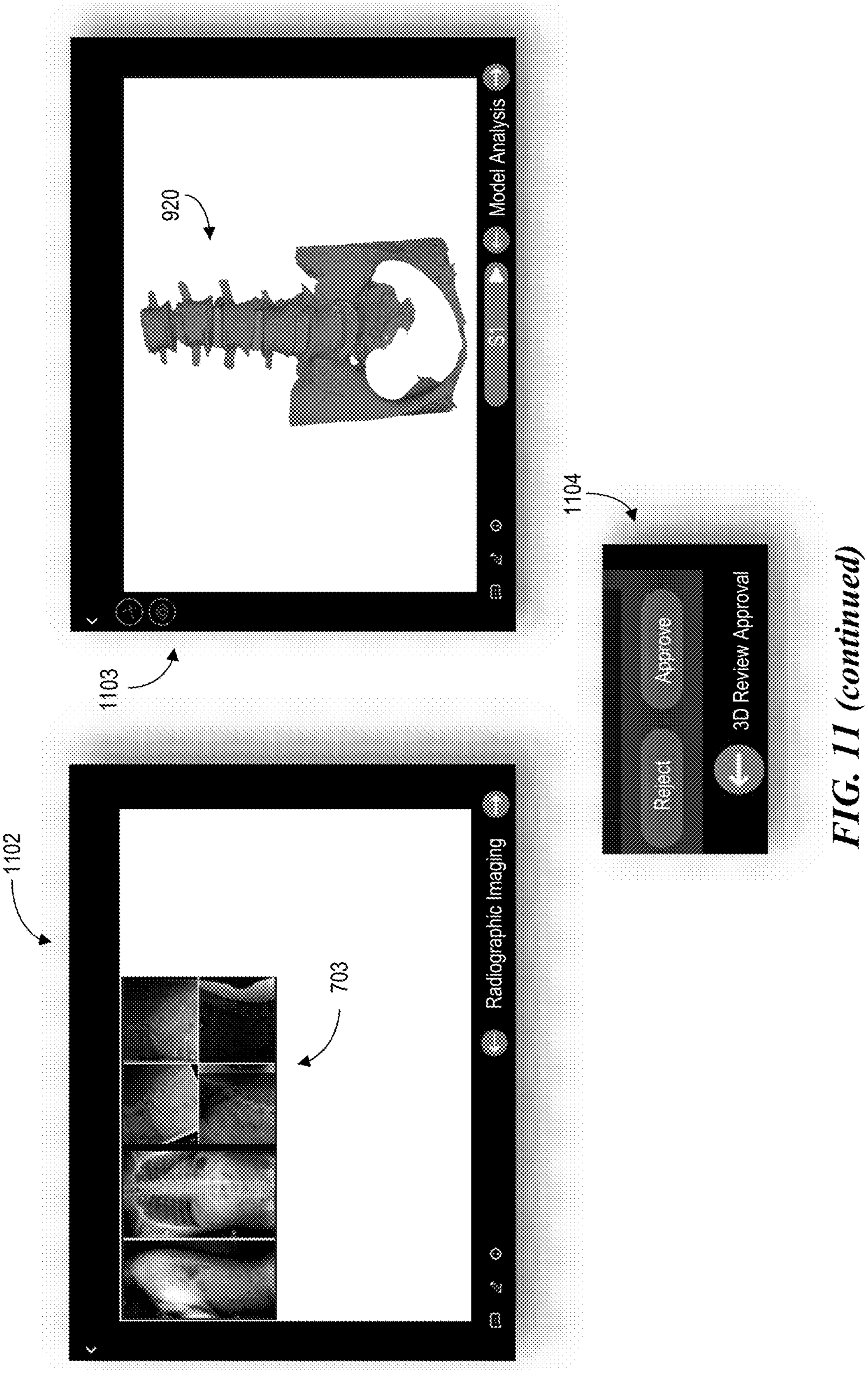

FIG. 11 provides a series of images illustrating an example of a patient surgical plan report 1100 that includes the surgical plan 1000 and that may be transmitted to a surgeon for review and approval. The surgical plan report 1100 can include a multi-page report detailing aspects of the surgical plan 1000. For example, the multi-page report may include a first page 1101 demonstrating an overview of the surgical plan 1000 (e.g., as shown in FIG. 10), a second page 1102 illustrating patient images (e.g., such as the patient images 703 received in step 502 and shown in FIG. 7D), a third page 1103 illustrating an enlarged view of the virtual model of the corrected anatomical configuration (e.g., the virtual model 920 shown in FIGS. 9B-1 and 9B-2), and a fourth page 1104 prompting the surgeon to either approve or reject the surgical plan 1000. The approval or rejection can be inputted via one or more displayed buttons (e.g., approval button of FIG. 11, reject button of FIG. 11, etc.). Of course, additional information about the surgical plan can be presented with the report 1100 in the same or different formats. In some embodiments, if the surgeon rejects the surgical plan 1000, the surgeon can be prompted to provide feedback regarding the aspects of the surgical plan 1000 the surgeon would like adjusted.

The patient surgical plan report 1100 can be presented to the surgeon on a digital display of a computing device (e.g., the client computing device 102 shown in FIG. 1). In some embodiments, the report 1100 is interactive and the surgeon can manipulate various aspects of the report 1100 (e.g., adjust views of the virtual model, zoom-in, zoom-out, annotate, etc.). However, even if the report 1100 is interactive, the surgeon generally cannot directly change the surgical plan 1000. Rather, the surgeon may provide feedback and suggested changes to the surgical plan 1000, which can be sent back to the computing system that generated the surgical plan 1000 for analysis and refinement. In other embodiments, the surgeon can directly change the surgical plan 1000. This allows the surgeon to directly control the design process.

Figure 12A:
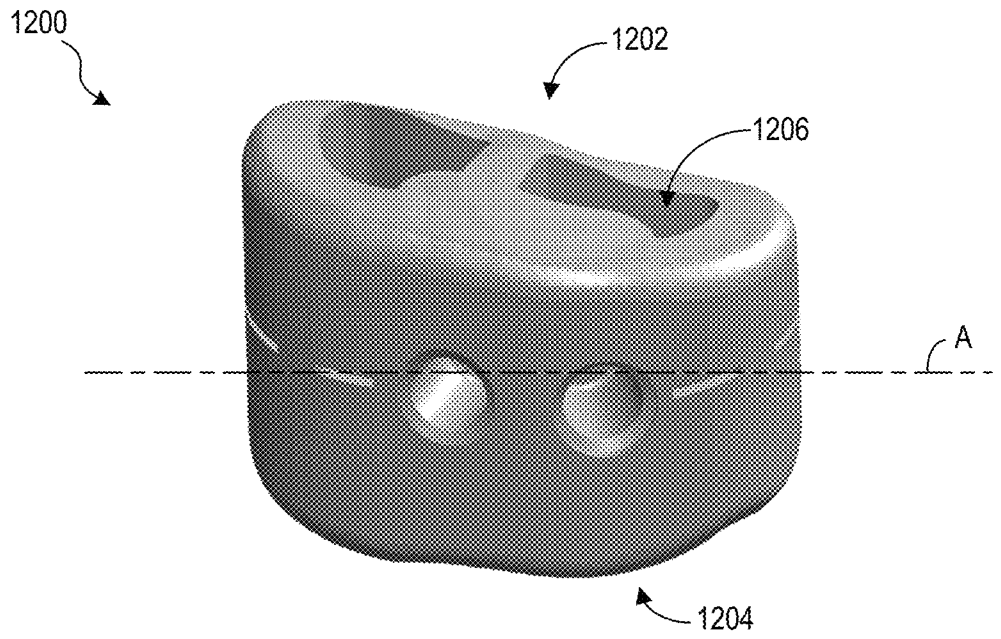
FIGS. 12A and 12B illustrate an exemplary patient-specific implant that can be used and/or generated in connection with the methods described herein, according to an embodiment.
Figure 12B:
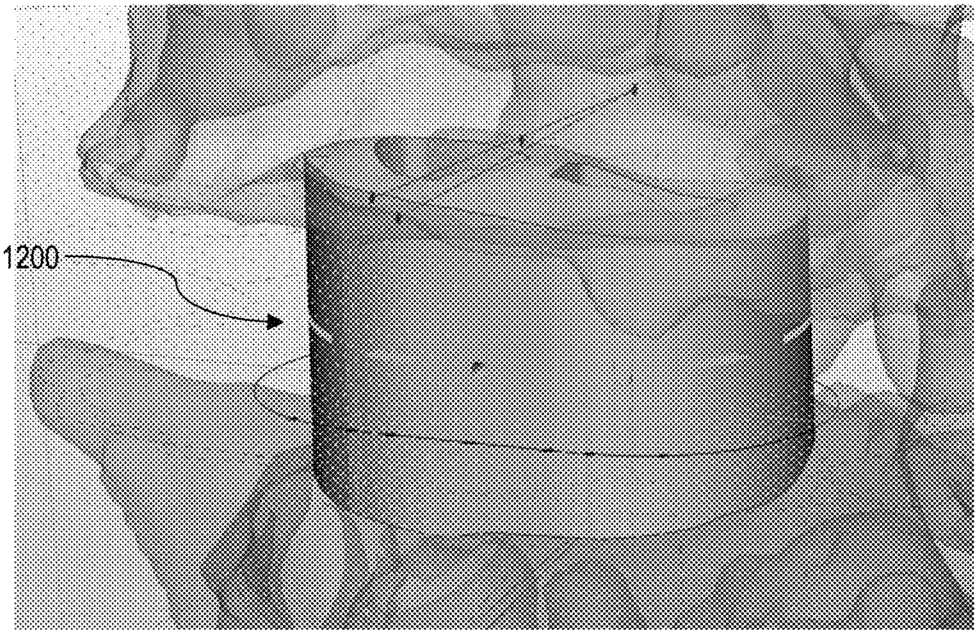

FIG. 12A illustrates an example of a patient-specific implant 1200 (e.g., as designed in step 508 and manufactured in step 512 of the process 500), and FIG. 12B illustrates the implant 1200 implanted in the patient. The implant 1200 can be any orthopedic or other implant specifically designed to induce the patient's body to conform to the previously identified corrected anatomical configuration. In the illustrated embodiment, the implant 1200 is a vertebral interbody device having a first (e.g., upper) surface 1202 configured to engage an inferior endplate surface of a superior vertebral body and a second (e.g., lower) surface 1204 configured to engage a superior endplate surface of an inferior vertebral body. The first surface 1202 can have a patient-specific topography designed to match (e.g., mate with) the topography of the inferior endplate surface of the superior vertebral body to form a generally gapless interface therebetween. Likewise, the second surface 1204 can have a patient-specific topography designed to match or mate with the topography of the superior endplate surface of the inferior vertebral body to form a generally gapless interface therebetween. The implant 1200 may also include a recess 1206 or other feature configured to promote bony ingrowth. Because the implant 1200 is patient-specific and designed to induce a geometric change in the patient, the implant 1200 is not necessarily symmetric, and is often asymmetric. For example, in the illustrated embodiment, the implant 1200 has a non-uniform thickness such that a plane defined by the first surface 1202 is not parallel to a central longitudinal axis A of the implant 1200. Of course, because the implants described herein, including the implant 1200, are patient-specific, the present technology is not limited to any particular implant design or characteristic. Additional features of patient-specific implants that can be designed and manufactured in accordance with the present technology are described in U.S. patent application Ser. Nos. 16/987,113; 17/100,396, the disclosures of which are incorporated by reference herein in their entireties.

Figure 13:
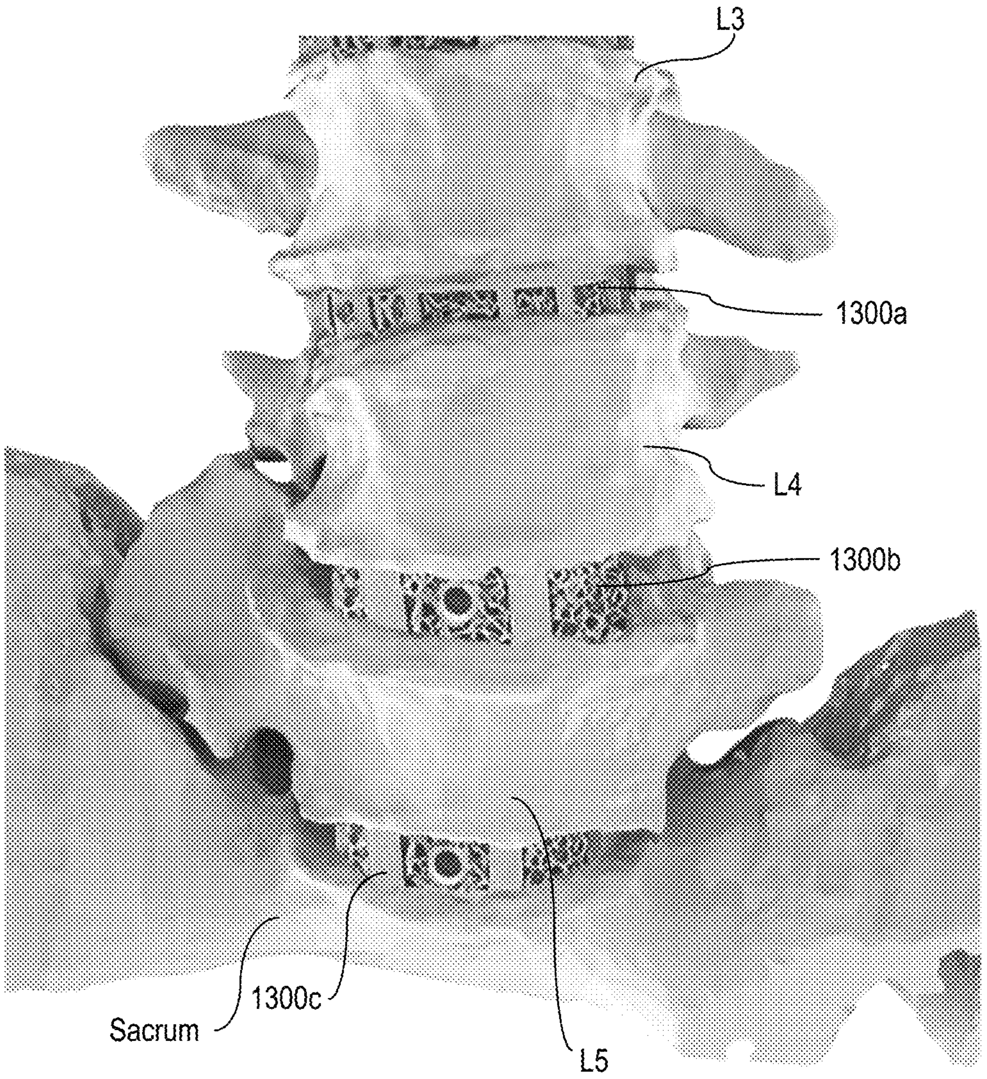
FIG. 13 illustrates a segment of a patient's spine after several patient-specific implants have been implanted therein, according to an embodiment.

The patient-specific medical procedures described herein can involve implanting more than one patient-specific implant into the patient to achieve the corrected anatomical configuration (e.g., a multi-site procedure). FIG. 13, for example, illustrates a lower spinal cord region having three patient-specific implants 1300*a*-1300*c* implanted at different vertebral levels. The implants 1300*a*-1300*c* can be similar to and include one or more features of the implant discussed in connection with FIGS. 2-3B. More specifically, a first implant 1300*a* is implanted between the L3 and L4 vertebral bodies, a second implant 1300*b* is implanted between the L4 and L5 vertebral bodies, and a third implant 1300*c* is implanted between the L5 vertebral body and the sacrum. Together, the implants 1300*a-c* can cause the patient's spinal cord region to assume the previously identified corrected anatomical configuration (e.g., transforming the patient's anatomy from its pre-operative diseased configuration to the post-operative optimized configuration). In some embodiments, more or fewer implants are used to achieve the corrected anatomical configuration. For example, in some embodiments one, two, four, five, six, seven, eight, or more implants are used to achieve the corrected anatomical configuration. In embodiments involving more than one implant, the implants do not necessarily have the same shape, size, or function. In fact, the multiple implants will often have different geometries and topographies to correspond to the target vertebral level at which they will be implanted. As also shown in FIG. 13, the patient-specific medical procedures described herein can involve treating the patient at multiple target regions (e.g., multiple vertebral levels).

In addition to designing patient-specific medical care based off reference patient data sets, the systems and methods of the present technology may also design patient-specific medical care based off disease progression for a particular patient. In some embodiments, the present technology therefore includes software modules (e.g., machine learning models or other algorithms) that can be used to analyze, predict, and/or model disease progression for a particular patient. The machine learning models can be trained based off multiple reference patient data sets that includes, in addition to the patient data described with respect to FIG. 1, disease progression metrics for each of the reference patients. The progression metrics can include measurements for disease metrics over a period of time. Suitable metrics may include spinopelvic parameters (e.g., LL, pelvic tilt, sagittal vertical axis (SVA), cobb angle, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.).

In some embodiments, the present technology includes a disease progression module that includes an algorithm, machine learning model, or other software analytical tool for predicting disease progression in a particular patient. The disease progression module can be trained based on reference patient data sets that includes patient information (e.g., age, sex, height, weight, activity level, diet) and disease metrics (e.g., diagnosis, spinopelvic parameters such as LL, pelvic tilt, SVA, cobb angle, coronal offset, etc., disability scores, functional ability scores, flexibility scores, VAS pain scores, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other healthcare provider, who can review and update the estimate, if necessary.

As a non-limiting example, a particular patient who is a fifty-five-year-old male may have an SVA value of 6 mm. The disease progression module can analyze patient reference data sets to identify disease progression for individual reference patients having one or more similarities with the particular patient (e.g., individual patients of the reference patients who have an SVA value of about 6 mm and are approximately the same age, weight, height, and/or sex of the patient). Based on this analysis, the disease progression module can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The systems and methods described herein can also generate models/simulations based on the estimated rates of disease progression, thereby modeling different outcomes over a desired period of time. Additionally, the models/simulations can account for any number of additional diseases or conditions to predict the patient's overall health, mobility, or the like. These additional diseases or conditions can, in combination with other patient health factors (e.g., height, weight, age, activity level, etc.) be used to generate a patient health score reflecting the overall health of the patient. The patient health score can be displayed for surgeon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physician input for review by the healthcare provider, patient, etc.

In some embodiments, the present technology can also predict, model, and/or simulate disease progression based on one or more potential surgical interventions. For example, the disease progression module may simulate what a patient's anatomy may look like 1, 2, 5, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected diseases progression.

Accordingly, in some embodiments, multiple disease progression models (e.g., two, three, four, five, six, or more) are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal intervention can also be fully or semi-automated, as described herein.

Based off of the modeled disease progression, the systems and methods described herein can also (i) identify the optimal time for surgical intervention, and/or (ii) identify the optimal type of surgical procedure for the patient. In some embodiments, the present technology therefore includes an intervention timing module that includes an algorithm, machine learning model, or other software analytical tool for determining the optimal time for surgical intervention in a particular patient. This can be done, for example, by analyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module can compare the disease metrics for a particular patient to the reference patient data sets to determine, for similar patients, the point of disease progression at which surgical intervention produced the most favorable outcomes.

As a non-limiting example, the reference patient data sets may include data associated with reference patients' SVA. The data can include (i) SVA values for individual patients over a period of time before surgical intervention (e.g., how fast and to what degree the SVA value changed), (ii) SVA of the individual patients at the time of surgical intervention, (iii) the change in SVA after surgical intervention, and (iv) the degree to which the surgical intervention was successful (e.g., based on pain, quality of life, or other factors). Based on the foregoing data, the intervention timing module can, based on a particular patient's SVA value, identify at which point surgical intervention will have the highest likelihood of producing the most favorable outcome. Of course, the foregoing metric is provided by way of example only, and the intervention timing module can incorporate other metrics (e.g., LL, pelvic tilt, SVA, cobb angle, coronal offset, disability scores, functional ability scores, flexibility scores, VAS pain scores) instead of or in combination with SVA to predict the time at which surgical intervention has the highest probability of providing a favorable outcome for the particular patient.

The intervention timing module may also incorporate one or more mathematical rules based on value thresholds for various disease metrics. For example, the intervention timing module may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a cobb angle of greater than 10 degrees, and/or a combination of cobb angle and LL/PI mismatch greater than 20 degrees. Of course, other threshold values and metrics can be used; the foregoing are provided as examples only and in no way limit the present disclosure. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module may provide an estimate for when the patient's metrics will exceed one or more thresholds, thereby providing the patient with an estimate of when surgical intervention may become recommended.

The present technology may also include a treatment planning module that can identify the optimal type of surgical procedure for the patient based on the disease progression of the patient. The treatment planning module can be an algorithm, machine learning model, or other software analytical tool trained or otherwise based on multiple reference patient data sets, as previously described. The treatment planning module may also incorporate one or more mathematical rules for identifying surgical procedures. As a non-limiting example, if a LL/PI mismatch is between 10 and 20 degrees, the treatment planning module may recommend an anterior fusion surgery, but if the LL/PI mismatch is greater than 20 degrees, the treatment planning module may recommend both anterior and posterior fusion surgery. As another non-limiting example, if a SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only and in no way limit the present disclosure.

Without being bound by theory, incorporating disease progression modeling into the patient-specific medical procedures described herein may even further increase the effectiveness of the procedures. For example, in many cases it may be disadvantageous operate after a patient's disease progresses to an irreversible or unstable state. However, it may also be disadvantageous to operate too early, before the patient's disease is causing symptoms and/or if the patient's disease may not progress further. The disease progression module and/or the intervention timing module can therefore help identify the window of time during which surgical intervention in a particular patient has the highest probability of providing a favorable outcome for the patient.

Figure 14:
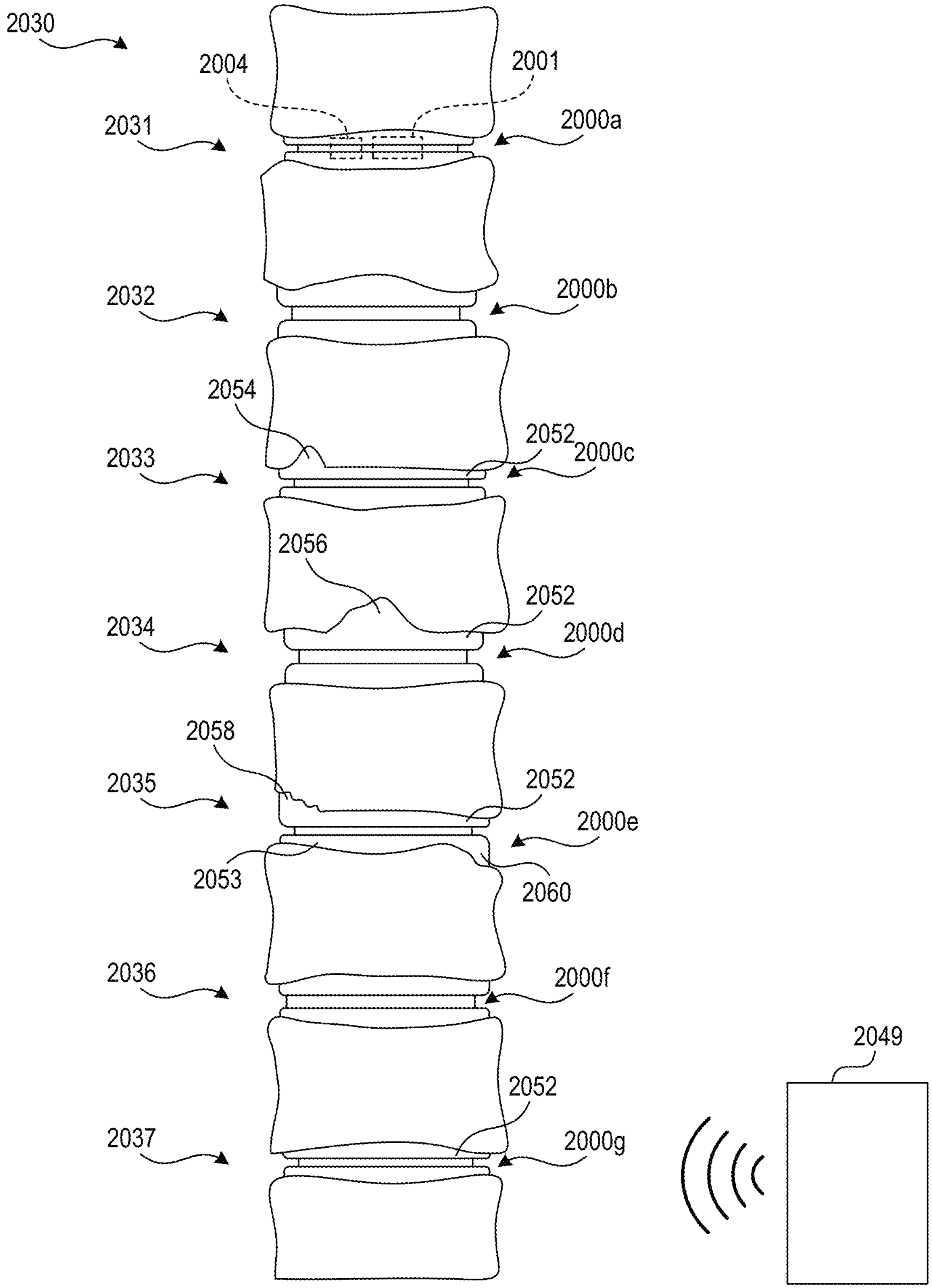
FIG. 14 shows a patient's spine and a remote device for controlling actuation of intervertebral implants, according to an embodiment.

FIG. 14 shows a patient's spine 2030 with intervertebral implants located at each individual level. The implants 2000*a-g* (collectively, "implants 2000") can be tailored to fit with anatomical features at the individual levels. Non-invasive post-operative spine adjustments can be performed by using inter-implant communications, a remote device or controller 2049 that controls actuation of the implants 2000, or combinations thereof. The inter-implant communications can be wireless communications via a network maintained by the implants 2000. The remote device 2049 can communicate wirelessly with selected implants or all of the implants. The implants 2000 can be the implants discussed in connection with FIGS. 2-4 or other implants disclosed herein.

An implant 2000*a* is implanted at a level 2031 with normal endplates free from any defect in the surface topology. The endplates of the implant 2000*a* can have convex shapes that match the illustrated concave endplates of the adjacent vertebrae at the level 2031. The implant 2000*a* can have an actuation mechanism 2001 that can be powered by an externally applied field (e.g., magnetic field or another field) provided by the remote device 2049. The actuation mechanism 2001 can include inductively rechargeable power sources, actuation elements, processors, transmitters/receivers, etc. The position, number, and capabilities of the actuation mechanisms (e.g., 2001 or 2004) can be selected based on the available adjustability (e.g., range expansion/contraction, drive force, etc.).

The remote device 2049 can communicate with one or more of the implants 2000. To install new software, the remote device 2049 can wirelessly transmit software to at least one of the implants 2000. The implants 200 can be programmed to wirelessly receive the software, install and run the received software, and/or wirelessly transmit to software to another one of the implants 2000. In some implementations, the remote device 2049 can communicate with the implants 2000 via a wireless protocol, including mesh protocols (e.g., Zigbee protocols, Z-wave protocols, etc.), ad-hoc Network protocols, etc. In some embodiments, the implants 2000 can receive a distribute over the air updates upon authorization. If the implants 2000 detect any adverse event, the implants 2000 can transmit a request for additional software or instructions. The remote device 2049 or another device can receive the request and in response transmit instructions, over-the-air updates, or the like based on the request. In some implementations, the remote device 2049 can be in the form of a smart phone, tablet, or computer that communicates with the implants 2000 via a local wireless connection, such as a Bluetooth connection, Wi-Fi connection, or the like.

The implants 2000 can have patient-specific features. An implant 2000*b* is implanted at a level 2032 with a severe concave shape in the superior and inferior vertebra. The implant 2000*b* has large convex contours that match the corresponding concave shape of the superior vertebra. An implant 2000*c* is implanted at a level 2033 with a superior endplate having a focal defect 2054 adjacent, but not on, a longitudinal side of the superior vertebra. The implant 2000*d* has an upper endplate 2052 with a contouring feature 2056 generally corresponding to the focal defect to better fit the superior endplate. Focal defects in a patient's spine can range from relatively small cavities (e.g., as shown at the level 2033) to relatively large valleys (e.g., as shown at the level 2034). Further, focal defects can include protrusions (not shown) where excess bone and/or cartilage is collected, requiring concave contouring features in the endplates of the implants to match them. An implant 2000*e* is implanted a level 2035 with corner defects in the superior and inferior vertebrae. Corner defects are located at least partially on longitudinal sides of the vertebrae. Corner defects can include missing corners that are cut off at varying angles, protrusions (not shown) at the corners, and/or rough topology at the corners (e.g., on the missing corner, on the protrusion, and/or on the otherwise normal surface of the corner). The implant 2000*e* has an upper endplate 2052 with a periphery contour 2058 configured to fit the corner defect in the superior endplate and a lower endplate 2053 with a periphery contour 2060 configured to fit the corner defect in the inferior endplate. Other adjacent levels, such as level 2036, can be formed by endplates with relatively smooth and planar or straight topologies. In such embodiments, an implant 2000*f* with relatively smooth contouring can be implanted at level 2036.

An implant 2000*g* is implanted at level 2037 with a superior vertebra having erosive defects on the inferior surface of the superior vertebra. The external device 2049 can command the implant 2000*g* to move to a target position. As illustrated, erosive defects can span the entire surface of a vertebra and include multiple valleys and peaks therein. In some patients, erosive defects can be contained to a focal region and/or a corner region of a surface. In some patients, erosive defects can include one or more deep valleys and/or one or more tall peaks. As illustrated, the implant 2000*g* can have an upper endplate 2052 configured to mate with the erosive defects in the superior vertebra.

FIG. 15 illustrates an exemplary corrective plan 2100 for a patient-specific surgical procedure that may be used and/or generated in connection with the methods described herein, according to an embodiment. The corrective plan 2100 can be an adjustable-implant corrective plan that incorporates all or some of surgical plans or other plans disclosed herein. The corrective plan 2100 can include, without limitation, intra- and/or pre-operative patient metrics (e.g., pre-operative patient metrics 1002 discussed in connection with FIGS. 10-13), predicted post-operative patient metrics (e.g., predicted post-operative patient metrics 1004 discussed in connection with FIGS. 10-13), adjustment metrics 2110, and adjustment configurations (e.g., adjustment configurations of implants, adjustment configurations of anatomy, spinal adjustment configurations, etc.).

The adjustment metrics 2110 can include any number of planned adjustments to an adjustable spinal implant. The illustrated corrective plan 2100 includes planned adjustments 2120*a*, 2120*b*, 2120*c* (collectively "adjustments 2120"). Each adjustment 2120 can include associated post-adjustment metrics reviewable by the physician. For example, the physician can review and approve these metrics by selecting an approve button, design implant button, or the like. The computing system can then design the adjustable implants based on the approved adjustment (e.g., design the adjustable implant to have an adjustable range of motion capable of accommodating the approved adjustment (s)). If the physician wants to modify adjustments, the physician can select the modify button. The physician can then input one or more parameters or metrics for adjustment. The computing system can update the spinal model accordingly to the inputted parameters or metrics. Arrows can (e.g., arrows 2130*a*, 2130*b*, 2130*c*) indicate adjustments, such as range of motion, adjustment values, etc. In some environments, the arrows 2130*a-b* and/or metrics 2120*a* can indicate degrees of freedom and ranges of motion for specific implants. A user can modify or approve the adjust ability of the implant based on the arrows. Adjustments 2 and 3 include adjustment indicators (illustrated as arrows) showing planned adjustments, such as the adjustments discussed in connection with FIGS. 16A-16D. The physician can approve/select individual target intra-operative configurations and/or post-operative configurations for different loading conditions.

The planned adjustments 2120*a*, 2120*b*, 2120*c* can include configurations for the implantable patient-devices capable of autonomously operating in a coordinate manner to position anatomical elements of the patient to achieve target anatomical configurations. The patient-devices can detect at least one value and then determine an anatomical adjustment based on the detected at least one value and the corrective plan. The values can be inputted by a user or from the corrective plan. One or more of the patient-devices can change configurations to provide the determined anatomical adjustment. The corrective plan (or a portion thereof) 2110 be transmitted to implants. The corrective plan 2110 can include protocols for discover devices, determined communication details, exchange data, process data, or the like. This allows newly available devices to join the intrabody wireless network. The implants can discover other implants for networking purposes and use predetermined protocols for discovery. For example, if a new device is implanted in or coupled to the patient, another implant can discover the newly available device. The implant can perform the discovery routine to authenticate and allow the newly available device to join the network.

Figure 16A:
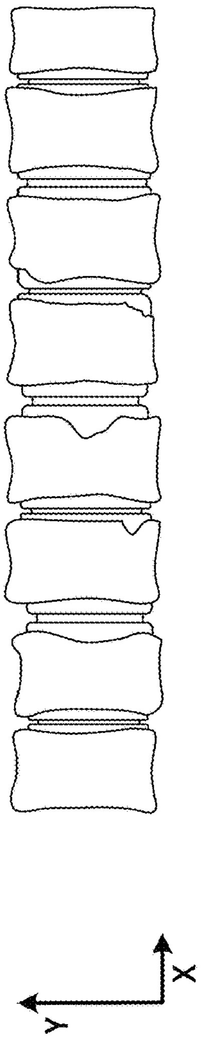
FIGS. 16A-16D show a patient's spine in different configurations, according to an embodiment.
Figure 16B:
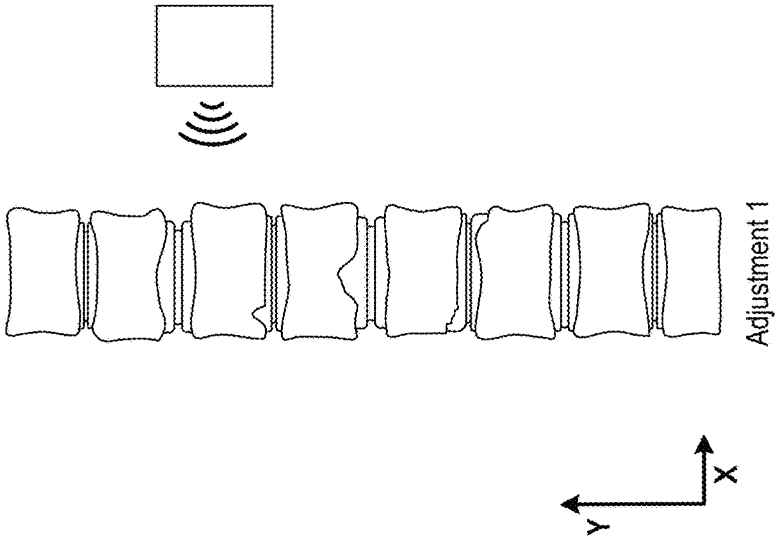
Figure 16C:
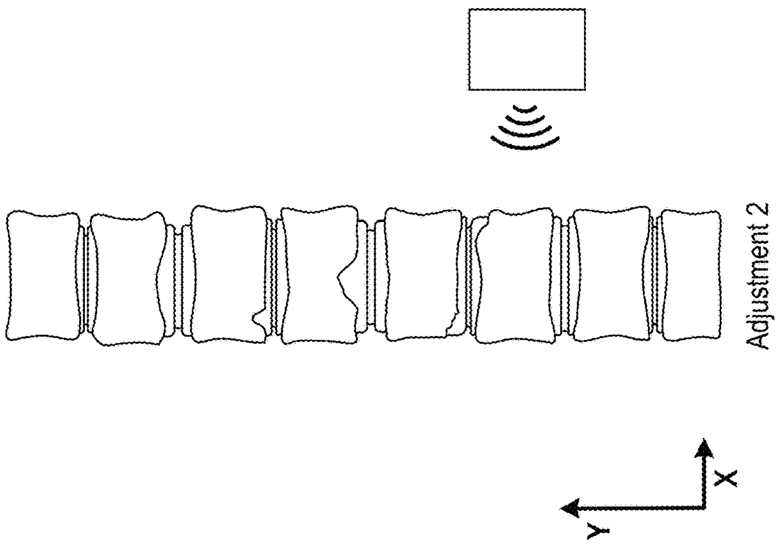
Figure 16D:
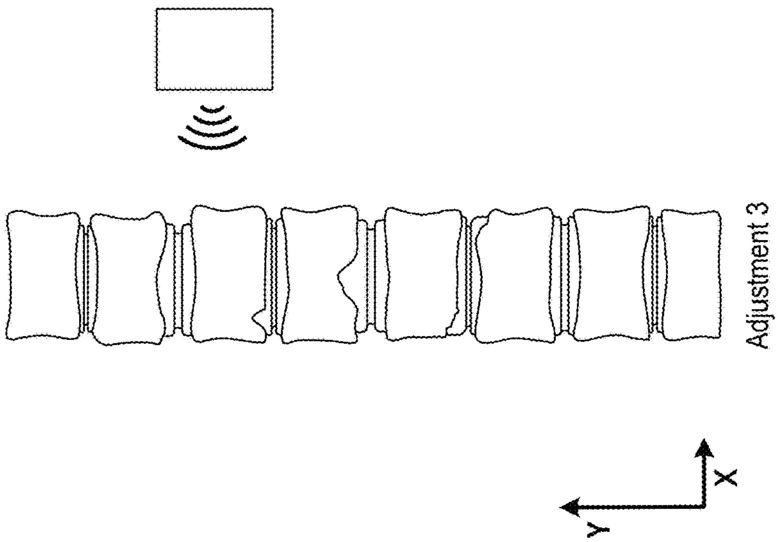

FIGS. 16A-16D show a patient's spine in different orientations resulting in different loading of implants. FIG. 16A shows the patient's spine in a generally horizontally orientation. For example, the implants can be implanted when the patient's body is generally horizontal so that the spine is generally unloaded. During surgery, it may be difficult to determine how loading of spine will compare to the predicted loading. Accordingly, the implants can be reconfigured post-operatively to move the spine to a target post-operative configuration. FIGS. 16B-16D show adjustment for the post-operative patient's spine in a vertical orientation (e.g., sitting or standing), although post-operative adjustments can also be performed with the patient in other orientations. This allows for post-operative adjustments based on post-operative loading, dynamic visualization, etc. Each of the implants can monitor loading and communicate with other implants to determine, for example, loading along a spinal segment, multi-level loading relationships, and other parameters disclosed herein. Example parameters include intervertebral gap height, lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.), pelvic parameters, or combinations thereof.

In spinal fusion procedures, implants can be adjusted shortly after surgery (e.g., hours, days, etc.) to position at vertebrae for fusion. In spinal alignment procedures, the implants can be vertebral discs adjusted periodically to compensate for patient improvement, disease progression, etc. For example, Adjustments 1-3 of FIGS. 16B-16D can be performed monthly, yearly, or at physician determined intervals. The number of adjustment sessions, period between adjustment sessions, and alterations to the spine can be selected based on a treatment plan, patient recovery, or the like. For example, the system of FIG. 1 and computer device of FIG. 2 can be used to generate correction and adjustments plans. For example, a computer system can be used to determine a corrected anatomical configuration of a patient for achieving a target treatment outcome. The computer system can predict disease progression for a disease affecting the patient's spine based on a patient data set of a patient using at least one machine learning model. The computer system can identify the actuatable implant configured to be implanted in the patient to achieve the corrected anatomical configuration. The actuatable implant is movable between multiple configurations to compensate for the predicted disease progression based on the target treatment outcome. The at least one machine learning model can determine whether to reconfigure the at least one device based on post-adjustment images. The post-adjustment images can include dynamic sit/stand x-ray images, and in some adjustment procedures, the spine can be visualized (e.g., using fluoroscopy) while invasively or non-invasively actuating the actuatable implant.

In some embodiments, one or more anatomical corrections for the patient are generated based on pre-adjustment images and a patient-specific pre-surgical correction plan. A computer system can generate a series of corrected anatomical models representing anatomical changes over a period of time based on a patient-specific correction to the native anatomy and a predicted disease progression. The corrected anatomical models can be viewed and modified by a user as part of the pre-surgical correction plan. The pre-surgical correction plan can be generated by comparing a patient data set to a plurality of reference patient data sets to identify one or more similar patient data sets in the plurality of reference patient data sets, and each similar patient data set corresponds to a reference patient that (a) has similar spinal pathology data as the patient and/or (b) received treatment with an post-operative adjustable orthopedic implant. In some embodiments, a virtual model of the spine is generated. The predicted disease progression using the virtual model. An actuatable implant can be designed to fit the virtual model throughout the predicted disease progression. Simulations can be modified and rerun based on the post-operative adjustments (see FIGS. 16A-16D). Additional implants configured to cooperate with the actuatable implant can be designed to achieve the target treatment outcome and be configured for multi-level adjustments. The plans disclosed herein an provide results (e.g., analytics for each level, overall spine correction score, etc.) from simulations of the multi-level adjustments.

The networked systems and devices disclosed herein can include a data storage element storing patient-specific data, a retrieval feature for accessing patient-specific data, or the like. A data storage module having a memory storing data and a retrieval module configured to transmit the patient-specific surgical plan from the data storage module to a surgical platform can be configured to execute one or more aspects of the patient-specific surgical plan. Patient-specific data is therefore linked to the patient-specific implant. Data can be accessed after the implant is implanted. Data can be used to confirm aspects of the implant/surgery (e.g., is the implant correctly positioned) and be combined, aggregated, and analyzed with post-implantation data (e.g., state of implant data, configuration data, sensor data, etc.). U.S. application Ser. No. 16/990,810 discloses features, systems, devices, materials, and methods that can be incorporated into or used with the networked systems and devices disclosed herein. U.S. application Ser. No. 16/990,810 is incorporated herein by reference in its entirety.

In some embodiments, the present technology can also predict, model, and/or simulate disease progression. For example, a disease progression module may simulate what a patient's anatomy may look like one, two, five, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected diseases progression. The networked systems and devices can generate data to monitor and predict disease progression. In some embodiments, one or more of the implantable devices includes a disease progression module for local analysis of data. In other embodiments, a remote computing device can include the disease progression module. As the implanted networked systems adjust corrections, the disease progression module can continuously or periodically predict disease progression.

The systems disclosed herein can also include multiple disease progression models (e.g., two, three, four, five, six, or more) that are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal adjustments can also be fully or semi-automated, as described herein. The implanted networked system can be programmed with the multiple disease progression models. The disease progression models can be modified based on the collected data and healthcare provider, etc.

In some embodiments, networked implants can be used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, or orthopedic trauma. The implants can dynamically correct for irregular spinal curvature, such as scoliosis, lordosis, or kyphosis (hyper- or hypo-), and irregular spinal displacement (e.g., spondylolisthesis). As such, corrections can be varied over time to compensate for disease progress and growth of the patient (e.g., devices implanted when patient is not fully grown, etc.). The networked devices can be designed to treat osteoarthritis, lumbar degenerative disk disease or cervical degenerative disk disease, lumbar spinal stenosis, or cervical spinal stenosis.

The networked systems and devices disclosed herein can include a data storage element storing patient-specific data, a retrieval feature for accessing patient-specific data, or the like. A data storage module having a memory storing data and a retrieval module configured to transmit the patient-specific surgical plan from the data storage module to a surgical platform can be configured to execute one or more aspects of the patient-specific surgical plan. Patient-specific data is therefore linked to the patient-specific implant. Data can be accessed after the implant is implanted. Data can be used to confirm aspects of the implant/surgery (e.g., is the implant correctly positioned) and be combined, aggregated, and analyzed with post-implantation data (e.g., state of implant data, configuration data, sensor data, etc.). U.S. application Ser. No. 16/990,810 discloses features, systems, devices, materials, and methods that can be incorporated into or used with the networked systems and devices disclosed herein. U.S. application Ser. No. 16/990,810 is incorporated herein by reference in its entirety.

In some embodiments, the present technology can also predict, model, and/or simulate disease progression. For example, a disease progression module may simulate what a patient's anatomy may look like one, two, five, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected diseases progression. The networked systems and devices can generate data to monitor and predict disease progression. In some embodiments, one or more of the implantable devices includes a disease progression module for local analysis of data. In other embodiments, a remote computing device can include the disease progression module. As the implanted networked systems adjust corrections, the disease progression module can continuously or periodically predict disease progression.

The systems disclosed herein can also include multiple disease progression models (e.g., two, three, four, five, six, or more) that are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal adjustments can also be fully or semi-automated, as described herein. The implanted networked system can be programmed with the multiple disease progression models. The disease progression models can be modified based on the collected data and healthcare provider, etc.

As one skilled in the art will appreciate, any of the software functions described previously may be combined or distributed into one or more software functions or devices for performing the operations described herein. Accordingly, any of the operations described herein can be performed by any of the computing devices or systems described herein, unless expressly noted otherwise.

The networked implants can be used to correct numerous different maladies in a variety of contexts including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. The implants can dynamically correct for irregular spinal curvature, such as scoliosis, lordosis, or kyphosis (hyper- or hypo-), and irregular spinal displacement (e.g., spondylolisthesis). As such, corrections can be varied over time to compensate for disease progress and growth of the patient (e.g., devices implanted when patient is not fully grown, etc.). The networked devices can be designed to treat osteoarthritis, lumbar degenerative disc disease or cervical degenerative disc disease, lumbar spinal stenosis, and cervical spinal stenosis. The networked implants can be orthopedic implants (e.g., artificial hips, fracture repair structures, alignment inserts, spinal-assistance structures, corresponding attachment mechanisms, etc.), sensory/neurological implants, replacement organs, assistive mechanisms (e.g., pacemakers, defibrillators, valves, stents), or the like. Other devices, such as attachable or wearable devices (e.g., blood glucose monitors, heart monitors, etc.), may be attached to or worn on the patient body for significant durations. Still other devices (e.g., personal devices, such as mobile phones, smart watches, and/or other personal health monitors) may be carried by the patient or within a fixed distance from the patient for significant portions of each day. These devices can be part of the network.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A computer-implemented method for designing a patient-specific lumbar implant based on modeled anatomical changes, the method comprising:
   receiving patient data, the patient data including:
      image data of a spinal region of a patient, including at least portions of a lumbar spine, a thoracic spine, and a cervical spine of the patient;
      generating a virtual three-dimensional model of the spinal region based on the image data, the virtual three-dimensional model including the at least portions of the lumbar spine, the thoracic spine, and the cervical spine;
   virtually simulating changes along a spine of the patient caused by implantation of a patient-specific lumbar implant by:
      determining one or more lumbar anatomical changes to the lumbar spine to provide a corrective adjustment based on at least one patient-specific lumbar implant that is virtually implanted along the lumbar spine in the virtual three-dimensional model;
      determining one or more anatomical changes to at least one of the thoracic spine or the cervical spine of the patient are acceptable, wherein the one or more anatomical changes are caused by the one or more lumbar anatomical changes; and
   designing the patient-specific lumbar implant configured to provide the corrective adjustment when implanted in the patient.
2. The computer-implemented method of example 1, further comprising:
   modifying the virtual three-dimensional model according to one or more predetermined relationships between (A) the thoracic spine or the cervical spine and (B) the lumbar spine; and
   determining one or more anatomical changes based on the modified virtual three-dimensional model.
3. The computer-implemented method of any of examples 1-2, further comprising:
   modeling, in the virtual three-dimensional model, the thoracic spine or the cervical spine as a singular anatomical structure; and
   determining changes to the singular anatomical structure based on a position of the thoracic spine relative to the corrective adjustment to the lumbar spine.
4. The computer-implemented method of any of examples 1-3, further comprising:
   simulating a range of motion by the patient; and
   determining whether the corrective adjustment to the lumbar spine increases the range of motion by the patient.
5. The computer-implemented method of any of examples 1-4, further comprising:
   simulating an anatomical alignment of the at least portions of the lumbar spine, the thoracic spine, and the cervical spine the patient; and
   determining whether the corrective adjustment to the lumbar spine impacts anatomical alignment of the cervical spine or the thoracic spine.
6. The computer-implemented method of any of examples 1-5, further comprising:
   receiving patient pain data;
   determining one or more adjustments to the virtual three-dimensional model of a spinal anatomy of the patient based at least partially on the received patient pain data; and
   determining a pain reduction score based on the one or more adjustments.
7. The computer-implemented method of any of examples 1-6, further comprising:
   analyzing the virtual three-dimensional model to determine a mobility score and a pain score for the patient based on the corrective adjustment.
8. The computer-implemented method of any of examples 1-7, wherein analyzing the virtual three-dimensional model includes using a trained machine learning model, wherein the machine learning model was trained based on previous patient virtual models, pain scores, and surgical outcomes.

9. The computer-implemented method of any of examples 1-8, further comprising:
generating a report based on simulated changes along the spine of the patient caused by implantation of a patient-specific implant virtually in the virtual three-dimensional model,
wherein the report includes predictions, modeling, simulations, and/or anatomical effects resulting from the corrective adjustment to the lumbar spine.

10. The computer-implemented method of any of examples 1-9, further comprising:
simulating a spinal load transfer via the lumbar spine to one or more adjacent anatomical features of the patient; and
modifying the lumbar spine to be in a predetermined anatomical configuration to adjust the one or more adjacent anatomical features to predetermined configurations.

11. The computer-implemented method of any of examples 1-10, further comprising:
determining one or more muscle or tissue anatomical changes based on the corrective adjustment to the spine.

12. A computing system comprising:
one or more processors; and
one or more memories storing instructions that, when executed by the one or more processors, cause the computing system to perform a process of any one of methods in claims 1-11.

13. A non-transitory computer-readable medium storing instructions that, when executed by a computing system, cause the computing system to perform operations of any one of methods in claims 1-11.

14. An patient-specific implant made by a process of any one of methods in claims 1-11.

26. A computer-implemented method comprising:
displaying, via at least one user device, a virtual three-dimensional model of a spinal region of a patient based on image data of the patient, the virtual three-dimensional model including at least portions of a lumbar spine, a thoracic spine, and a cervical spine of the patient;
displaying, via the at least one user device, virtually simulated changes along a spine of the patient caused by implantation of a patient-specific lumbar implant by:
determining one or more lumbar anatomical changes to the lumbar spine to provide a corrective adjustment based on at least one patient-specific lumbar implant that is virtually implanted along the lumbar spine in the virtual three-dimensional model;
determining one or more anatomical changes to at least one of the thoracic spine or the cervical spine of the patient are acceptable, wherein the one or more anatomical changes are caused by the one or more lumbar anatomical changes; and
sending approval from the at least one user device for designing a patient-specific lumbar implant configured to provide the corrective adjustment when implanted in the patient.

27. The computer-implemented method of example 26, further comprising:
displaying, via the at least one user device, a modification of the virtual three-dimensional model according to one or more predetermined relationships between (A) the thoracic spine or the cervical spine and (B) the lumbar spine; and
displaying, via the at least one user device, one or more anatomical changes based on the modified virtual three-dimensional model.

28. The computer-implemented method of any of examples 26-27, further comprising:
displaying, via the at least one user device, an interactive report configured to allow a user to zoom-in, zoom-out, and/or annotate one or more images and/or the virtual three-dimensional model.

29. The computer-implemented method of any of examples 26-28, wherein the at least one user device includes one or more electronic touch screens for displaying the interactive report.

30. The computer-implemented method of any of examples 26-29, further comprising:
sending patient pain data to a remote system; and
displaying a report from the remote system, the report including one or more adjustments to the virtual three-dimensional model of a spinal anatomy of the patient based at least partially on the patient pain data, and the report including a pain reduction score based on the one or more adjustments.

31. The computer-implemented method of any of examples 26-30, further comprising:
displaying, via the at least one user device, a report based on simulated changes along the spine of the patient caused by implantation of a patient-specific implant virtually in the virtual three-dimensional model,
wherein the report includes predictions, modeling, simulations, and/or anatomical effects resulting from the corrective adjustment to the lumbar spine.

32. The computer-implemented method of any of examples 26-31, wherein the report is linked to an account for the patient managed by a remote system, wherein the remote system is programmed to
simulate a spinal load transfer via the lumbar spine to one or more adjacent anatomical features of the patient; and
modify the lumbar spine to be in a predetermined anatomical configuration to adjust the one or more adjacent anatomical features to predetermined configurations.

33. The computer-implemented method of any of examples 26-32, further comprising receiving a notification that one or more relationships between anatomical adjustments and a far anatomical effects have been determined for the patient based on at least one simulation of implantation of the patient-specific lumbar implant.

34. A computer-implemented method comprising:
inputting a patient data of a patient set into at least one trained machine-learning model to cause the at least one trained machine-learning model to:
identify far anatomical effects caused by anatomical adjustments at a surgical site, wherein the far anatomical effects are remote from the surgical site; and
determine one or more relationships between the anatomical adjustments and the far anatomical effects; and
in response to determining the one or more relationships, send a notification to a user.

35. The computer-implemented method of example 34, further comprising:
analyzing, by the at least one trained machine-learning model, a pre-operative data set and a post-operative reference data set to obtain predicted far anatomical effects for planned anatomical adjustments for the patient,
wherein the far anatomical effects include bony misalignment, nerve compression, and/or an adverse effect in at least one region away from a surgical target.
36. A computer-implemented method comprising:
training at least one trained machine-learning model using reference data sets with far anatomical effects remote from surgical sites; and
inputting a patient data set into the at least one trained machine-learning model to cause the at least one trained machine-learning model to:
identify one or more biomechanical relationships between an anatomical adjustment at a site and at least one far anatomical element of a patient;
predict one or more far anatomical effects caused by the anatomical adjustment and the identified one or more biomechanical relationships; and
modifying the anatomical adjustment to account for the one or more far anatomical effects.
37. The computer-implemented method of example 36, further comprising retraining the at least one trained machine-learning model to adjust the modifying of the anatomical adjustment and/or modify the predicted one or more far anatomical effects.
38. A computer-implemented method for designing a patient-specific implant based on modeled anatomical changes, the method comprising:
receiving patient data, the patient data including:
image data of a spinal region of a patient, including at least portions of a lumbar spine, a thoracic spine, and a cervical spine of the patient;
generating a virtual three-dimensional model of the spinal region based on the image data, the virtual three-dimensional model including the at least portions of the lumbar spine, the thoracic spine, and the cervical spine;
based on the virtual three-dimensional model, determining one or more anatomical changes to the spinal region based on the patient-specific implant providing a corrective adjustment to at least one portion of the spinal region, wherein the one or more anatomical changes impact one or more of the lumbar spine, the thoracic spine, or the cervical spine; and
designing the patient-specific implant configured to provide the corrective adjustment when implanted in the patient.
39. A computing system comprising:
one or more processors; and
one or more memories storing instructions that, when executed by the one or more processors, cause the computing system to perform a process of any one of methods in examples 26-38.
40. A non-transitory computer-readable medium storing instructions that, when executed by a computing system, cause the computing system to perform operations of any one of methods in examples 26-38.
41. A patient-specific implant made by a process of any one of methods in examples 26-38.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES";

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";

U.S. application Ser. No. 16/207,116, filed on Dec. 1, 2018, titled "SYSTEMS AND METHODS FOR MULTI-PLANAR ORTHOPEDIC ALIGNMENT";

U.S. application Ser. No. 16/352,699, filed on Mar. 13, 2019, titled "SYSTEMS AND METHODS FOR ORTHOPEDIC IMPLANT FIXATION";

U.S. application Ser. No. 16/383,215, filed on Apr. 12, 2019, titled "SYSTEMS AND METHODS FOR ORTHOPEDIC IMPLANT FIXATION";

U.S. application Ser. No. 16/569,494, filed on Sep. 12, 2019, titled "SYSTEMS AND METHODS FOR ORTHOPEDIC IMPLANTS";

U.S. Application No. 62/773,127, filed on Nov. 29, 2018, titled "SYSTEMS AND METHODS FOR ORTHOPEDIC IMPLANTS";

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS";

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";

U.S. application Ser. No. 17/678,874, filed Feb. 23, 2022, titled "NON-FUNGIBLE TOKEN SYSTEMS AND METHODS FOR STORING AND ACCESSING HEALTHCARE DATA";

U.S. application Ser. No. 17/085,564, filed Oct. 30, 2020, titles "SYSTEMS AND METHODS FOR DESIGNING ORTHOPEDIC IMPLANTS BASED ON TISSUE CHARACTERISTICS";

U.S. application Ser. No. 17/100,396, filed Nov. 20, 2020, titled "PATIENT-SPECIFIC VERTEBRAL IMPLANTS WITH POSITIONING FEATURES";

U.S. application Ser. No. 17/531,417, filed Nov. 19, 2021, titled "PATIENT-SPECIFIC JIG FOR PERSONALIZED SURGERY";

U.S. application Ser. No. 17/835,777, filed Jun. 8, 2022, titled "PATIENT-SPECIFIC EXPANDABLE SPINAL IMPLANTS AND ASSOCIATED SYSTEMS AND METHODS";

International Patent Application No. PCT/US22/42188, filed Aug. 31, 2022, titled "BLOCKCHAIN MANAGED MEDICAL IMPLANTS";

U.S. application Ser. No. 17/851,487, filed Jun. 28, 2022, titled "PATIENT-SPECIFIC ADJUSTMENT OF SPINAL IMPLANTS, AND ASSOCIATED SYSTEMS AND METHODS";

U.S. application Ser. No. 17/856,625, filed Jul. 1, 2022, titled "MESHED NETWORK OF MEDICAL IMPLANTS";

U.S. application Ser. No. 17/867,621, filed Jul. 18, 2022, titled "PATIENT-SPECIFIC SACROILIAC IMPLANT, AND ASSOCIATED SYSTEMS AND METHODS";

U.S. application Ser. No. 17/842,242, filed Jun. 16, 2022, titled "PATIENT-SPECIFIC ANTERIOR PLATE IMPLANTS";

U.S. application Ser. No. 17/978,673, filed Nov. 1, 2022, titled "SPINAL IMPLANTS AND SURGICAL PROCEDURES WITH REDUCED SUBSIDENCE, AND ASSOCIATED SYSTEMS AND METHODS";

U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS";

U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES";

International Patent Application No. PCT/US22/48729, filed Nov. 2, 2022, titled "PATIENT-SPECIFIC ARTHROPLASTY DEVICES AND ASSOCIATED SYSTEMS AND METHODS";

U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGI-

CAL PLANS AND SYSTEMS AND METHODS FOR CREATING AND IMPLEMENTING THE SAME";

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS";

U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA"; and U.S. Application No. 63/437,966, filed Jan. 9, 2023, titled "SYSTEM FOR EDGE CASE PATHOLOGY IDENTIFICATION AND IMPLANT MANUFACTURING."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method for designing a patient-specific lumbar implant based on modeled anatomical changes, the method comprising:
- receiving patient data, the patient data including:
- image data of a spinal region of a patient, including at least portions of a lumbar spine, a thoracic spine, and a cervical spine of the patient;
- generating a virtual three-dimensional model of the spinal region based on the image data, the virtual three-dimensional model including the at least portions of the lumbar spine, the thoracic spine, and the cervical spine;
- virtually simulating changes along a spine of the patient caused by implantation of a patient-specific lumbar implant by:
  - determining one or more lumbar anatomical changes to the lumbar spine to provide a corrective adjustment based on at least one patient-specific lumbar implant that is virtually implanted along the lumbar spine in the virtual three-dimensional model;
  - determining one or more anatomical changes to at least one of the thoracic spine or the cervical spine of the patient caused by the one or more lumbar anatomical changes to the lumbar spine;
  - determining the one or more anatomical changes to at least one of the thoracic spine or the cervical spine of the patient are acceptable; and
  - displaying the virtual three-dimensional model showing the one or more lumbar anatomical changes and the one or more anatomical changes to at least one of the thoracic spine or the cervical spine of the patient; and
- designing the patient-specific lumbar implant configured to provide the corrective adjustment when implanted in the patient.

2. The computer-implemented method of claim 1, further comprising:
- modifying the virtual three-dimensional model according to one or more predetermined relationships between (A) the thoracic spine or the cervical spine and (B) the lumbar spine; and
- determining one or more anatomical changes based on the modified virtual three-dimensional model.

3. A computer-implemented method for designing a patient-specific lumbar implant based on modeled anatomical changes, the method comprising:
- receiving patient data, the patient data including:
  - image data of a spinal region of a patient, including at least portions of a lumbar spine, a thoracic spine, and a cervical spine of the patient;
- generating a virtual three-dimensional model of the spinal region based on the image data, the virtual three-dimensional model including the at least portions of the lumbar spine, the thoracic spine, and the cervical spine;
- virtually simulating changes along a spine of the patient caused by implantation of a patient-specific lumbar implant by:
  - determining one or more lumbar anatomical changes to the lumbar spine to provide a corrective adjustment based on at least one patient-specific lumbar implant that is virtually implanted along the lumbar spine in the virtual three-dimensional model;
  - determining one or more anatomical changes to at least one of the thoracic spine or the cervical spine of the patient are acceptable, wherein the one or more anatomical changes are caused by the one or more lumbar anatomical changes;
  - modeling, in the virtual three-dimensional model, the thoracic spine or the cervical spine as a singular anatomical structure; and
  - determining changes to the singular anatomical structure based on a position of the thoracic spine relative to the corrective adjustment to the lumbar spine; and
- designing the patient-specific lumbar implant configured to provide the corrective adjustment when implanted in the patient.

4. The computer-implemented method of claim 1, further comprising:
- simulating a range of motion by the patient; and
- determining whether the corrective adjustment to the lumbar spine increases the range of motion by the patient.

5. The computer-implemented method of claim 1, further comprising:
- simulating an anatomical alignment of the at least portions of the lumbar spine, the thoracic spine, and the cervical spine the patient; and
- determining whether the corrective adjustment to the lumbar spine impacts anatomical alignment of the cervical spine or the thoracic spine.

6. A computer-implemented method for designing a patient-specific lumbar implant based on modeled anatomical changes, the method comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient are acceptable, wherein the one or more anatomical changes are caused by the one or more lumbar anatomical changes;

receiving patient pain data;

determining one or more adjustments to the virtual three-dimensional model of a spinal anatomy of the patient based at least partially on the received patient pain data; and determining a pain reduction score based on the one or more adjustments; and after determining the pain reduction score, designing the patient-specific lumbar implant configured to provide the corrective adjustment when implanted in the patient.

7. The computer-implemented method of claim 1, further comprising:

analyzing the virtual three-dimensional model to determine a mobility score and a pain score for the patient based on the corrective adjustment.

8. The computer-implemented method of claim 7, wherein analyzing the virtual three-dimensional model includes using a trained machine learning model, wherein the trained machine learning model was trained based on previous patient virtual models, pain scores, and surgical outcomes.

9. The computer-implemented method of claim 1, further comprising:

generating a report based on simulated changes along the spine of the patient caused by implantation of a patient-specific implant virtually in the virtual three-dimensional model, wherein the report includes predictions, modeling, simulations, and/or anatomical effects resulting from the corrective adjustment to the lumbar spine.

10. The computer-implemented method of claim 1, further comprising:

simulating a spinal load transfer via the lumbar spine to one or more adjacent anatomical features of the patient; and modifying the lumbar spine to be in a predetermined anatomical configuration to adjust the one or more adjacent anatomical features to predetermined configurations.

11. The computer-implemented method of claim 1, further comprising:

determining one or more muscle or tissue anatomical changes based on the corrective adjustment to the spine.

12. A system comprising:

one or more processors; and one or more memories storing instructions that, when executed by the one or more processors, cause the system to perform a process for designing a patient-specific lumbar implant based on modeled anatomical changes, the process comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient caused by the one or more lumbar anatomical changes to the lumbar spine;

determining the one or more anatomical changes to at least one of the thoracic spine or the cervical spine of the patient are acceptable; and displaying the virtual three-dimensional model showing the one or more lumbar anatomical changes and the one or more anatomical changes to at least one of the thoracic spine or the cervical spine of the patient; and designing the patient-specific lumbar implant configured to provide the corrective adjustment when implanted in the patient.

13. The system of claim 12, wherein the process further comprises:

modifying the virtual three-dimensional model according to one or more predetermined relationships between (A) the thoracic spine or the cervical spine and (B) the lumbar spine; and determining one or more anatomical changes based on the modified virtual three-dimensional model.

14. A system comprising:

one or more processors; and one or more memories storing instructions that, when executed by the one or more processors, cause the system to perform a process for designing a patient-specific lumbar implant based on modeled anatomical changes, the process comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient are acceptable, wherein the one or more anatomical changes are caused by the one or more lumbar anatomical changes;

modeling, in the virtual three-dimensional model, the thoracic spine or the cervical spine as a singular anatomical structure; and determining changes to the singular anatomical structure based on a position of the thoracic spine relative to the corrective adjustment to the lumbar spine; and designing the patient-specific lumbar implant configured to provide the corrective adjustment when implanted in the patient.

15. The system of claim 12, wherein the process further comprises: simulating a range of motion by the patient; and determining whether the corrective adjustment to the lumbar spine increases the range of motion by the patient.

16. The system of claim 12, wherein the process further comprises:

simulating an anatomical alignment of the at least portions of the lumbar spine, the thoracic spine, and the cervical spine the patient; and determining whether the corrective adjustment to the lumbar spine impacts anatomical alignment of the cervical spine or the thoracic spine.

17. A system comprising:

one or more processors; and one or more memories storing instructions that, when executed by the one or more processors, cause the system to perform a process for designing a patient-specific lumbar implant based on modeled anatomical changes, the process comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient are acceptable, wherein the one or more anatomical changes are caused by the one or more lumbar anatomical changes;

receiving patient pain data;

determining one or more adjustments to the virtual three-dimensional model of a spinal anatomy of the patient based at least partially on the received patient pain data; and determining a pain reduction score based on the one or more adjustments;

after determining the pain reduction score, designing the patient-specific lumbar implant configured to provide the corrective adjustment when implanted in the patient.

18. The system of claim 16, wherein the process further comprises:

analyzing the virtual three-dimensional model to determine a mobility score and a pain score for the patient based on the corrective adjustment.

19. The system of claim 18, wherein analyzing the virtual three-dimensional model includes using a trained machine learning model, wherein the trained machine learning model was trained based on previous patient virtual models, pain scores, and surgical outcomes.

20. The system of claim 12, further comprising:

generating a report based on simulated changes along the spine of the patient caused by implantation of a patient-specific implant virtually in the virtual three-dimensional model, wherein the report includes predictions, modeling, simulations, and/or anatomical effects resulting from the corrective adjustment to the lumbar spine.

21. The system of claim 12, further comprising:

simulating a spinal load transfer via the lumbar spine to one or more adjacent anatomical features of the patient; and modifying the lumbar spine to be in a predetermined anatomical configuration to adjust the one or more adjacent anatomical features to predetermined configurations.

22. The system of claim 12, further comprising:

determining one or more muscle or tissue anatomical changes based on the corrective adjustment to the spine.

23. A non-transitory computer-readable medium storing instructions that, when executed by a computing system, cause the computing system to perform operations for designing a patient-specific lumbar implant based on modeled anatomical changes, the operations comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient caused by the one or more lumbar anatomical changes to the lumbar spine;

determining the one or more anatomical changes to at least one of the thoracic spine or the cervical spine of the patient are acceptable; and displaying the virtual three-dimensional model showing the one or more lumbar anatomical changes and the one or more anatomical changes to at least one of the thoracic spine or the cervical spine of the patient; and designing the patient-specific lumbar implant configured to provide the corrective adjustment when implanted in the patient.

24. The non-transitory computer-readable medium of claim 23, wherein the operations further comprise:

modifying the virtual three-dimensional model according to one or more predetermined relationships between (A) the thoracic spine or the cervical spine and (B) the lumbar spine; and determining one or more anatomical changes based on the modified virtual three-dimensional model.

25. A non-transitory computer-readable medium storing instructions that, when executed by a computing system, cause the computing system to perform operations for designing a patient-specific lumbar implant based on modeled anatomical changes, the operations comprising:

receiving patient data, the patient data including:

image data of a spinal region of a patient, including at least portions of a lumbar spine, a thoracic spine, and a cervical spine of the patient;

generating a virtual three-dimensional model of the spinal region based on the image data, the virtual three-dimensional model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual three-dimensional model;

determining one or more anatomical changes to at least one of the thoracic spine or the cervical spine of the patient are acceptable, wherein the one or more anatomical changes are caused by the one or more lumbar anatomical changes;

modeling, in the virtual three-dimensional model, the thoracic spine or the cervical spine as a singular anatomical structure; and determining changes to the singular anatomical structure based on a position of the thoracic spine relative to the corrective adjustment to the lumbar spine; and designing the patient-specific lumbar implant configured to provide the corrective adjustment when implanted in the patient.

26. A computer-implemented method for designing a patient-specific lumbar implant, the method comprising:

receiving patient data, the patient data including:

image data of a spinal region of a patient, including at least portions of a lumbar spine, a thoracic spine, and a cervical spine of the patient;

generating a virtual anatomical model of the spinal region based on the image data, the virtual anatomical model including the at least portions of the lumbar spine, the thoracic spine, and the cervical spine;

virtually simulating changes along a spine of the patient caused by implantation of a patient-specific lumbar implant by:

determining one or more lumbar anatomical changes to the lumbar spine to provide a corrective adjustment based on at least one patient-specific lumbar implant that is virtually implanted along the lumbar spine in the virtual anatomical model;

determining one or more anatomical changes to at least one of the thoracic spine or the cervical spine of the patient caused by the one or more lumbar anatomical changes to the lumbar spine;

determining the one or more anatomical changes to at least one of the thoracic spine or the cervical spine of the patient are acceptable; and displaying the virtual anatomical model showing the one or more lumbar anatomical changes and the one or more anatomical changes to at least one of the thoracic spine or the cervical spine of the patient; and designing the patient-specific lumbar implant configured to provide the corrective adjustment when implanted in the patient.

27. The method of claim 26, further comprising receiving post-operative patient pain data;

determining a pain reduction score based on the post-operative patient pain.

* * * * *